(12) United States Patent
Yang et al.

(10) Patent No.: US 11,666,684 B2
(45) Date of Patent: Jun. 6, 2023

(54) MULTILAYERED CELL SHEET OF NEURAL CREST STEM CELLS AND METHOD OF PREPARING THE SAME

(71) Applicant: INJE UNIVERSITY INDUSTRY-ACADEMIC COOPERATION FOUNDATION, Gimhae-si Gyeongsangnam-do (KR)

(72) Inventors: Young-Il Yang, Busan (KR); Won-Jin Lee, Busan (KR); Jong-Tae Kim, Yangsan-si (KR)

(73) Assignee: INJE UNIVERSITY INDUSTRY-ACADEMIC COOPERATION FOUNDATION, Gimhae (KR)

( * ) Notice: Subject to any disclaimer, the term of this patent is extended or adjusted under 35 U.S.C. 154(b) by 505 days.

(21) Appl. No.: 15/773,171

(22) PCT Filed: Dec. 18, 2017

(86) PCT No.: PCT/KR2017/014958
§ 371 (c)(1),
(2) Date: May 3, 2018

(87) PCT Pub. No.: WO2018/117573
PCT Pub. Date: Jun. 28, 2018

(65) Prior Publication Data
US 2019/0070337 A1 Mar. 7, 2019

(30) Foreign Application Priority Data
Dec. 20, 2016 (KR) .................. 10-2016-0174543

(51) Int. Cl.
| | | |
|---|---|---|
| *A61L 27/52* | (2006.01) | |
| *A61L 27/38* | (2006.01) | |
| *C12N 5/00* | (2006.01) | |
| *C12N 5/0797* | (2010.01) | |
| *A61L 27/26* | (2006.01) | |
| *A61K 35/30* | (2015.01) | |
| *A61L 27/36* | (2006.01) | |
| *A61L 27/22* | (2006.01) | |
| *A61L 27/24* | (2006.01) | |
| *A61L 27/54* | (2006.01) | |
| *C12N 5/0735* | (2010.01) | |
| *A61P 29/00* | (2006.01) | |

(52) U.S. Cl.
CPC .............. *A61L 27/52* (2013.01); *A61K 35/30* (2013.01); *A61L 27/225* (2013.01); *A61L 27/24* (2013.01); *A61L 27/26* (2013.01); *A61L 27/3604* (2013.01); *A61L 27/3633* (2013.01); *A61L 27/3658* (2013.01); *A61L 27/3834* (2013.01); *A61L 27/54* (2013.01); *C12N 5/0068* (2013.01); *C12N 5/0606* (2013.01); *C12N 5/0623* (2013.01); *A61P 29/00* (2018.01); *C12N 2501/117* (2013.01); *C12N 2501/119* (2013.01); *C12N 2501/13* (2013.01); *C12N 2501/135* (2013.01); *C12N 2501/15* (2013.01); *C12N 2501/165* (2013.01); *C12N 2501/17* (2013.01); *C12N 2501/231* (2013.01); *C12N 2501/2306* (2013.01); *C12N 2533/52* (2013.01); *C12N 2533/54* (2013.01); *C12N 2533/56* (2013.01); *C12N 2533/90* (2013.01)

(58) Field of Classification Search
CPC ....................................................... A61L 27/52
USPC ......................................................... 424/93.7
See application file for complete search history.

(56) References Cited

U.S. PATENT DOCUMENTS

| 2006/0019235 A1 * | 1/2006 | Soen et al. .............. C12Q 1/00 435/4 |
| 2016/0121025 A1 * | 5/2016 | Yamashita et al. ..... A61L 27/52 |

FOREIGN PATENT DOCUMENTS

| EP | 2 845 898 B1 * | 11/2015 | ........... C12N 5/0797 |
| EP | 2845898 B1 * | 7/2017 | ........... C12N 5/0623 |
| KR | 10-2012-0126284 A | 11/2012 | |
| KR | 10-2013-0008145 A | 1/2013 | |
| KR | 10-2013-0124076 A | 11/2013 | |
| KR | 10-2016-0005366 A | 1/2016 | |

OTHER PUBLICATIONS

Hu et al. "Epidermal neural crest stem cell (EPI-NCSC) mediated recovery of sensory function in a mouse model of spinal cord injury." Stem cell reviews and reports 6.2 (2010): 186-198 (Year: 2010).*

International Search Report for PCT/KR2017/014958 dated Apr. 6, 2018 from Korean Intellectual Property Office.

Jong-Tae Kim, "Biologic Role and Benefit of Neural Crest Stem Cells—Derived from the Adult Peripheral Nerve in a Spinal Cord Injury Model of Rats", Thesis for Doctor Degree, Department of Medicine (Pathology), Graduate School, Inje University.

* cited by examiner

*Primary Examiner* — Janet L Epps-Smith
*Assistant Examiner* — Alexander W Nicol
(74) *Attorney, Agent, or Firm* — Revolution IP, PLLC

(57) ABSTRACT

A method of manufacturing a multilayered cell sheet of neural crest stem cells (NCSCs), includes: (1) isolating and culturing NCSCs from peripheral nerves; (2) embedding the cultured NCSCs in a hydrogel; (3) culturing the hydrogel comprising the NCSCs embedded therein under stressed culture conditions in which a physical support is applied; and (4) culturing the resulting hydrogel of step (3) under non-stressed culture conditions in which a physical support is removed.

2 Claims, 34 Drawing Sheets

[FIG. 1]
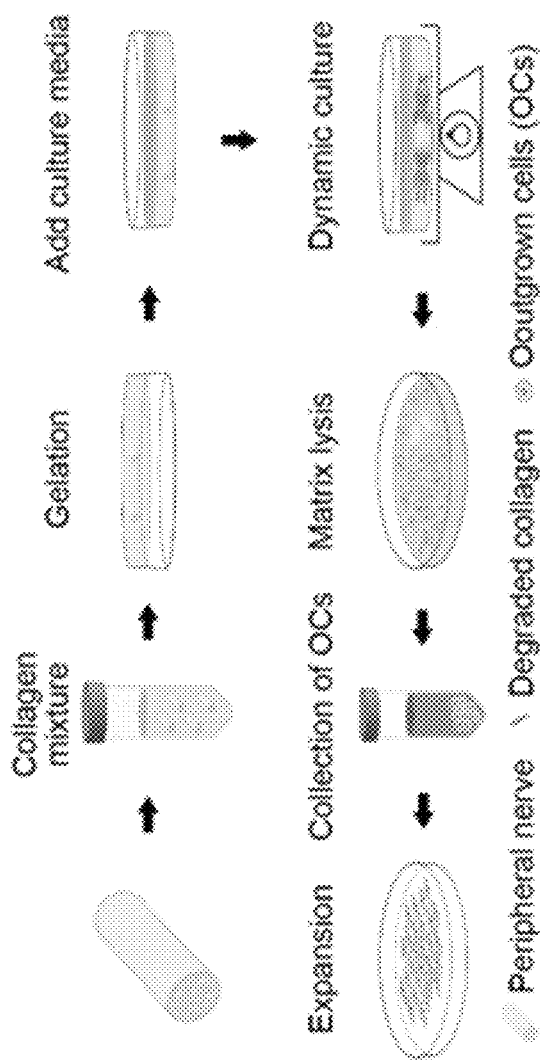
[FIG. 2]
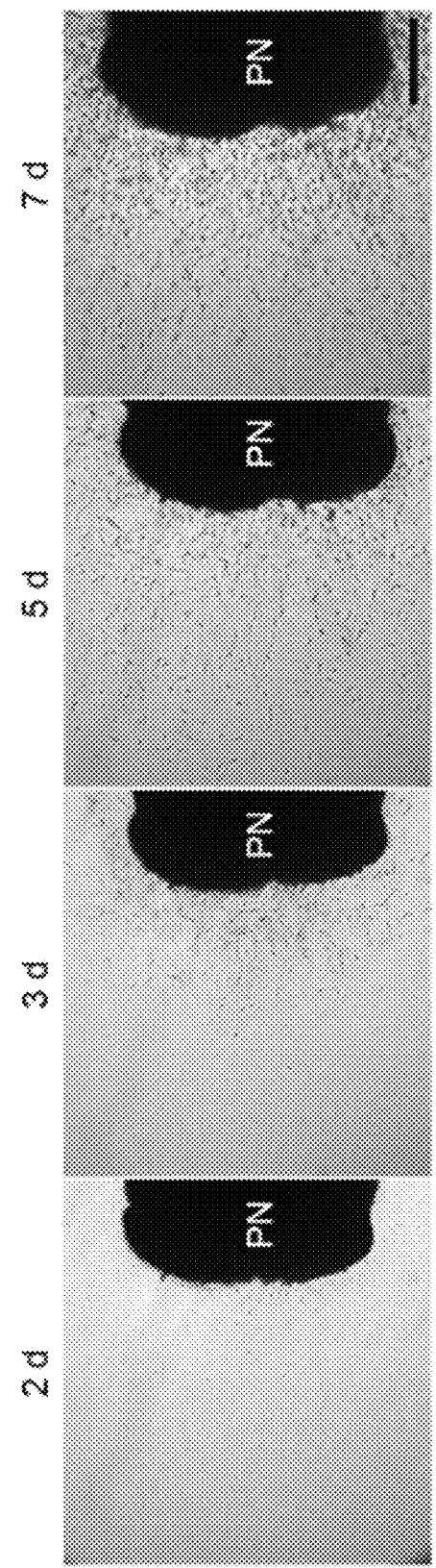

[FIG. 3]
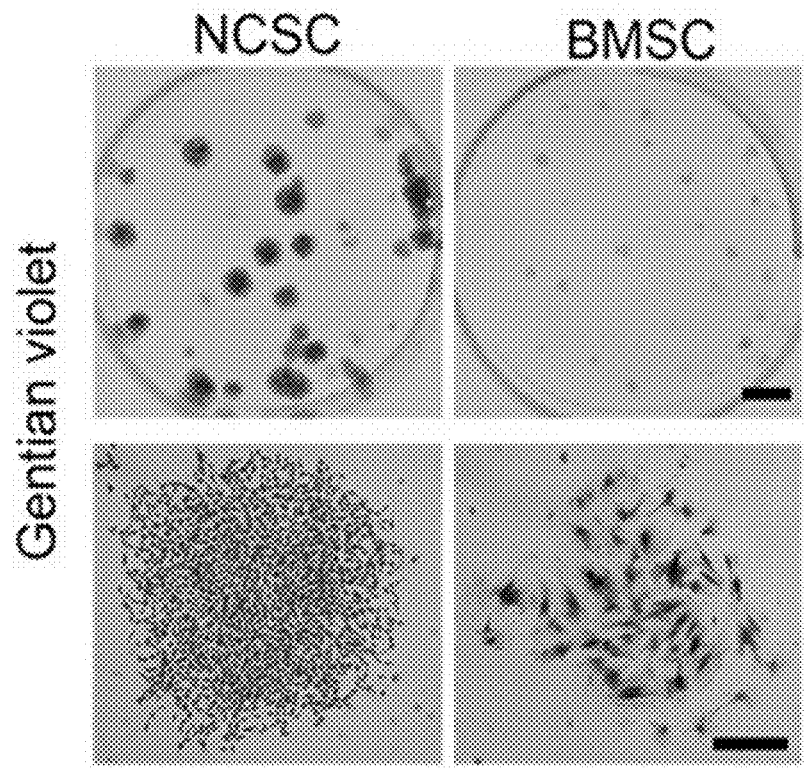
[FIG. 4]
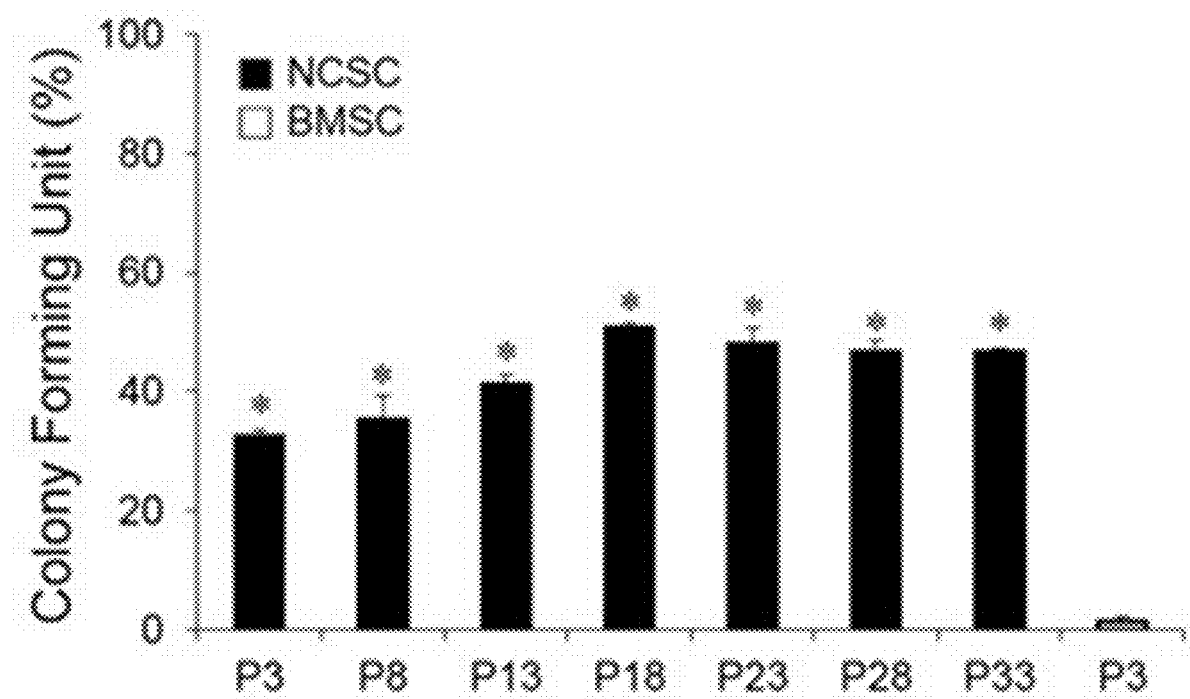

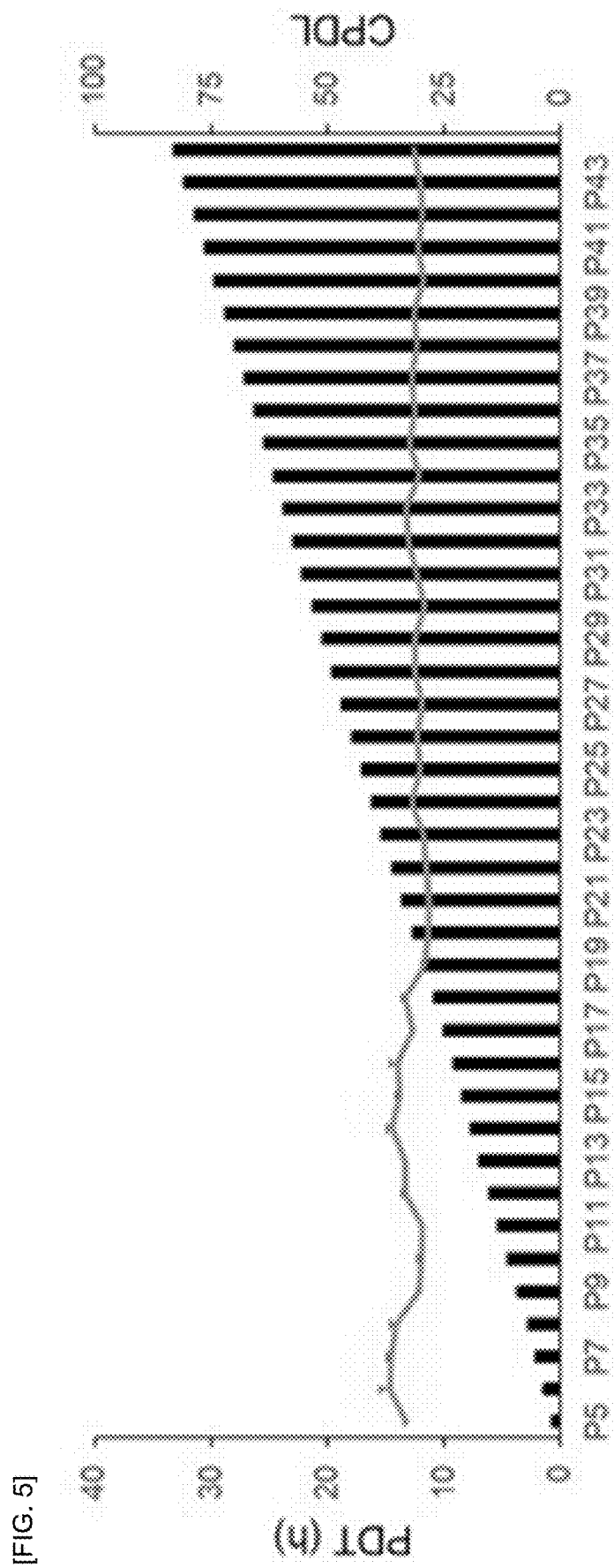
[FIG. 5]

[FIG. 6]
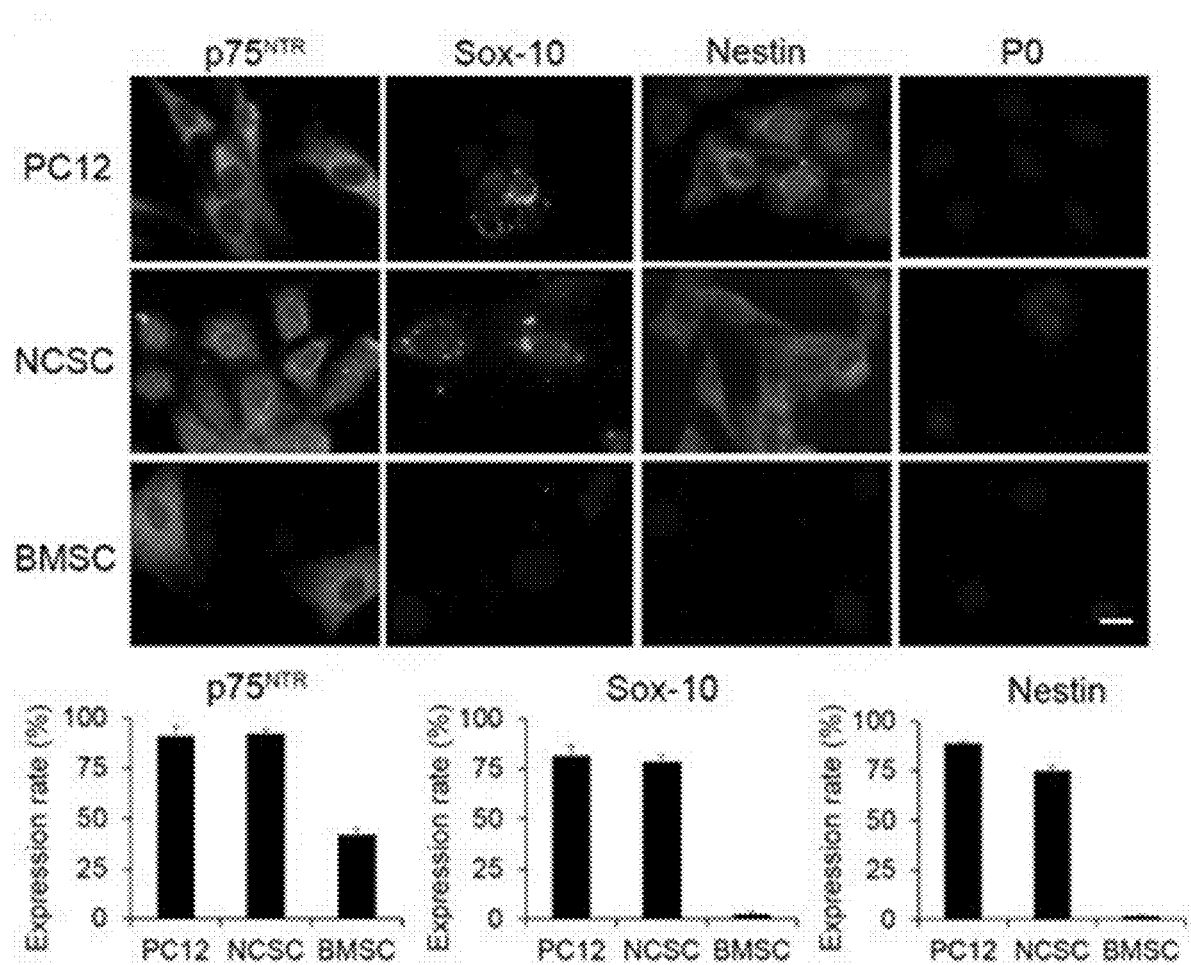

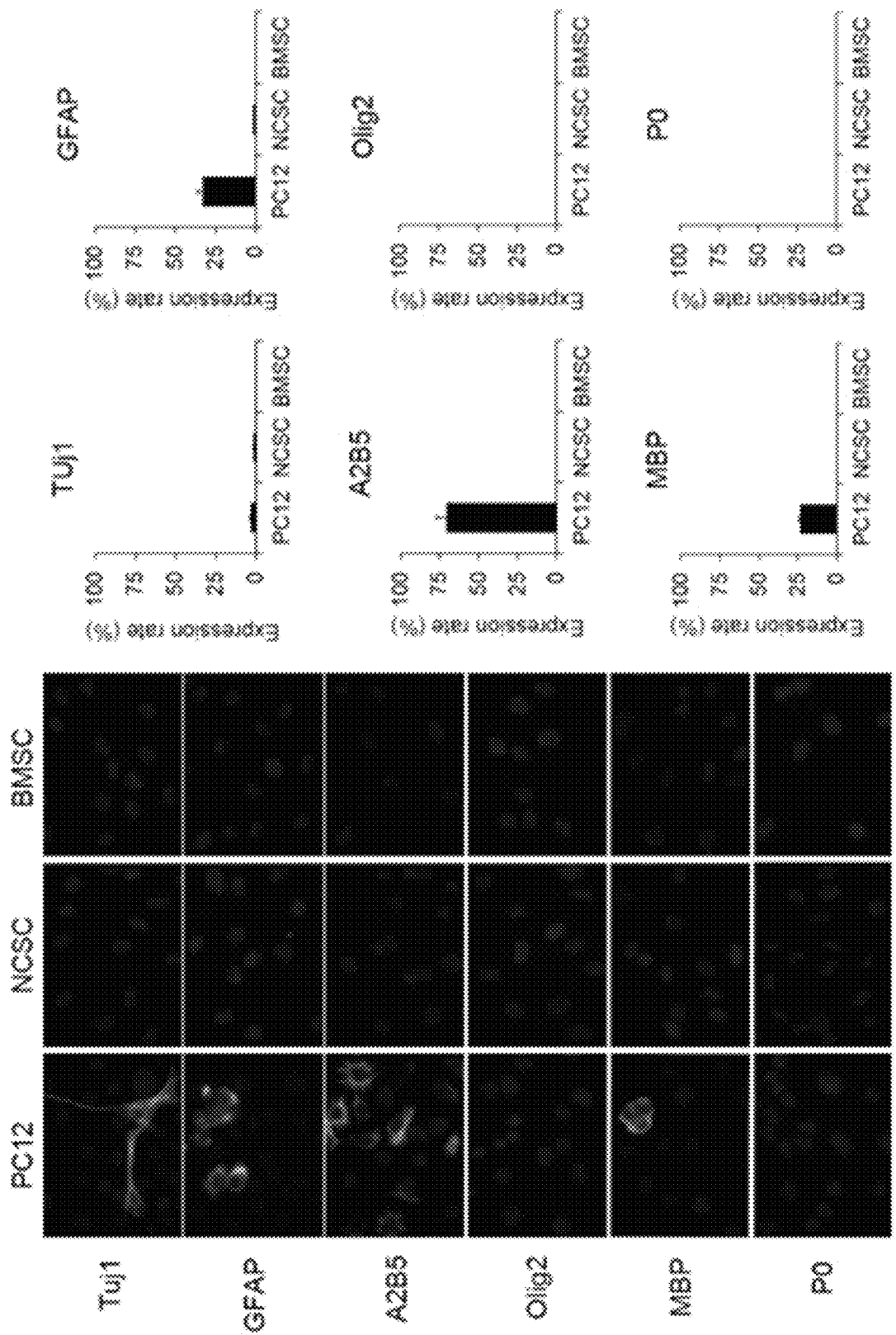
[FIG. 7]

[FIG. 8]
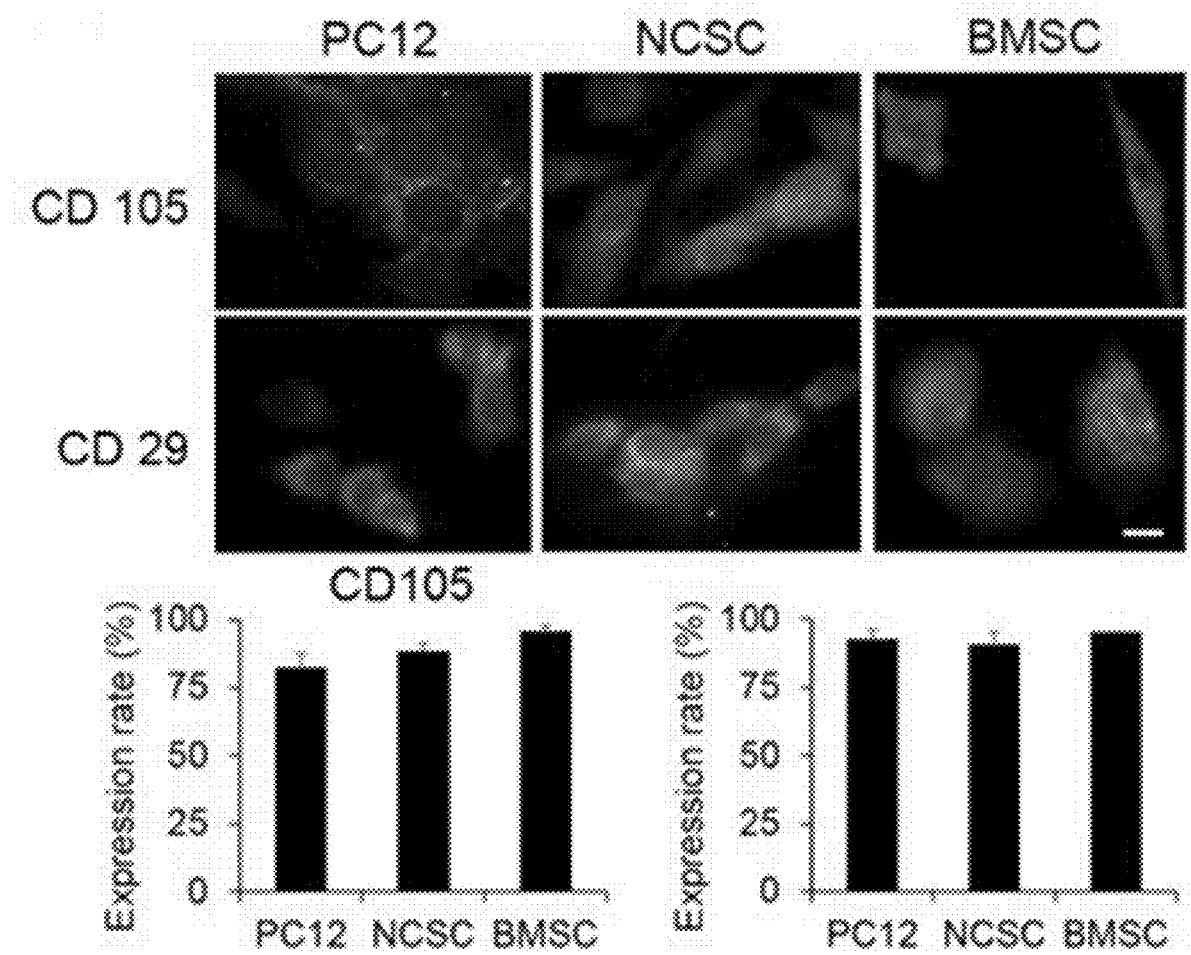
[FIG. 9]
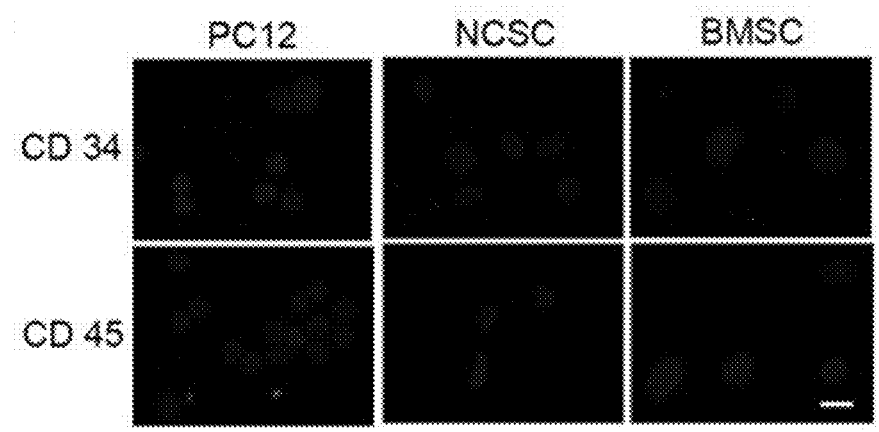

[FIG. 10]
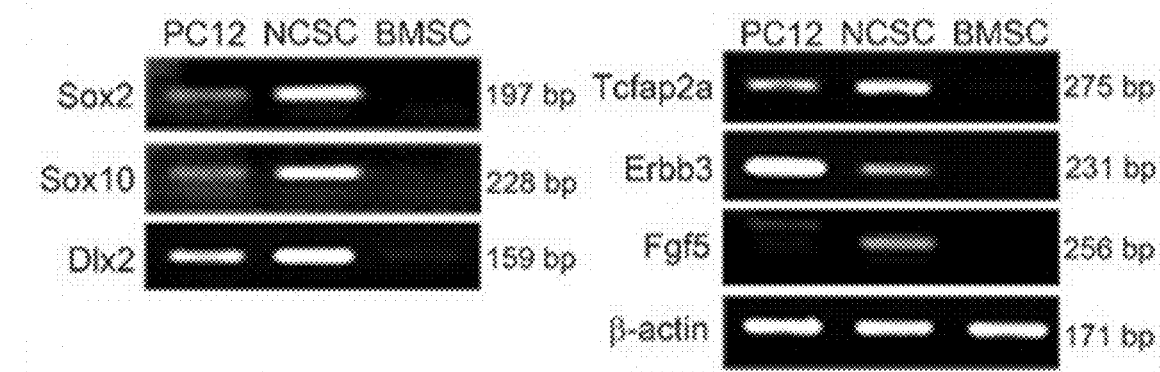
[FIG. 11]
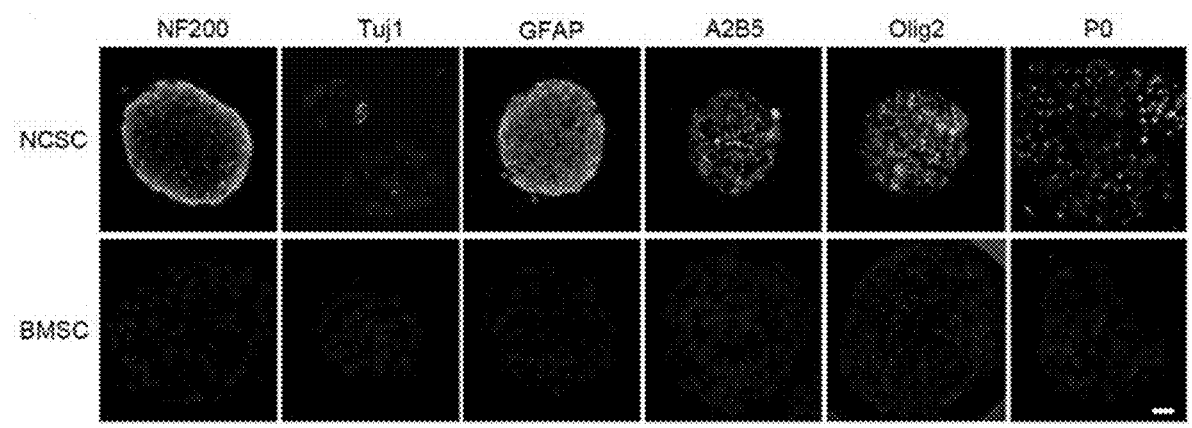
[FIG. 12]
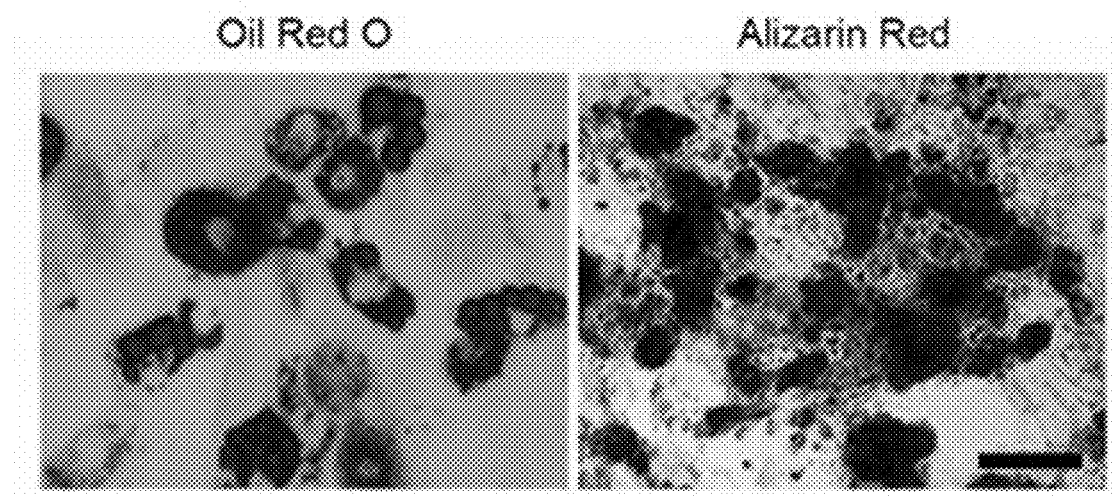

[FIG. 13]
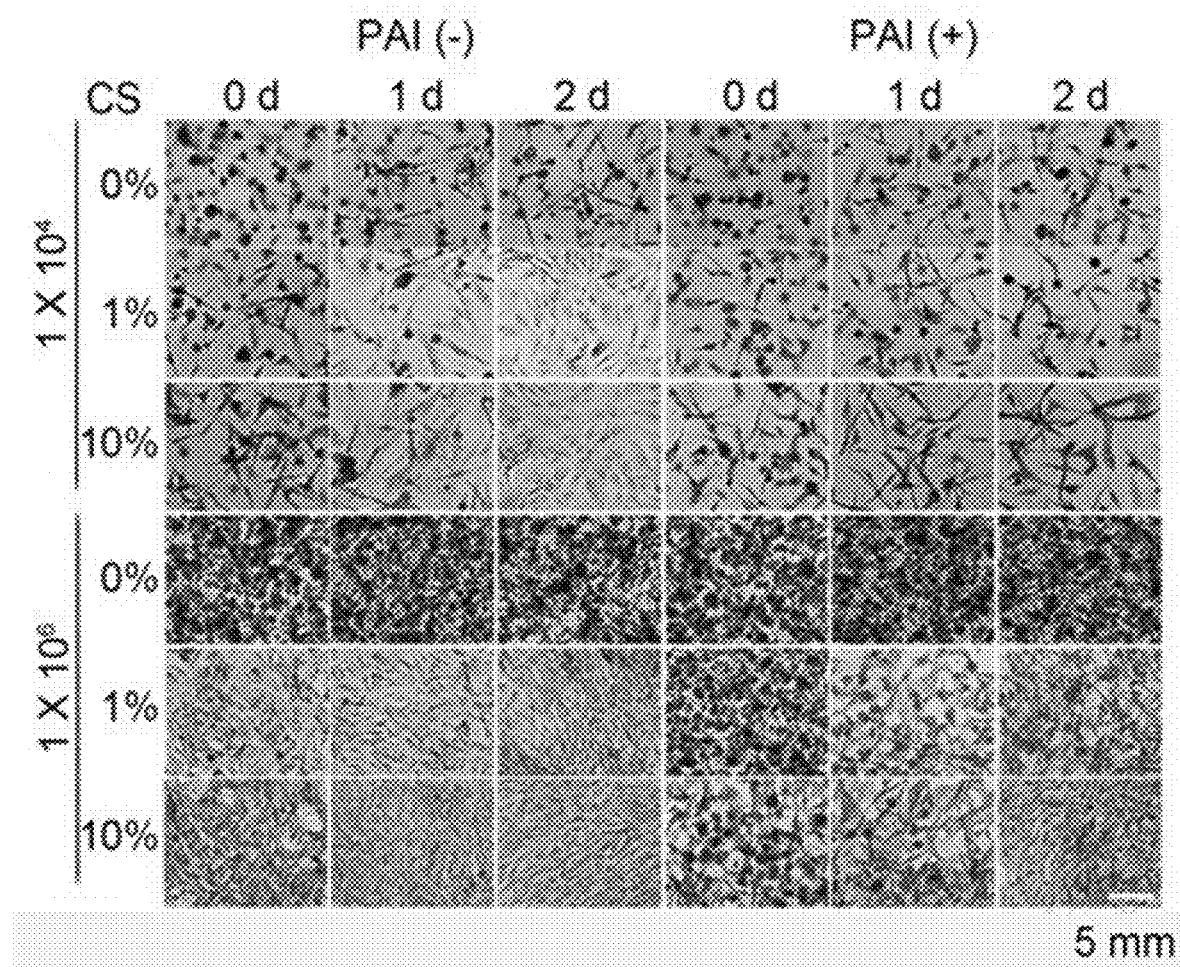
[FIG. 14]
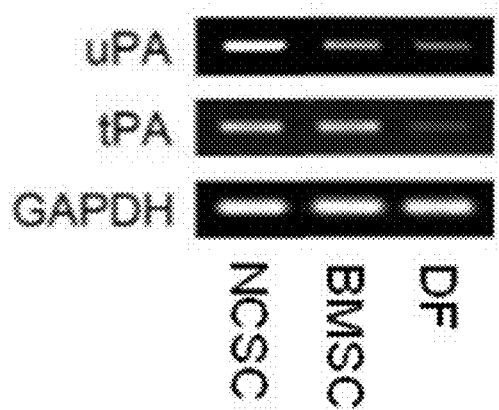

[FIG. 15]
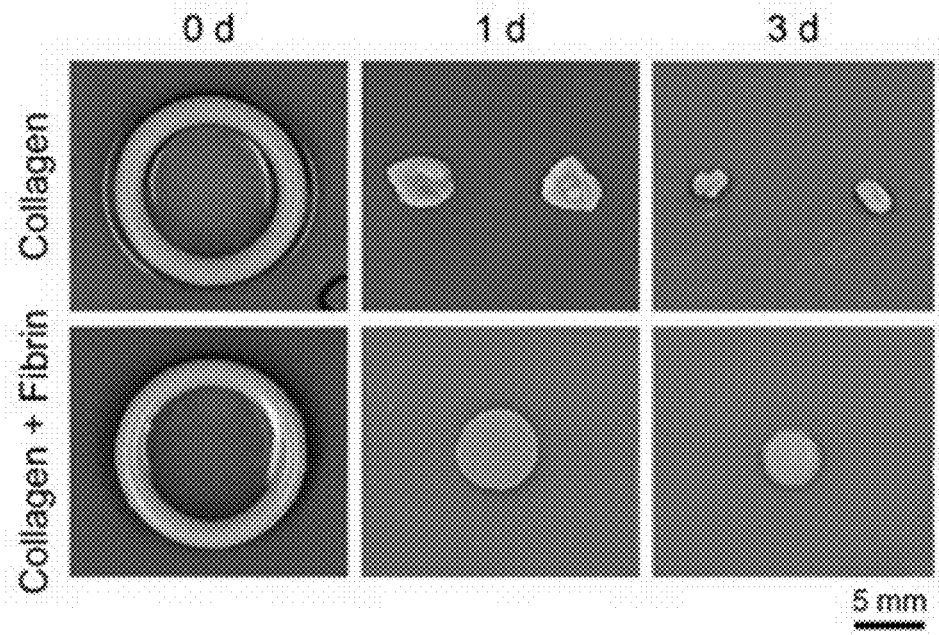
[FIG. 16]
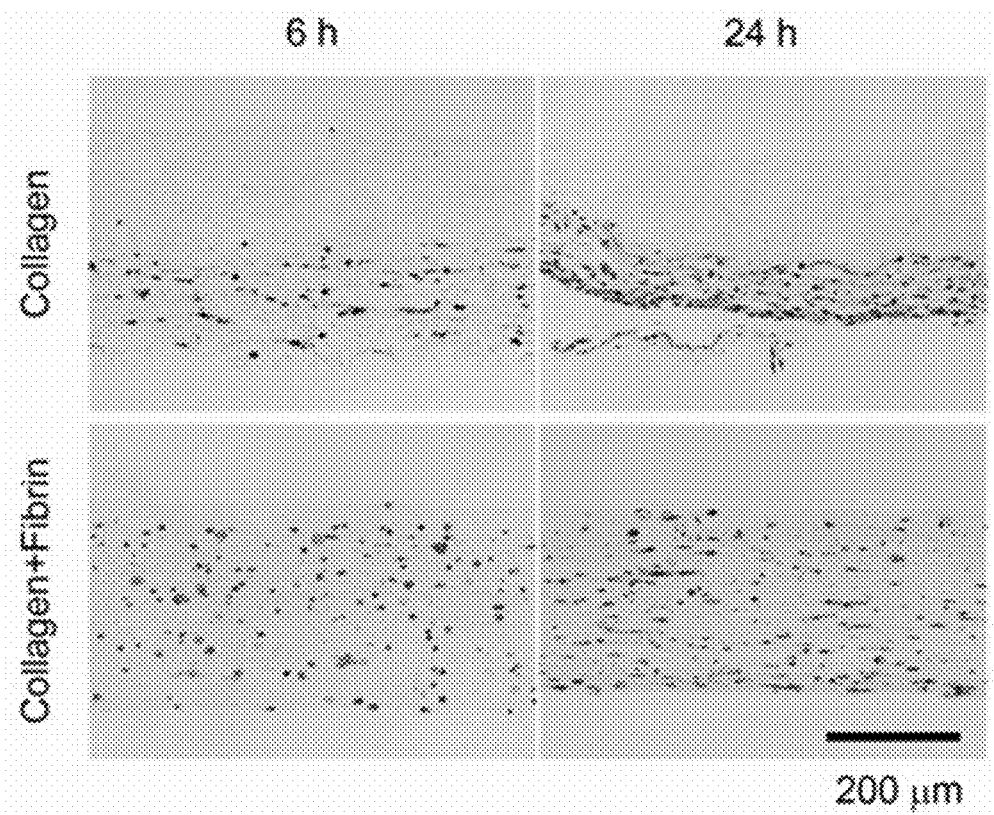

[FIG. 17]
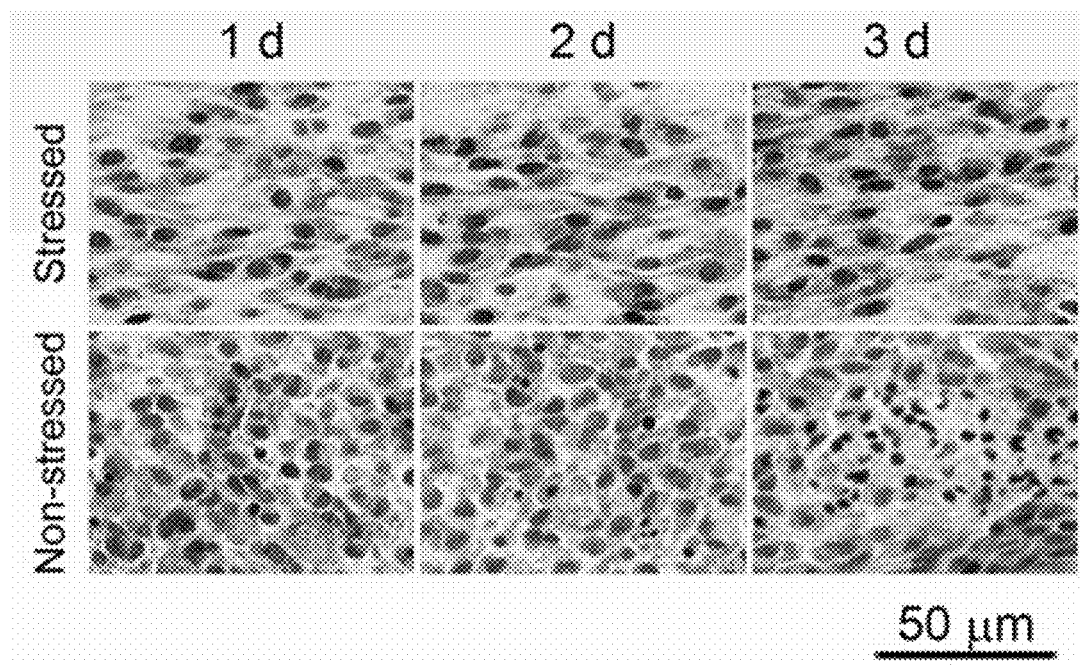

[FIG. 18]
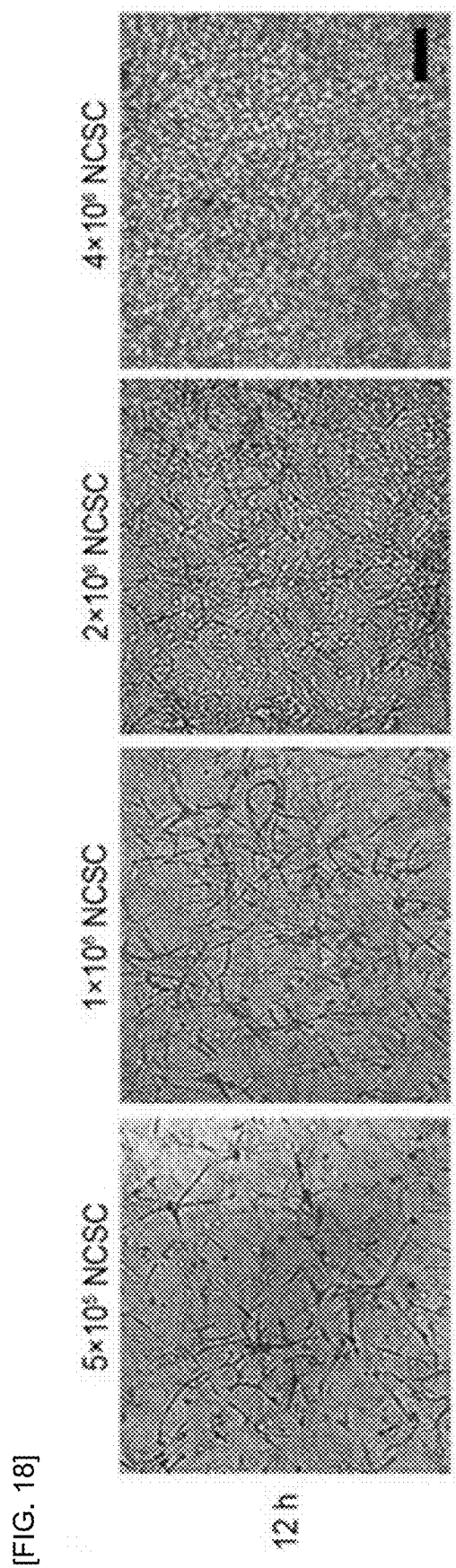

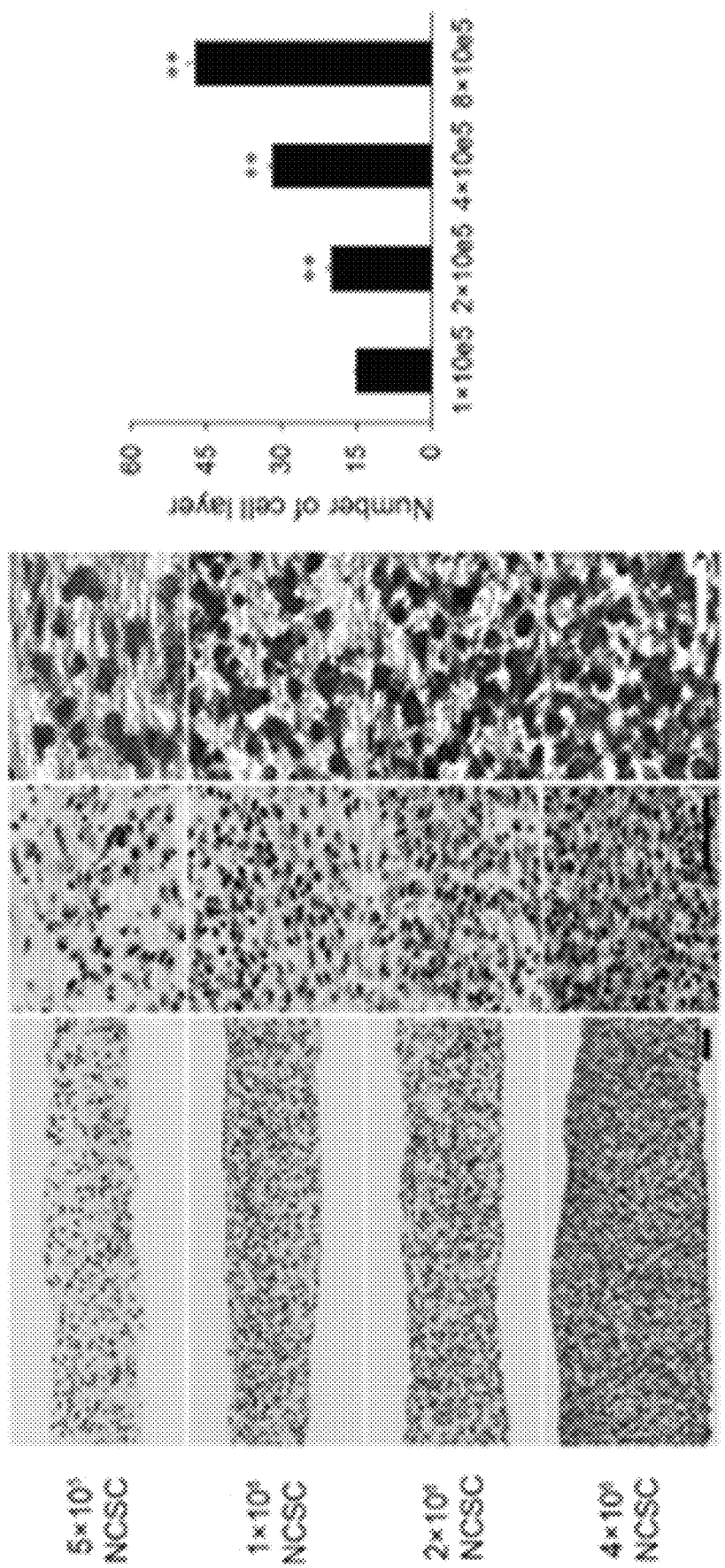
[FIG. 19]

[FIG. 20]
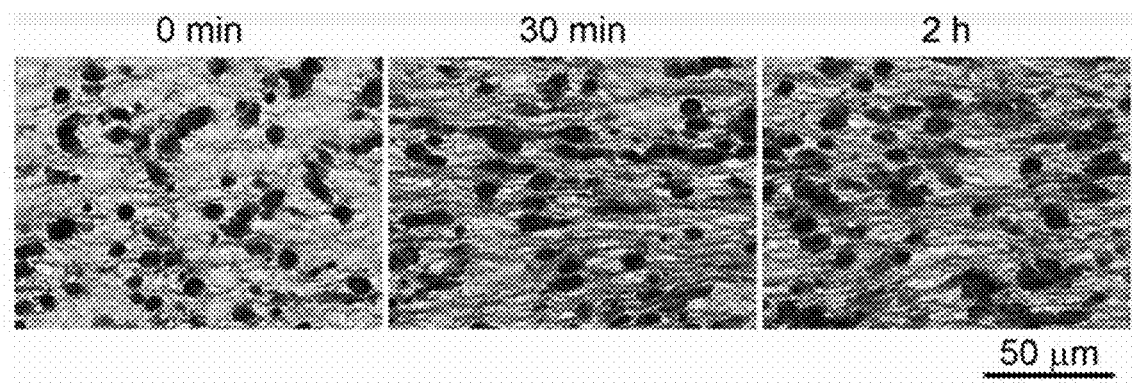
[FIG. 21]
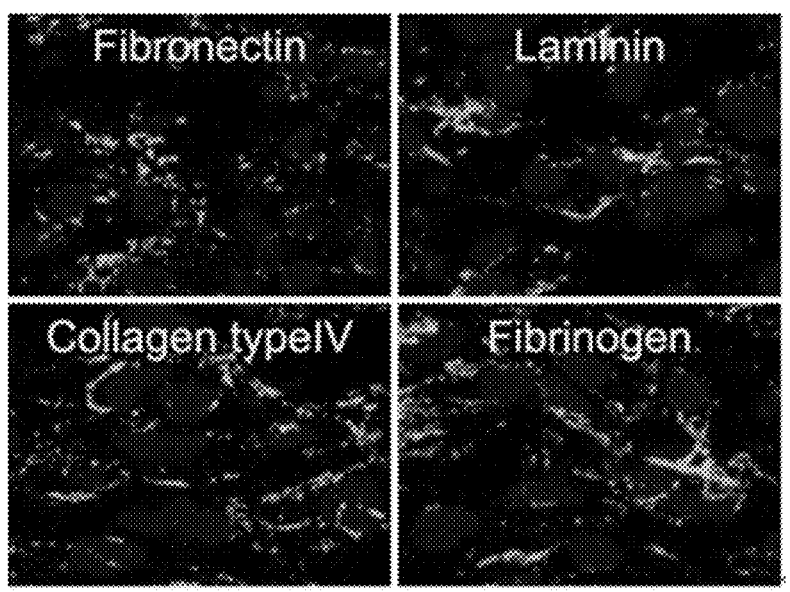

[FIG. 22]
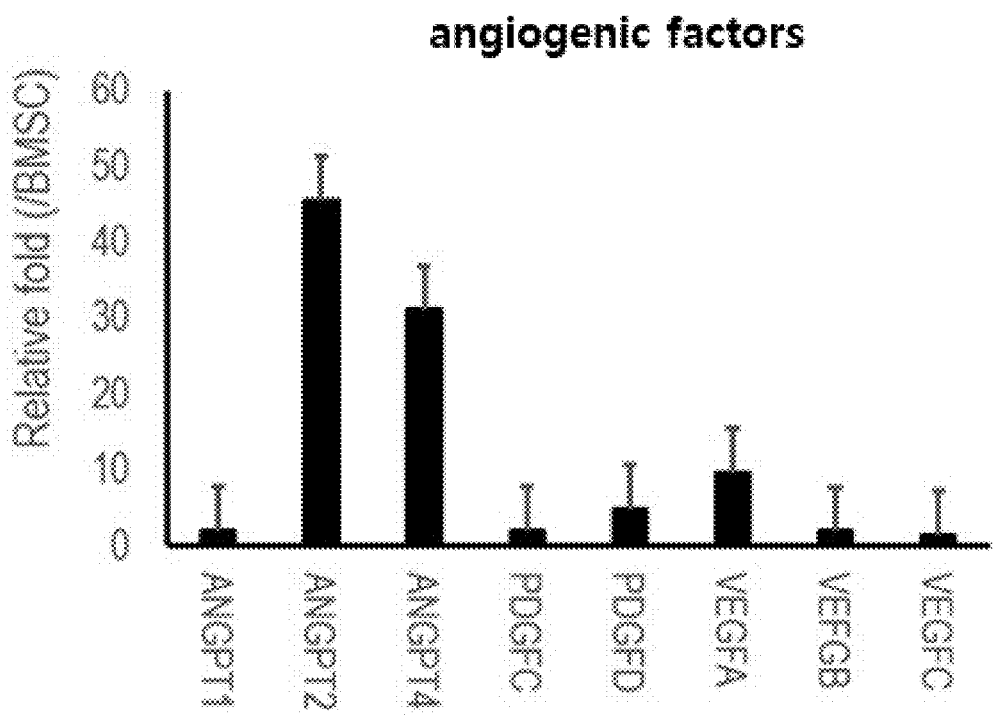
[FIG. 23]
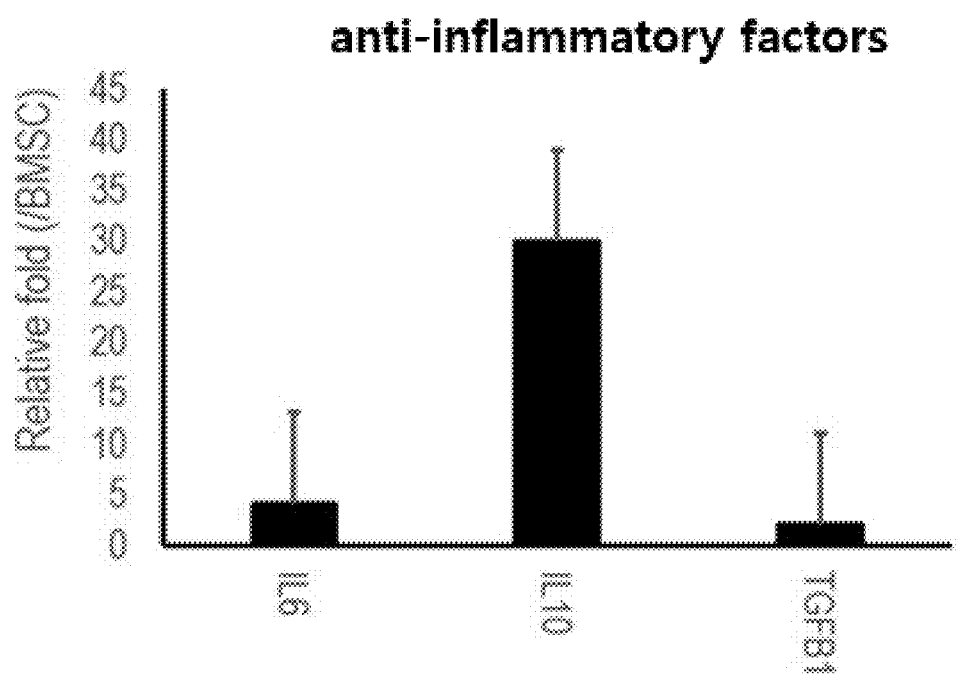

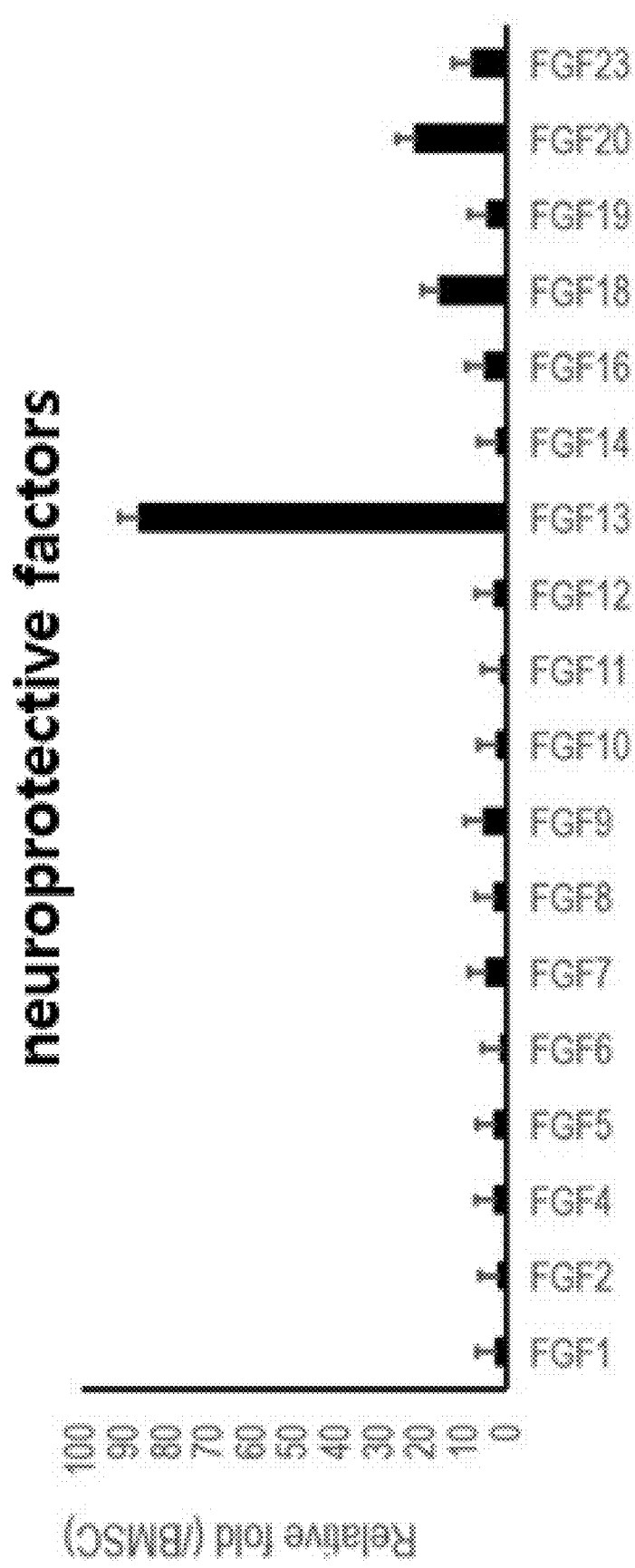
[FIG. 24]

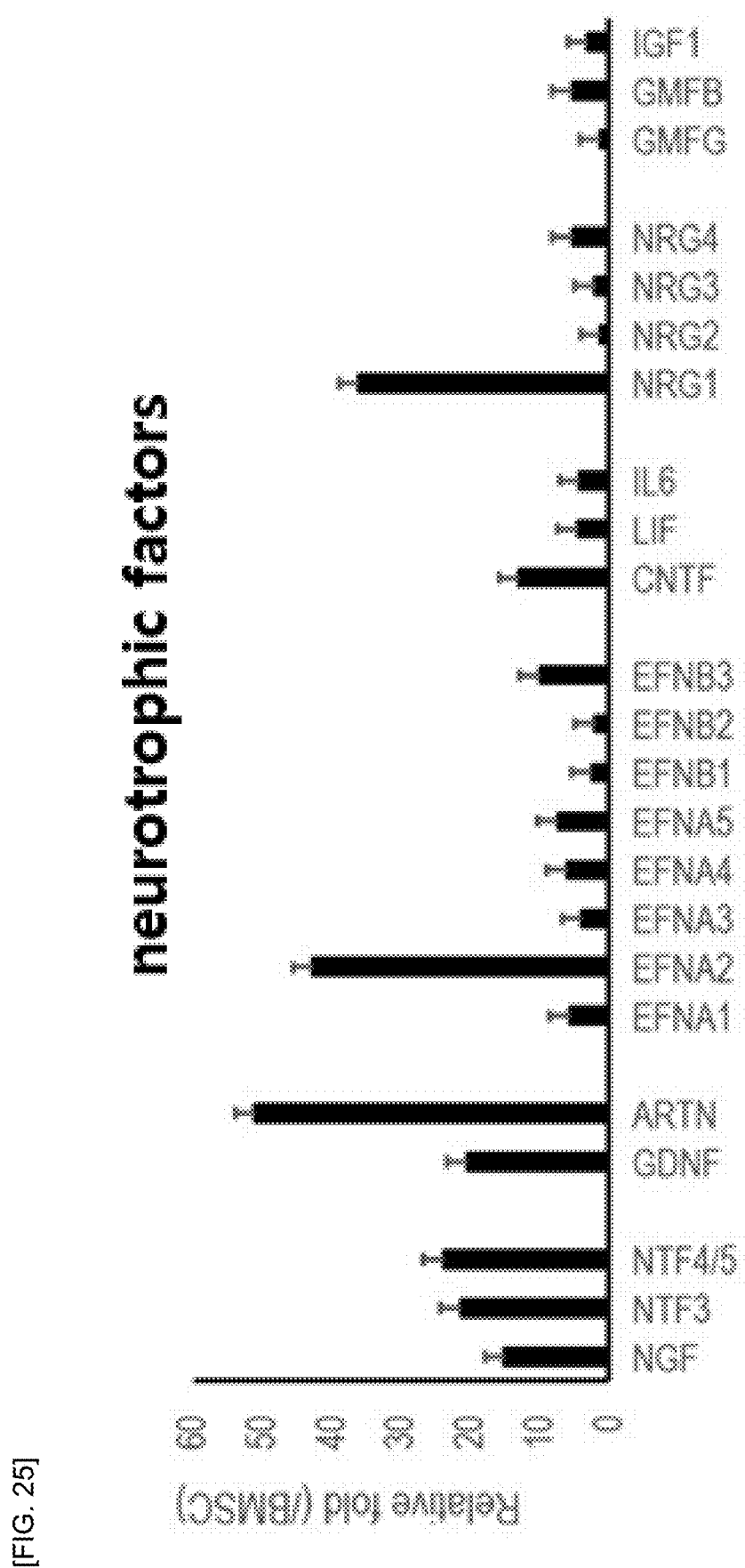
[FIG. 25]

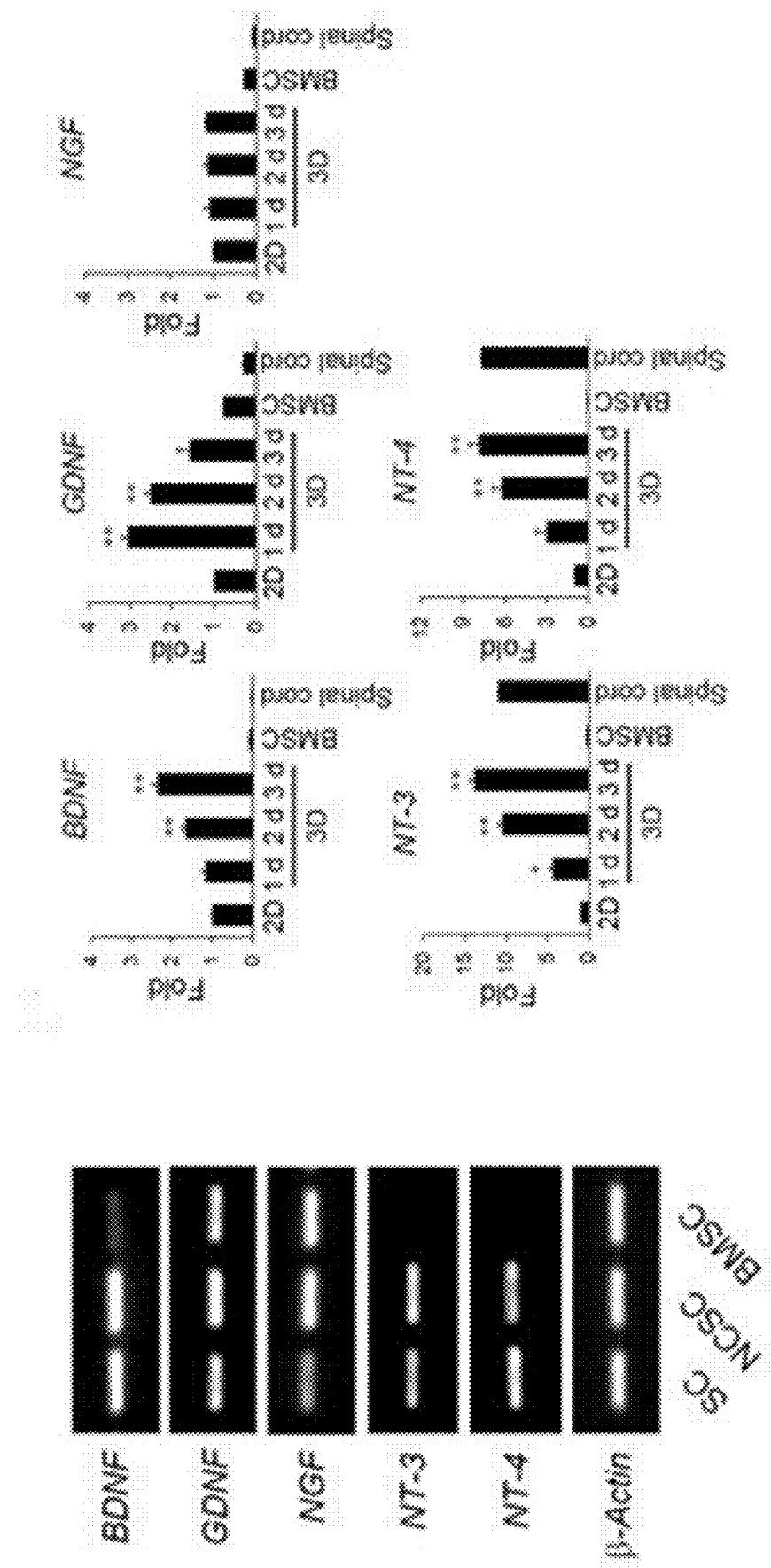
[FIG. 26]

[FIG. 27]
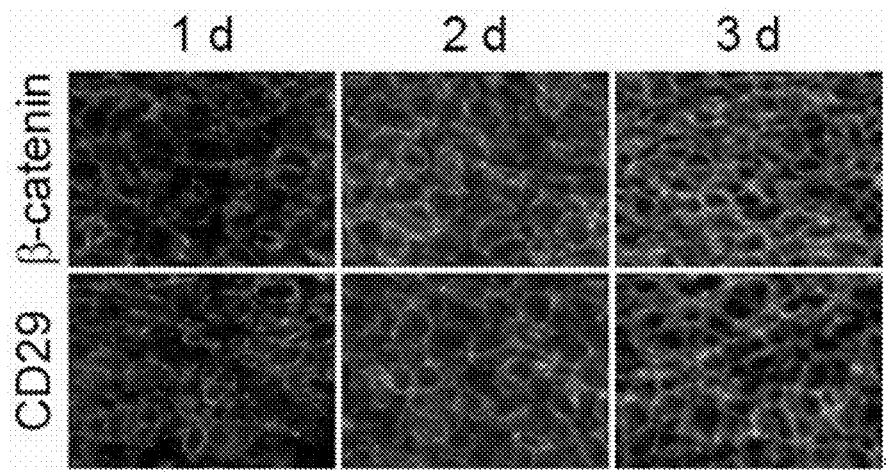
[FIG. 28]
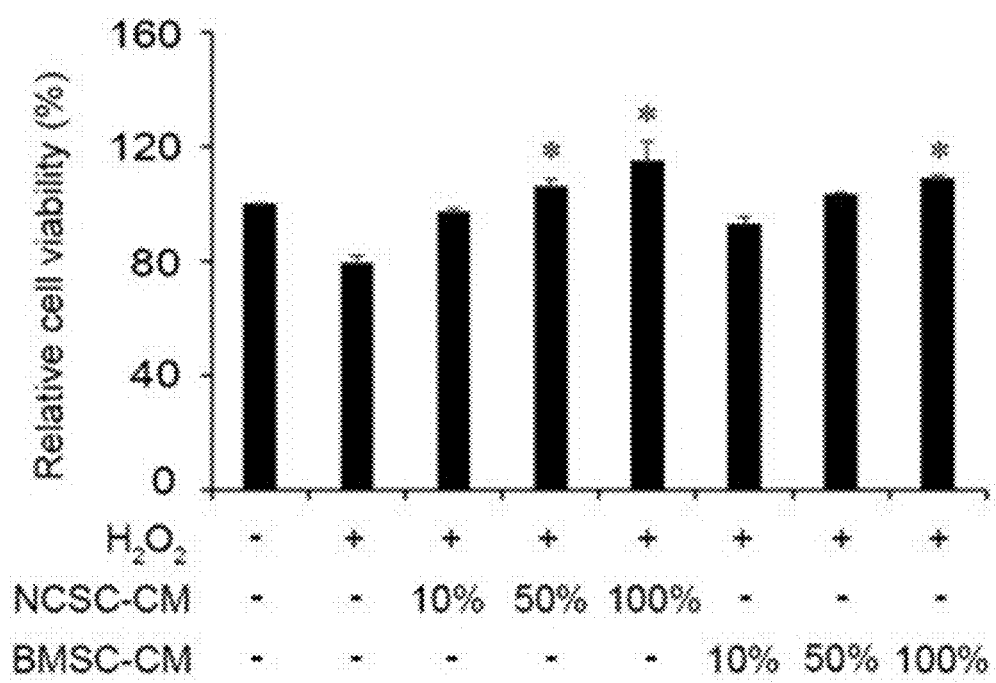

[FIG. 29]
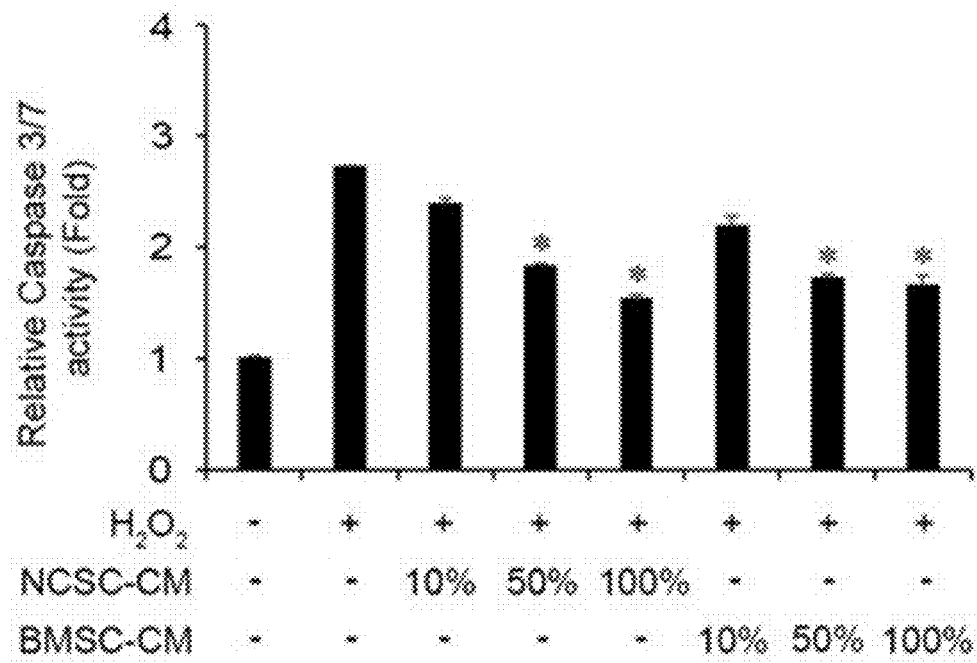
[FIG. 30]
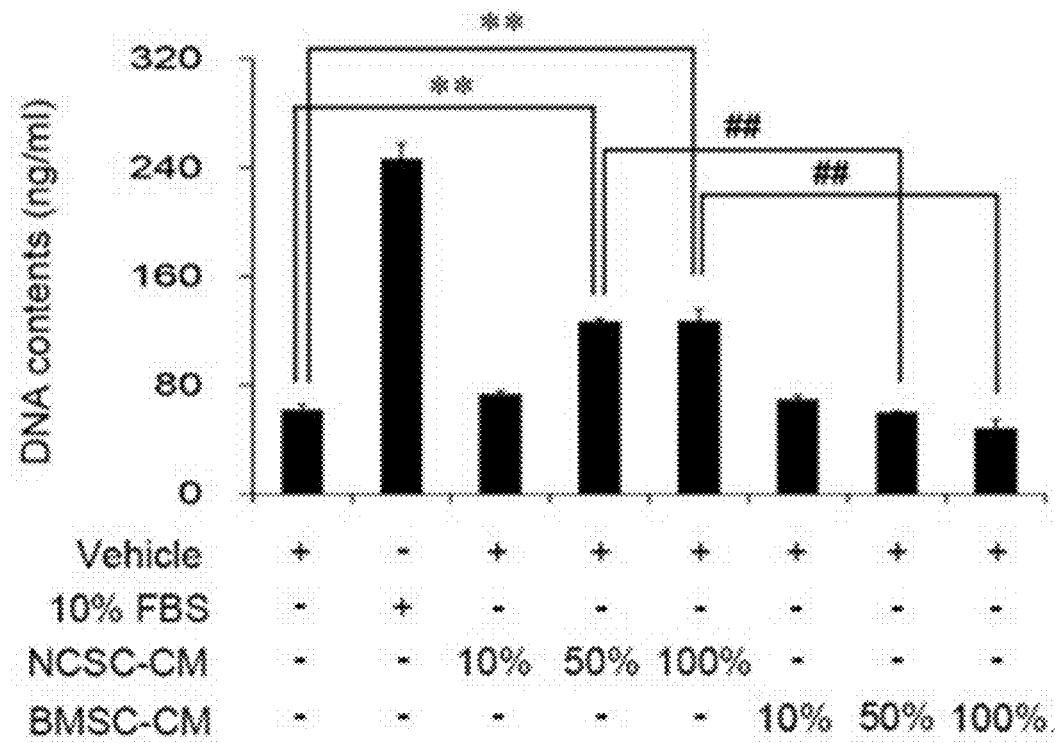

[FIG. 31]
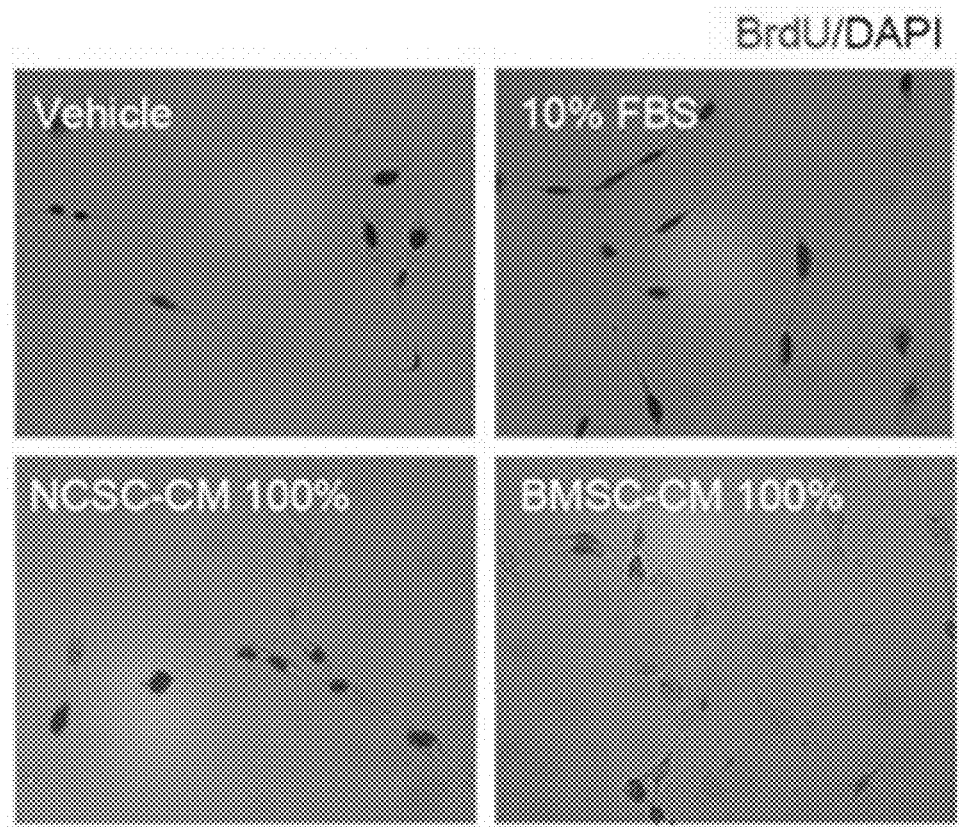

[FIG. 32]
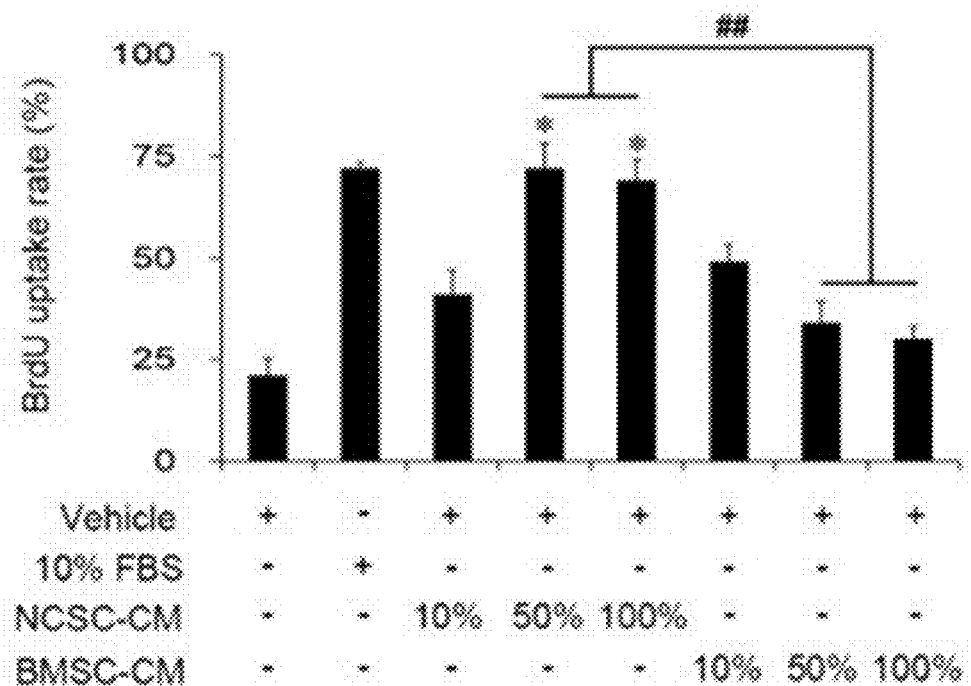
[FIG. 33]
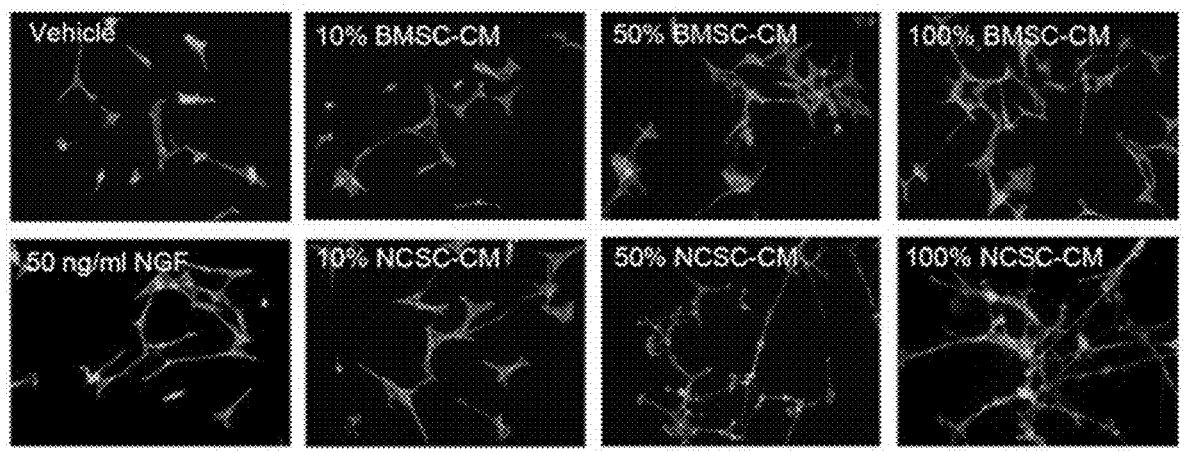

[FIG. 34]
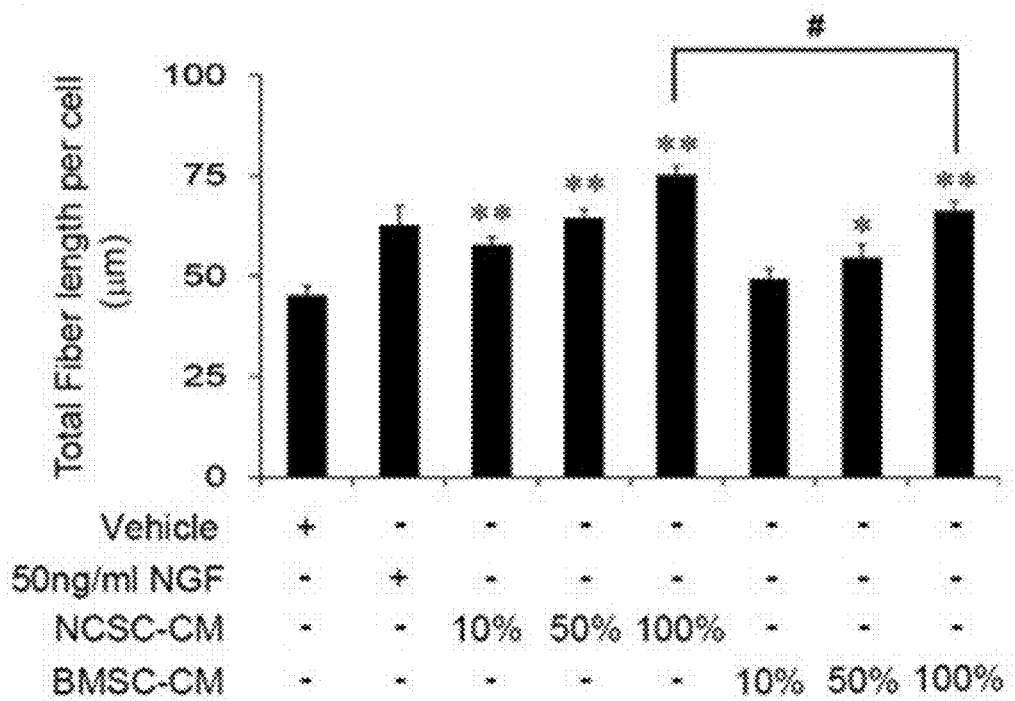
[FIG. 35]
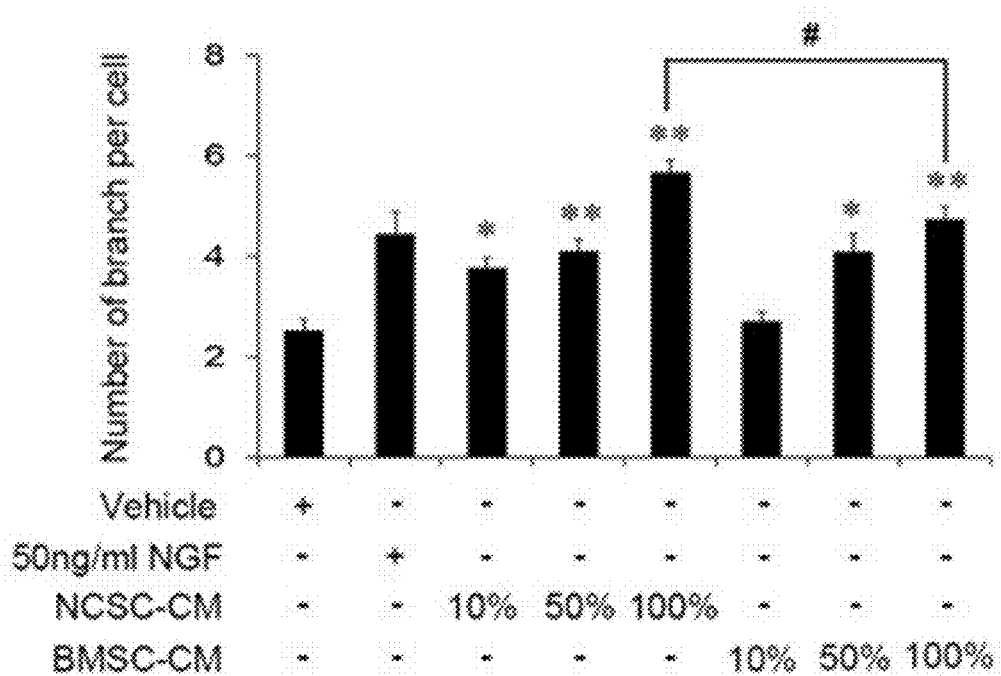

[FIG. 36]
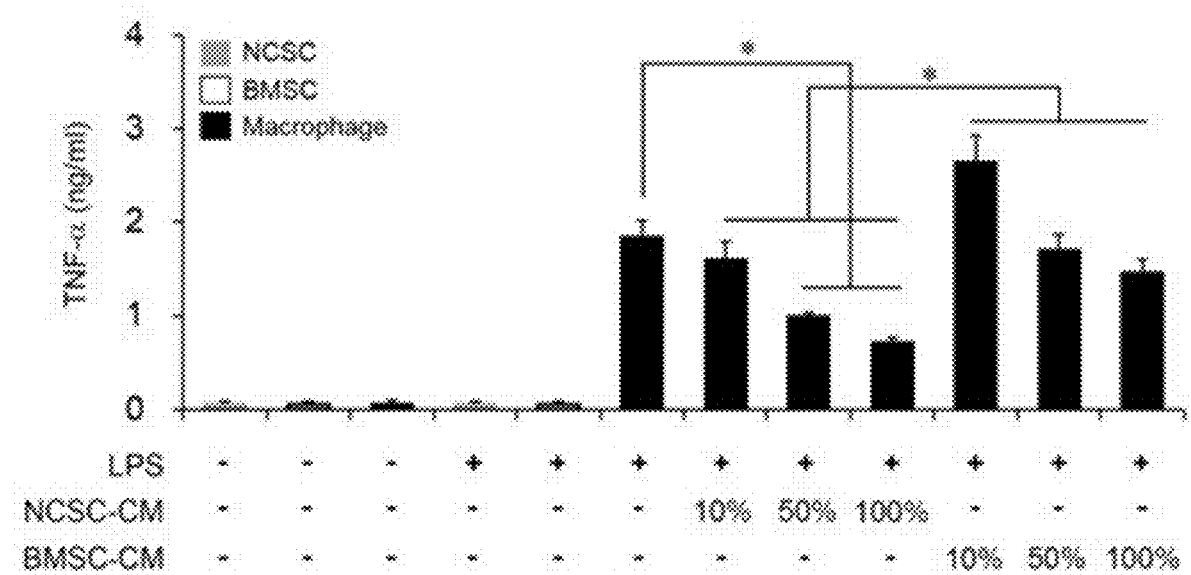
[FIG. 37]
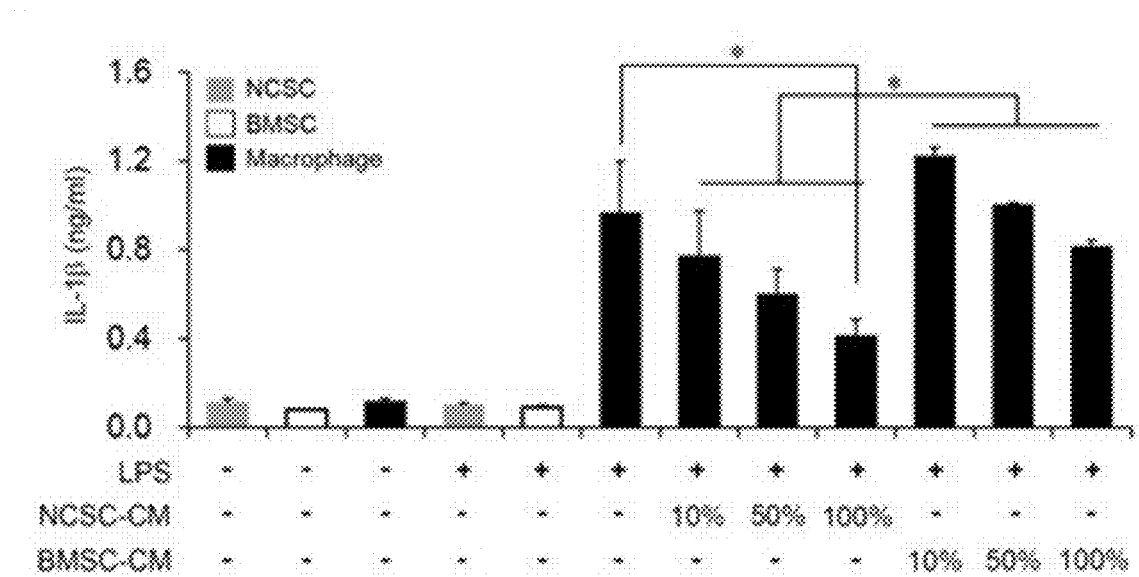

[FIG. 38]
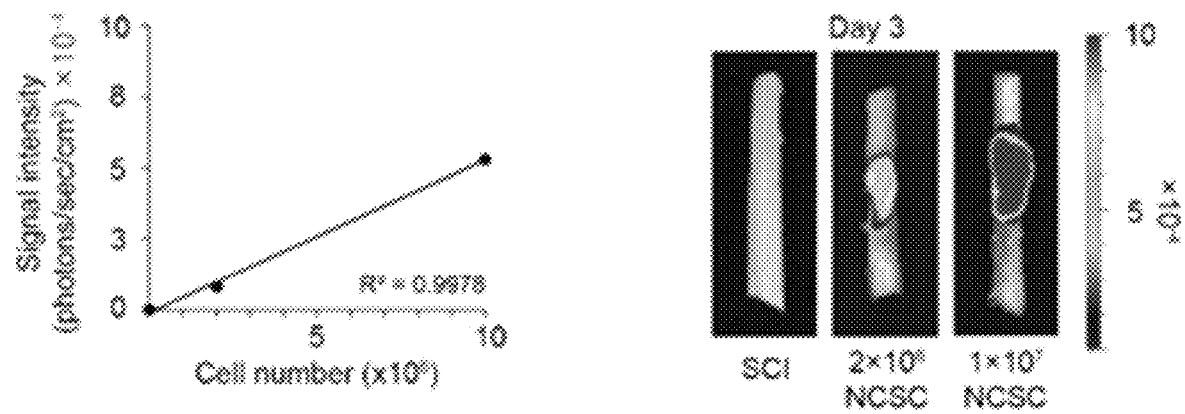
[FIG. 39]
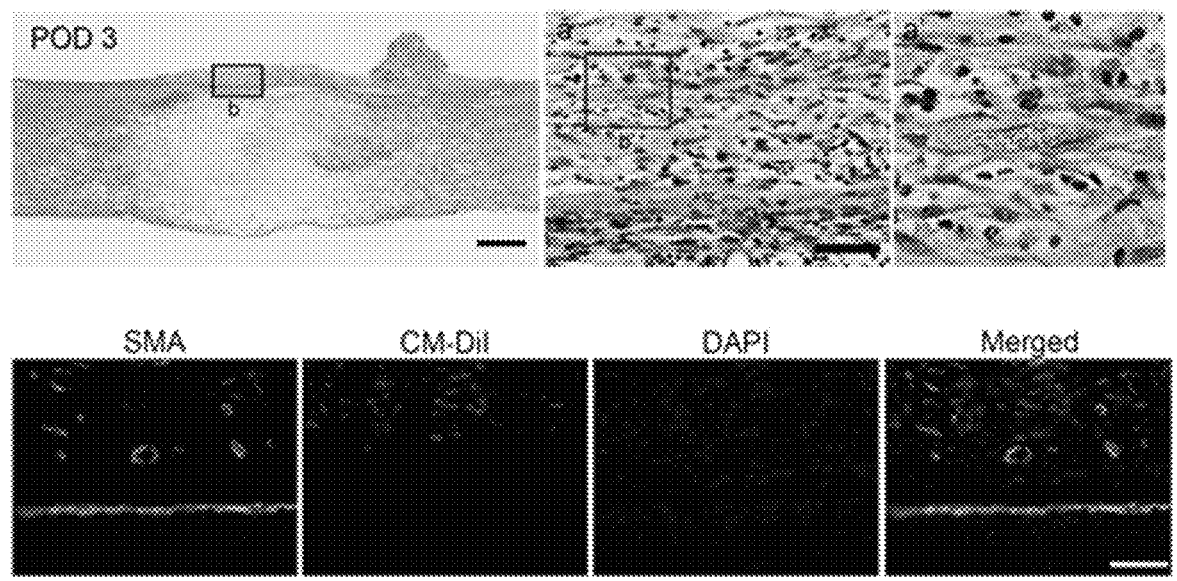

[FIG. 40]
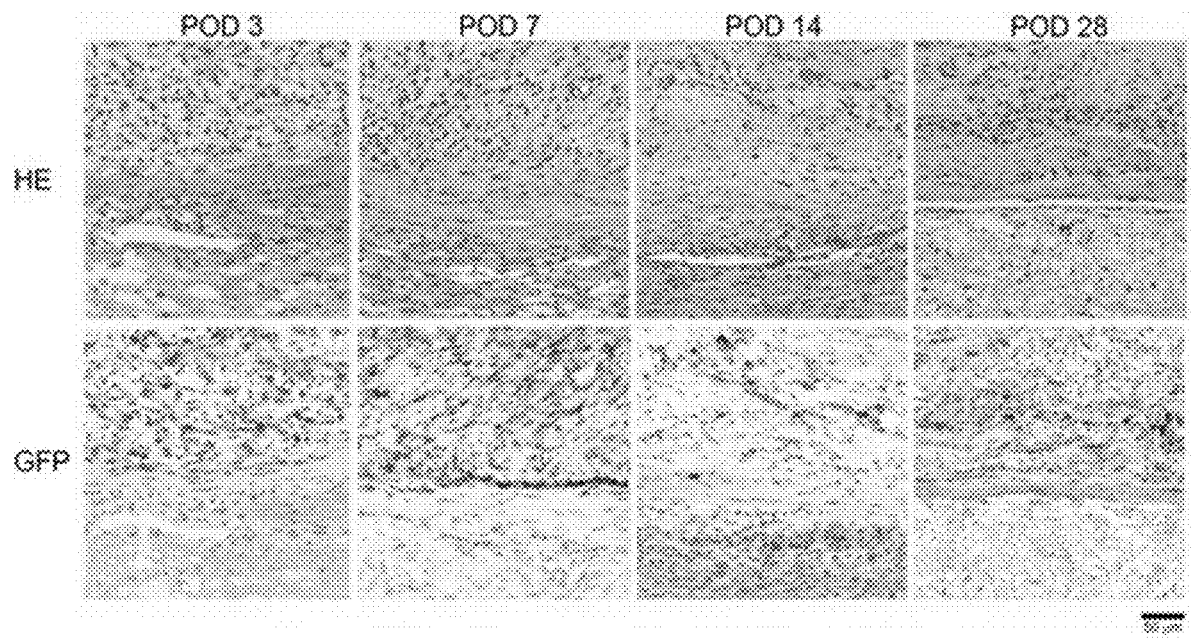
[FIG. 41]
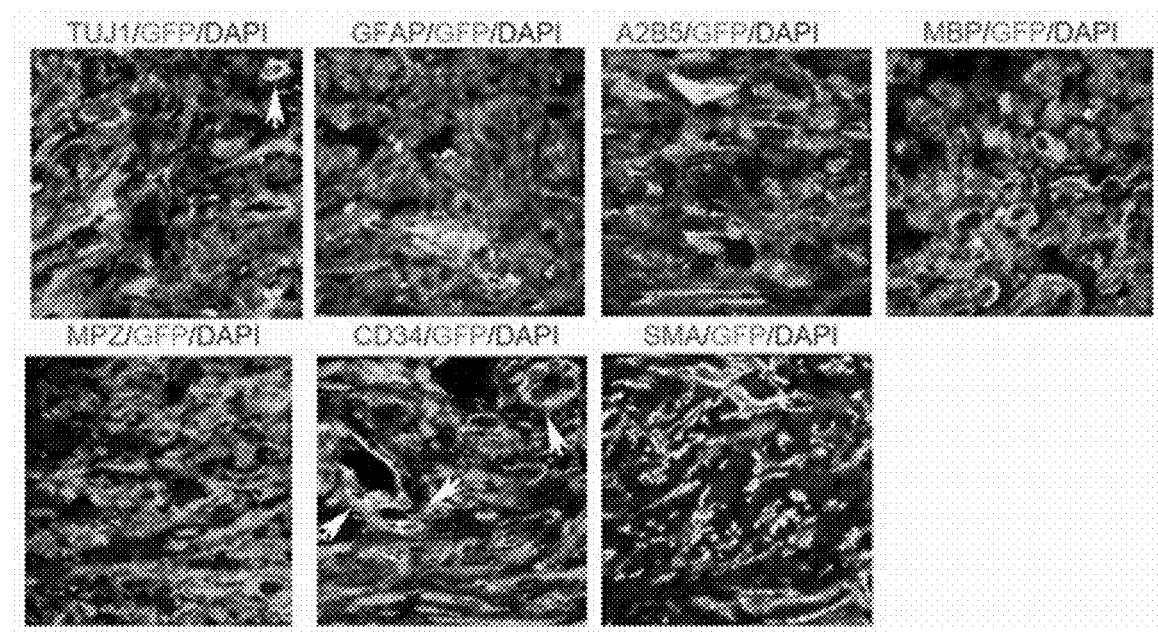

[FIG. 42]
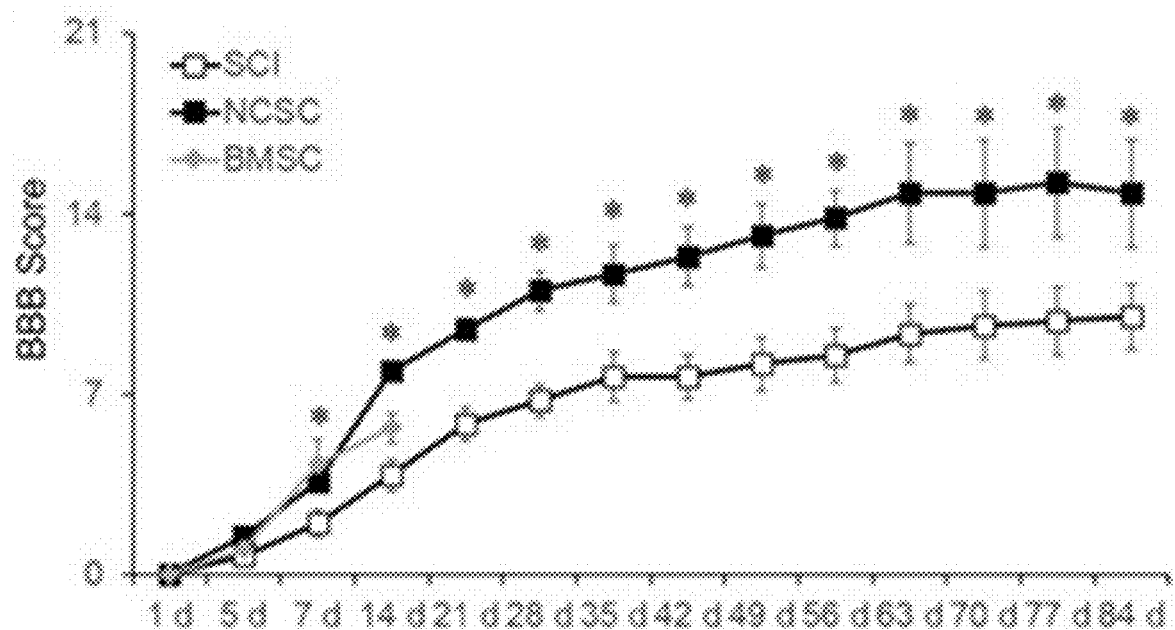
[FIG. 43]
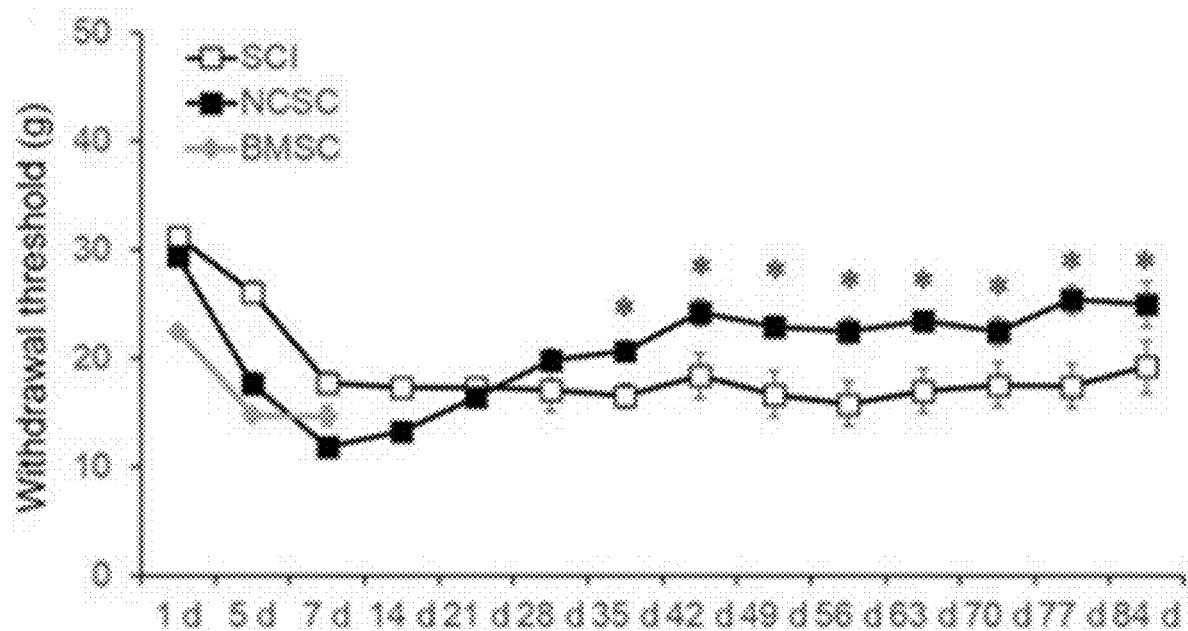

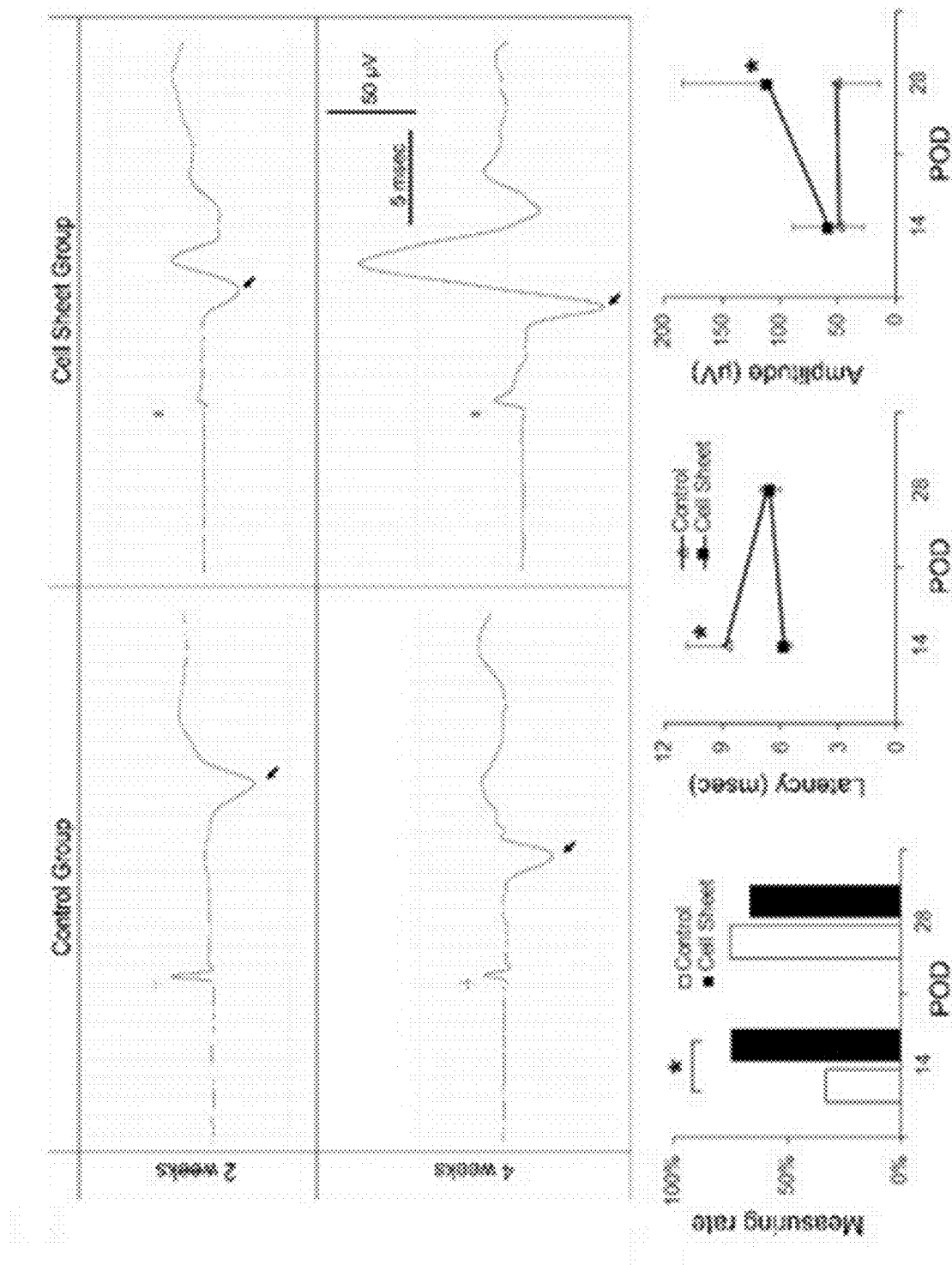
[FIG. 44]

[FIG. 45]
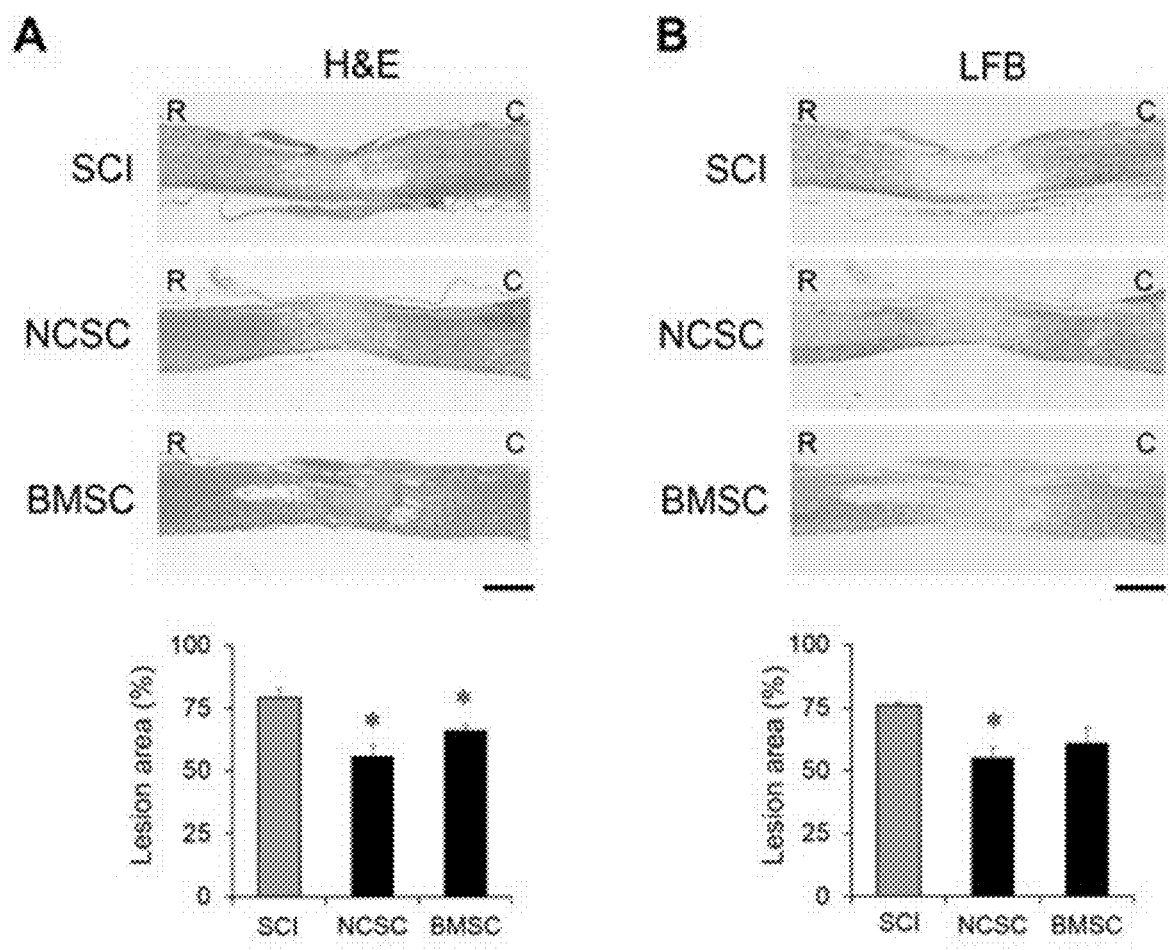

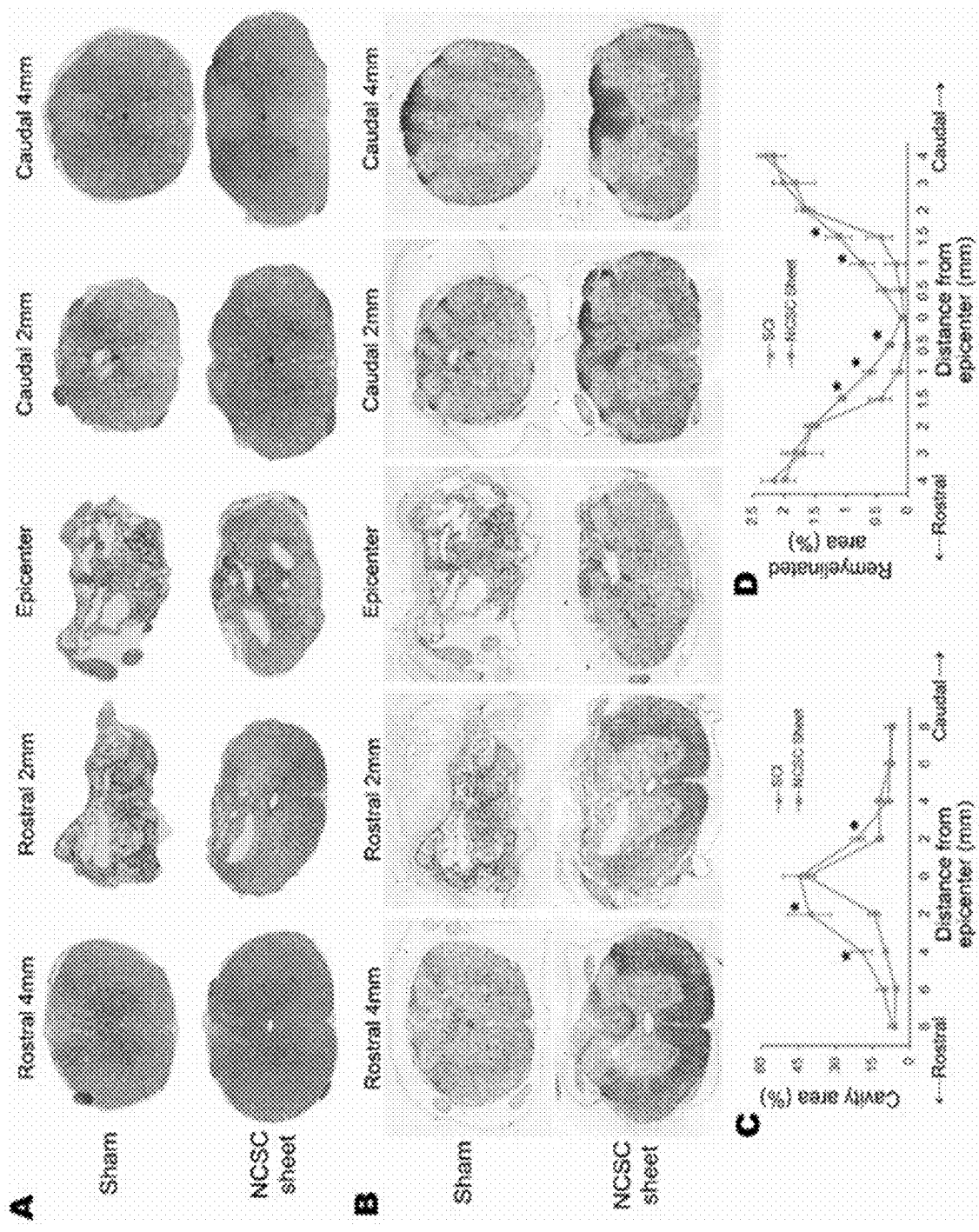
[FIG. 46]

[FIG. 47]
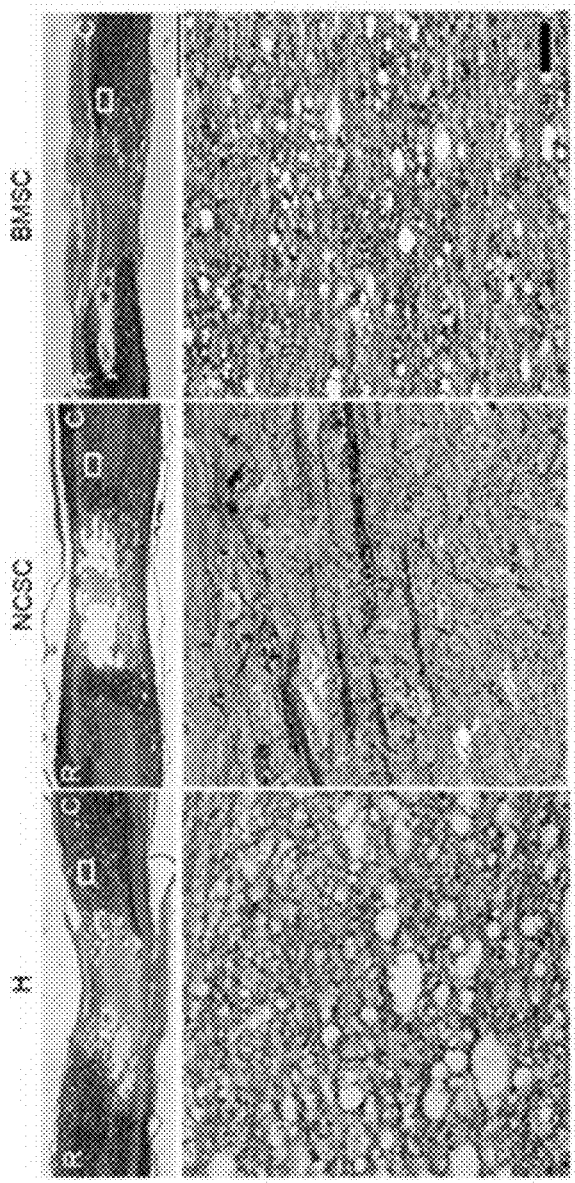
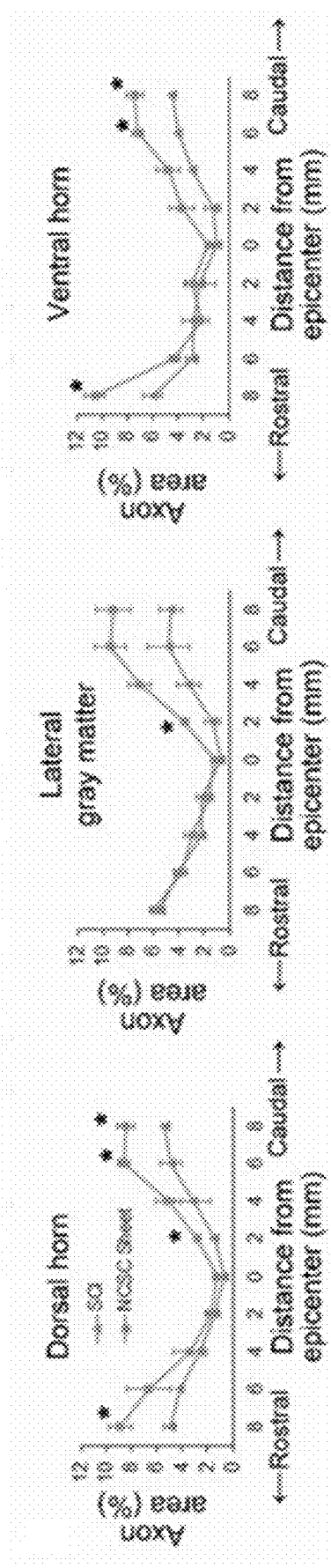

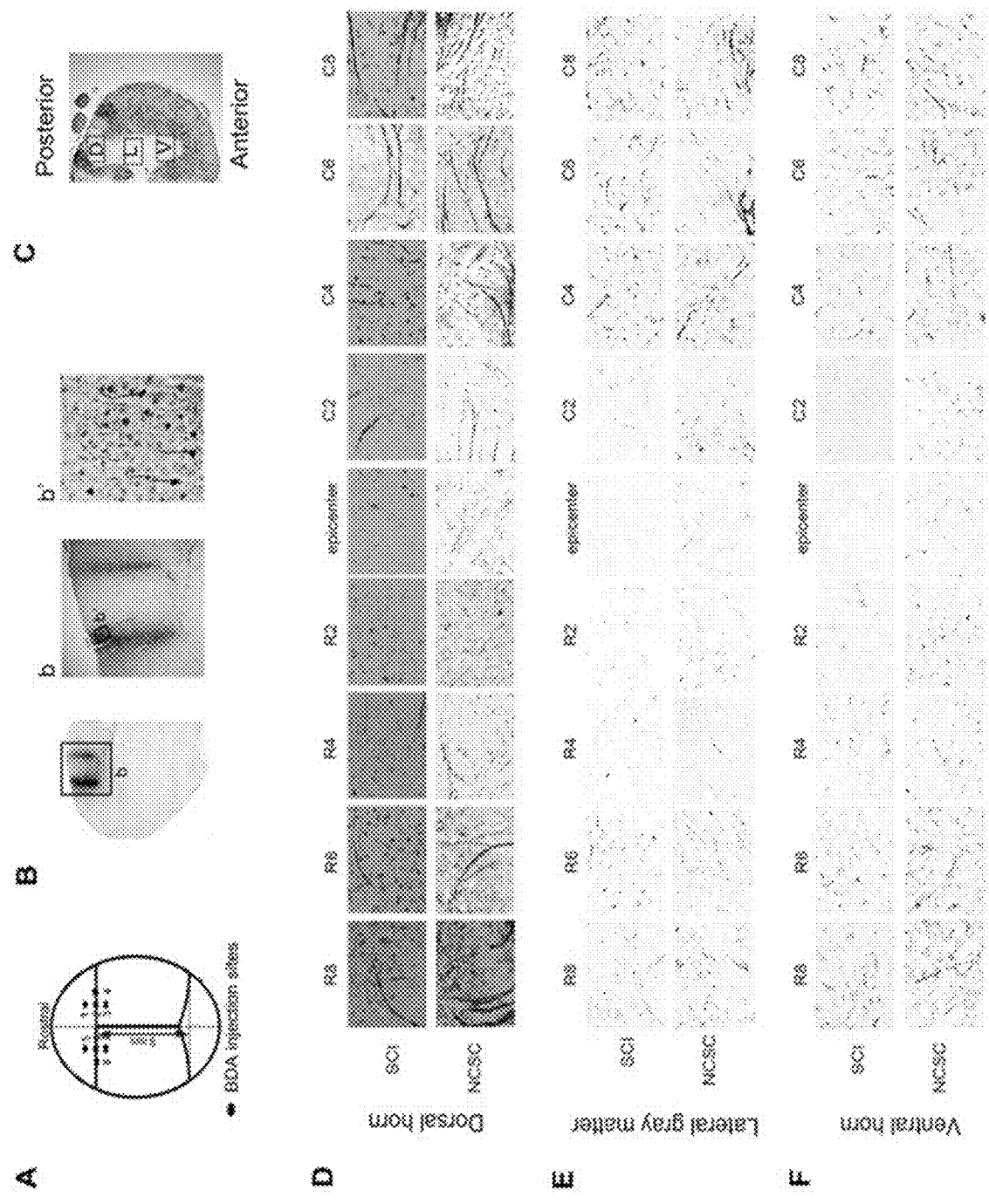
[FIG. 48]

[FIG. 49]
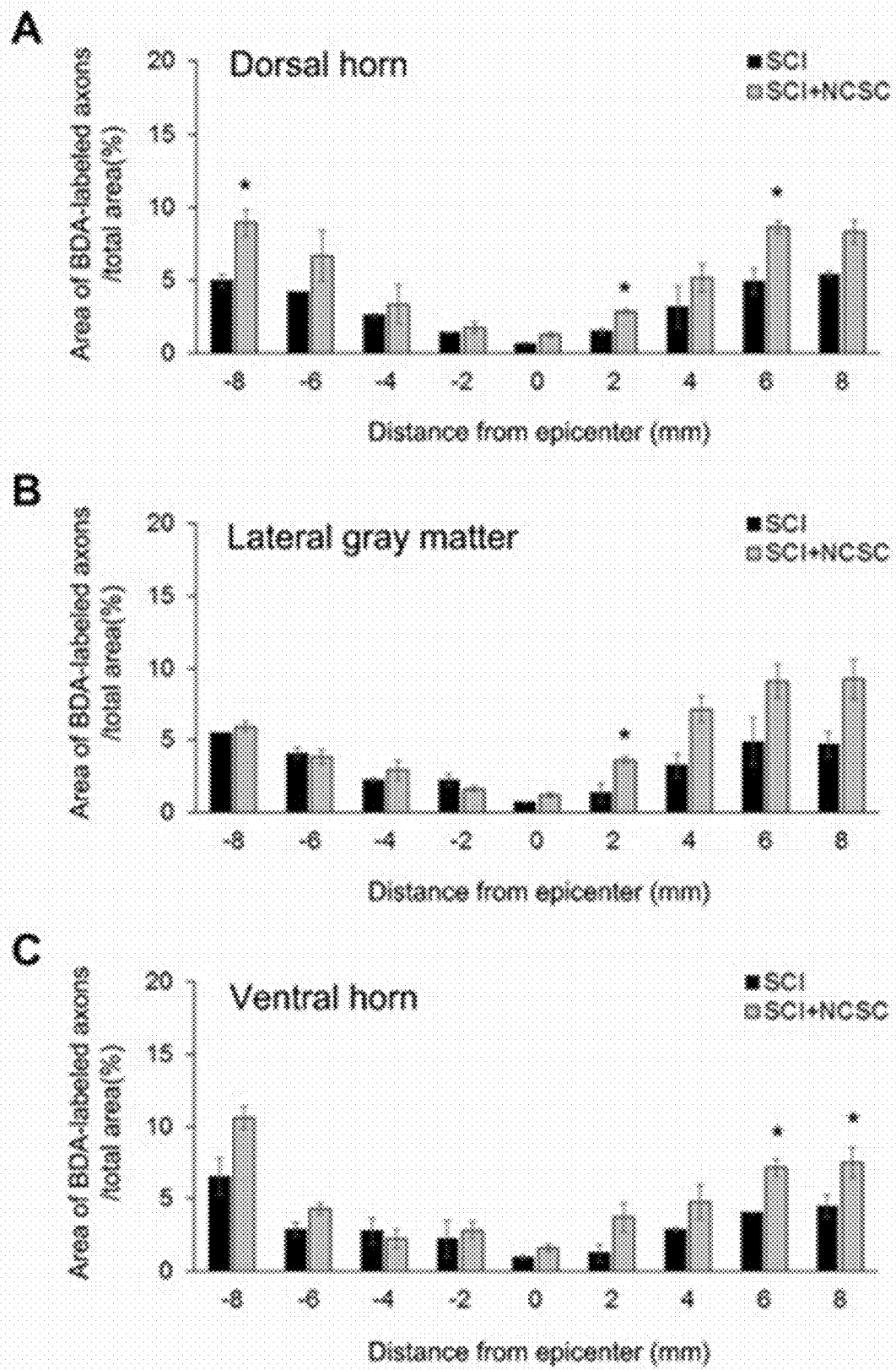

[FIG. 50]
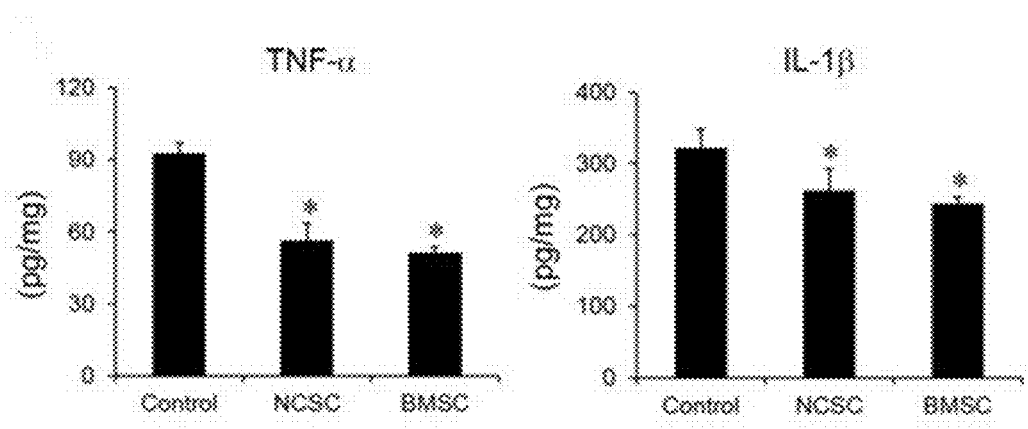

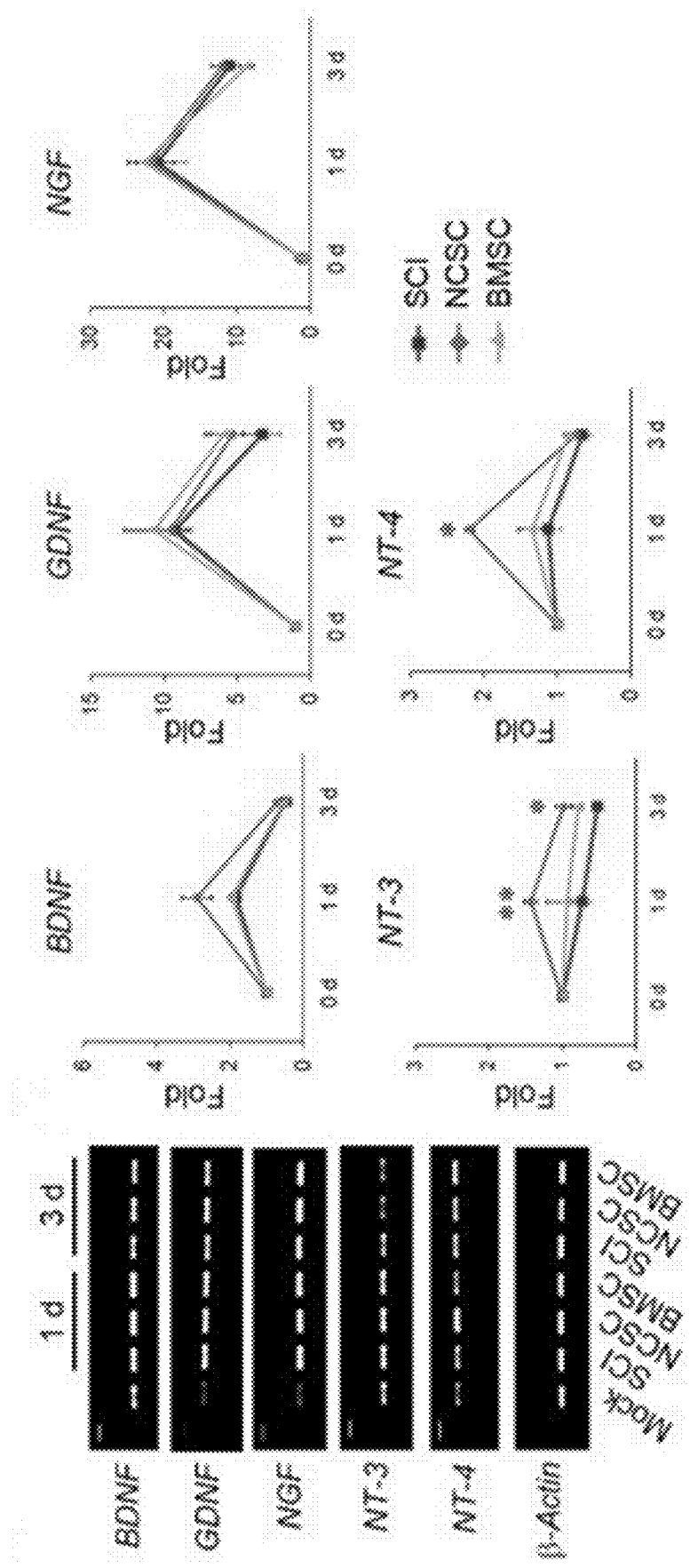
[FIG. 51]

MULTILAYERED CELL SHEET OF NEURAL CREST STEM CELLS AND METHOD OF PREPARING THE SAME

TECHNICAL FIELD

The present disclosure relates to a multilayered cell sheet of neural crest stem cells (NCSCs) derived from adult peripheral nerves and a method of preparing the multilayered cell sheet. The NCSCs derived from adult peripheral nerves are embedded in a hydrogel and then, subjected to three-dimensional culture to be formed in multiple layers, thereby preparing a multilayered cell sheet. The multilayered cell sheet can be then applicable as a therapeutic agent in spinal cord injury or brain injury.

BACKGROUND ART

Spinal cord injury (SCI) refers to a condition when abnormality occurs in normal motor function, sensation, and autonomic nerve function, due to trauma applied to the spinal cord. Unfortunately, the recovery of neurological function after SCI is limited, and most SCI patients face permanent neurological disorder in their life. Medicine treatment, decompression surgery, or the like has been suggested for the treatment of SCI. However, as the need for neuroprotective and regenerative techniques that can reduce apoptosis and secondary damages and promote production of axon and myelin, treatment methods using a cell therapy product or stem cell therapy product and a product prepared according to the stem cell therapeutics-tissue engineering have been highlighted.

Regarding the SCI treatment, hematopoietic stem cells (HSCs), mesenchymal stem cells (MSCs) derived from bone marrows, cord blood, and adipose tissue, Schwann cells (SCs), olfactory ensheathing cells (OECs), neural stem cells (NSCs), neural crest stem cells (NCSCs), and the like have been reported to be applicable in stem cell therapy for protection and regeneration of the spinal cord.

In current clinical and preclinical studies on SCI, stem cells have been injected mostly by (1) direct injection into the spinal cord, (2) injection into cerebrospinal fluid, and (3) intravenous injection. Among these injection types, due to high delivery rate of the injected cells to a damaged area, the direct injection of stem cells into the spinal cord is the most common injection type. However, such a direct injection type requires direct insertion of a needle into the spinal cord, resulting in not only additional injury caused by a syringe needle, but also additional damage in proportion to the volume of injected cells or drugs. In addition, the injected cells can be damaged by free radicals and excessive inflammatory responses in a damaged nerve tissue. Therefore, there is a need for a cell transplantation method, which can simultaneously increase a delivery rate of the injected cells to a damaged area and a survival rate of the injected cells in a damaged area.

An epidural space has been used as an injection route of various drugs since the late $19^{th}$ century, and is still currently used widely as an injection route of anesthetic and analgesics drugs for painless childbirth or the like. Drugs injected into the epidural space can be spread out to nearby tissues including the nearby spinal cord and spinal nerves, or can be absorbed by the systemic circulation of the body, thereby exhibiting functions of the drugs. A dose of about 1/10 of the drugs injected into the epidural space is enough to exhibit the same central system effect as the drugs injected by intravenous injection. Therefore, such epidural injection is one type of selectively injecting a high dose drug to the spinal nervous system without direct contact or damage to the spinal nerves. Up to date, a main mechanism of the stem cell therapy for SCI has been known to exhibit neuroprotection and regeneration effects by a substance secreted from the stem cells, rather than effects by direct cell substitution. Accordingly, the epidural injection of cells can be an effective method of delivering cellular secretions at a high concentration without direct contact and damage to the spinal nerves.

In the related art, a scaffold has been most widely used as a carrier for local delivery of a stem cell therapy product to the spinal cord. Such a scaffold can provide an extracellular matrix that is essential for the cell survival and cell functional maintenance, and in this regard, the survival rate of cells may be increased during the delivery of the cell therapy product. Here, a scaffold is made of a natural or synthetic polymer having biodegradability, i.e., being biodegradable in the living body, and is prepared in the form of hydrogel and porous sponge. A hydrogel can be easily prepared in desired shape and size as compared with a porous sponge type scaffold, and also has advantages of being able to load and deliver cells at high density. However, hydrogel has a weak physical strength so that it is difficult fix on the spinal cord, and in this regard, a hydrogel scaffold is the most widely used for the injection into the spinal cord after being mixed with a stem cell therapy product. Meanwhile, a porous sponge type scaffold is difficult to be prepared in various sizes and shapes, but is easy to control physical strength thereof. Thus, a porous sponge type scaffold is used as a carrier for transplantation of a stem cell therapy product into the spinal cord. However, a porous sponge type support is difficult to deliver cells at high density, and disadvantages that a porous sponge type support induces foreign and inflammatory responses upon a cross-linking reaction made for the purpose of improving physical properties have been suggested.

To address the problems that the scaffold has during the delivery of a stem cell therapy product, a technique of producing a stem cell therapy product in the form of a cellular sheet for local delivery in the living body has been reported. In the related art, to prepare a multilayered cell sheet, a method of preparing a multilayered cell sheet was proposed, the method including: preparing a single-layered cell sheet first; and stacking the prepared single-layered cell sheet in multiple layers by using a pipette, a supporting membrane, or a special manipulator. However, when prepared a five-layered or more layered cell sheet, the stacking of the single-layered cell sheet caused a problem that the supply of oxygen and nutrients to the inside of the cell sheet is limited when stacking the single-layered cell sheets in five or more layers, resulting in the occurrence of cell damage. Consequently, it was found that only a multilayered cell sheet consisting of less than five layers had biological effectiveness. The stacking of the single-layered cell sheet can be performed by layering a three-layered cell sheet four times at intervals of five days. However, the total time required for the preparation will be more than 20 days, and the biological properties of constituent cells within a cell sheet may be changed. In addition, after angiogenesis is induced within a three-layered cell sheet transplanted in the living body, the multilayered cell sheet may obtain therapeutic effects only through repeated transplantation processes. That is, when a thick cell sheet is prepared by a technique known to date, there may be a safety problem since a lot of time and a special culture container and a manipulator are required, and if each process of the preparation is not carefully manipulated, a resulting cell sheet may be damaged and more likely to have a chance of contamination during attachment and/or detachment and movement of the cell sheet, as compared with a process of single incubation.

DETAILED DESCRIPTION OF THE INVENTION

Technical Problem

The present disclosure provides a method of manufacturing a multilayered cell sheet according to a single step culture procedure by using, as a three-dimensional scaffold, a biodegradable natural polymer hydrogel and embedding peripheral nerve (PN)-derived neural crest stem cells (NCSCs) in the hydrogel.

In addition, the present disclosure provides a multilayered cell sheet of NCSCs, the multilayered cell sheet including: a hydrogel in which the NCSCs are embedded; and extracellular matrix (ECM), angiogenic factors, anti-inflammatory factors, neuroprotective factors, and neurotrophic factors that are secreted from the NCSCs and accumulated in the hydrogel.

In addition, the present disclosure provides a composition for treating spinal cord injury, a composition for treating brain injury, or a composition for treating peripheral nerve injury, wherein each composition includes, as an active ingredient, a multilayered cell sheet of NCSCs or a culture product of the multilayered cell sheet of the NCSCs.

Technical Solution

To achieve the above technical problems, the present disclosure provides a method of manufacturing a multilayered cell sheet of neural crest stem cells (NCSCs), the method including steps of: (1) isolating and culturing NCSCs; (2) embedding the cultured NCSCs in a hydrogel; (3) culturing the hydrogel comprising the NCSCs embedded therein under stressed culture conditions in which a physical support is applied to prevent cell-mediated hydrogel compactions; and (4) culturing the resulting hydrogel of step (3) under non-stressed culture conditions in which a physical support is excluded to induce cell-mediated hydrogel compaction.

In addition, the present disclosure provides a multilayered cell sheet of NCSCs, the multilayered cell sheet including: a hydrogel in which the NCSCs are embedded; and extracellular matrix (ECM), angiogenic factors, anti-inflammatory factors, neuroprotective factors, and neurotrophic factors that are secreted from the NCSCs and accumulated in the hydrogel.

In addition, the present disclosure provides a composition for treating spinal cord injury, the composition including, as an active ingredient, the multilayered cell sheet of the NCSCs or a culture product of the multilayered cell sheet of the NCSCs.

In addition, the present disclosure provides a composition for treating brain injury, the composition including, as an active ingredient, the multilayered cell sheet of the NCSCs or a culture product of the multilayered cell sheet of the NCSCs.

In addition, the present disclosure provides a composition for treating peripheral nerve injury, the composition including, as an active ingredient, the multilayered cell sheet of the NCSCs or a culture product of the multilayered cell sheet of the NCSCs.

Advantageous Effects of the Invention

The present disclosure relates to a multilayered cell sheet of neural crest stem cells (NCSCs) and a method of manufacturing the same. In particular, the present disclosure provides a method of manufacturing a multilayered cell sheet according to a single step culture procedure by using, as a three-dimensional scaffold, a biodegradable natural polymer hydrogel and embedding peripheral nerve (PN)-derived NCSCs in the hydrogel. The present disclosure is aimed to provide a novel method of manufacturing a multilayered cell sheet of NCSCs, the method capable of preventing a sheet damage problem and a risk of sheet contamination, which are caused by physical vulnerability during the conventional manufacturing of the multilayered cell sheet, and shortening the manufacturing time by changing a multi-step culture process to a single step culture procedure. Furthermore, the multilayered cell sheet of NCSCs of the present disclosure may enhance physical characteristics through cell-to-cell adhesion and cell-to-hydrogel polymer adhesion, and also enhance biological functions by accumulating bioactive factors and extracellular matrix (ECM), which are produced and secreted from NCSCs during cell culturing, in the multilayered cell sheet. The multilayered cell sheet of the present disclosure does not require any special device for the manufacturing, is manageable with good physical characteristics, increases a cell survival rate after transplantation based on sufficient accumulation of various growth and protective factors and extracellular matrix between cells, and is also thin due to cell-induced contraction, making nutrient transfer easy. In this regard, the multilayered cell sheet of the present disclosure is considered to be mostly compensated for the disadvantages of the existing cellular sheet.

DESCRIPTION OF THE DRAWINGS

FIG. 1 shows a process of isolating peripheral nerve-derived neural crest stem cells (PN-NCSCs) by using a 3-dimensional collagen hydrogel-supported organ culture method.

FIG. 2 shows time-dependent migration and outgrowth of the PN-NCSCs in the collagen hydrogel from embedded PNs.

FIG. 3 shows the results of comparing the colony-forming ability of the PN-NCSCs with that of BMSCs, wherein the PN-NCSCs are obtained by selective degradation of the collagen hydrogel.

FIG. 4 is a graph showing the degree of colony formation by the PN-NCSCs and BMSCs.

FIG. 5 is a graph showing population doubling time of the PN-NCSCs and cumulative population doubling level of the PN-NCSCs.

FIG. 6 shows the results of comparing the neural crest cells-specific immunophenotypic characteristics of the PN-NCSCs with those of PC12 cells and BMSCs.

FIG. 7 shows the results of comparing the PN-NCSCs with PC12 cells and BMSCs to indicate that the PN-NCSCs have no immunophenotypic characteristics that are specific to differentiated neurons and neuroglial cells.

FIG. 8 shows the results of comparing the stromal cell-specific immunophenotypic characteristics of the PN-NCSCs with those of PC12 cells and BMSCs.

FIG. 9 shows the results of comparing the PN-NCSCs with PC12 cells and BMSCs to indicate that the PN-NCSCs have no immunophenotypic characteristics that are specific to vascular endothelial cells or hematopoietic cells.

FIG. 10 shows the results of comparing the embryonic neural crest cells-specific mRNA expression of the PN-NCSCs with those of PC12 cells and BMSCs.

FIG. 11 shows the results of comparing the PN-NCSCs with BMSCs to indicate that the PN-NCSCs have immunophenotypic characteristics that are specific to neurons and neuroglial cells after a neurosphere is formed and differentiation thereof is induced to confirm the differentiation potential of the PN-NCSCs into neuroglial cells of the in vitro nervous system.

FIG. 12 shows the results of differentiation of the PN-NCSCs into adipocytes and osteoblasts based on accumulation of lipids in cytoplasm and extracellular mineral deposition after differentiation of the PN-NCSCs is induced to confirm the in vitro multipotent capability of the PN-NCSCs FIG. 13 shows the results of comparing hydrogel compositions for three-dimensional distribution and culture of the PN-NCSCs.

FIG. 14 shows mRNA expression rates of urokinase-type plasminogen activator and tissue plasminogen activator that mediate fibrinolysis of the PN-NCSCs.

FIG. 15 shows the results of comparing hydrogel compositions for three-dimensional culture of the PN-NCSCs.

FIG. 16 shows the results of comparing the three-dimensional distribution of cells according to a hydrogel composition including the PN-NCSCs embedded therein.

FIG. 17 shows the results of comparing cell apoptosis according to the three-dimensional culture environment of the PN-NCSCs.

FIG. 18 shows the results of comparing cell-to-cell adhesions according to the cell density of the PN-NCSCs in a collagen/fibrin hydrogel under an adhesion environment.

FIG. 19 shows the cell layer number of a multilayered cell sheet according to the number of cells of the PN-NCSCs that are to be embedded into a hydrogel.

FIG. 20 shows the results of fibril condensation and water extrusion in a multilayered cell sheet of the PN-NCSCs according to the suspension culture time.

FIG. 21 shows accumulation of newly synthesized extracellular matrices (e.g., fibronectin, laminin, and collagen type IV) by PN-NCSCs during culturing in a multilayered cell sheet of the PN-NCSCs.

FIG. 22 shows accumulation of angiogenic factors in a multilayered cell sheet of the PN-NCSCs evidenced by their mRNAs expression.

FIG. 23 shows accumulation of anti-inflammatory factors in a multilayered cell sheet of the PN-NCSCs evidenced by their mRNAs expression.

FIG. 24 shows accumulation of neuroprotective factors in a multilayered cell sheet of the PN-NCSCs evidenced by their mRNAs expression.

FIG. 25 shows accumulation of neurotrophic factors in a multilayered cell sheet of the PN-NCSCs evidenced by their mRNAs expression.

FIG. 26 shows accumulation of neurotrophic factors in a multilayered cell sheet of the PN-NCSCs evidenced by their mRNAs expression.

FIG. 27 shows cell-to-cell binding by beta-catenin) and cell-to-extracellular matrix binding by CD29 in a multilayered cell sheet of the PN-NCSCs FIG. 28 shows the results of comparing the cell survival of the PN-NCSCs with BMSCs after treating SH-SY5Y cells, which are treated with hydrogen peroxide to confirm the neuroprotective effect of the PN-NCSCs, with the conditioned media of the PN-NCSCs at different concentrations.

FIG. 29 shows the results of comparing the inhibitory effect of caspase 3 and caspase 7, which are apoptosis factors, with that of BMSCs after treating SH-SY5Y cells, which are treated with hydrogen peroxide to confirm the neuroprotective effect of the PN-NCSCs, with the conditioned media of the PN-NCSCs at different concentrations.

FIG. 30 shows the degree of proliferation of SH-SY5Y cells in terms of DNA concentrations by treating the SH-SY5Y cells with the conditioned media of the PN-NCSCs at different concentrations, thereby confirming the neurotrophic effect of the PN-NCSCs.

FIG. 31 shows the immunostaining results using BrdU antibodies compared with BMSCs, thereby confirming SH-SY5Y cells that are renewed using the conditioned media of the PN-NCSCs.

FIG. 32 is a graph showing the results of FIG. 21.

FIG. 33 shows the results of comparing an increase of neurite outgrowth of SH-SY5Y cells with NGF or BMSC, wherein the SH-SY5Y cells are treated with the conditioned media of the PN-NCSCs at different concentrations to confirm that SH-SY5Y cells promote the formation of neurites and synapse of the PN-NCSCs.

FIG. 34 shows the results of comparing a neurite length of SH-SY5Y cells, which are treated with the conditioned media of the PN-NCSCs, with that of NGF or BMSC.

FIG. 35 shows the results of comparing a degree of neurite connectivity of SH-SY5Y cells, which are treated with the conditioned media of the PN-NCSCs, with that of NGF or BMSC.

FIG. 36 shows the inhibitory effect of conditioned media of PN-NCSCs or BMSCs on the TNF-α secretion level by activated macrophages, indicating the inhibitory effect of the PN-NCSCs on inflammation.

FIG. 37 shows the inhibitory effect of conditioned media of PN-NCSCs or BMSCs on the secretion level of IL-1β by activated macrophages, indicating the inhibitory effect of PN-NCSCs on inflammation.

FIG. 38 is a molecular image showing retention rates of PN-NCSCs transplanted as a multilayered cell sheet or single cell suspension of the PN-NCSCs on the third day after transplantation multilayered cell sheet into a spinal cord injury rat, wherein the image indicates a substantial increased retention rate in rats transplanted by multilayered cell sheet compared to single cell suspension of the PN-NCSCs.

FIG. 39 shows secure attachment between a multilayered cell sheets of the PN-NCSCs implanted into a spinal cord injury rat and the spinal cords, and vascular ingrowth into multilayered cell sheets from spinal cords.

FIG. 40 shows the survival of a multilayered cell sheet of the PN-NCSCs implanted into a spinal cord injury rat at the $3^{rd}$, $7^{th}$, $14^{th}$, and $28^{th}$ day after implantation.

FIG. 41 shows the in situ differentiation of a transplanted multilayered cell sheet of the PN-NCSCs to fibroblasts and vascular endothelial cells, wherein the multilayered cell sheet is transplanted on the dura mater of the injured spinal cord.

FIG. 42 shows the recovery of motor function of a spinal cord injury rat to which a multilayered cell sheet of the PN-NCSCs is transplanted.

FIG. 43 shows the recovery of sensory function of a spinal cord injury rat to which a multilayered cell sheet of the PN-NCSCs is transplanted.

FIG. 44 shows the recovery of motor evoked potential of a spinal cord injury rat to which a multilayered cell sheet of the PN-NCSCs is transplanted.

FIG. 45 shows the regenerative ability of a multilayered cell sheet of the PN-NCSCs transplanted into the injured spinal cords at the $2^{nd}$ weeks of the injury.

FIG. 46 shows the regenerative ability of a multilayered cell sheet of the PN-NCSCs transplanted into the injured spinal cords at the $4^{th}$ weeks of the injury.

FIG. 47 shows the results that a multilayered cell sheet of the PN-NCSCs transplanted on the injured spinal cords exhibits axon regeneration at the $2^{nd}$ weeks of the transplantation assessed by the morphometry using Bodian's silver staining.

FIG. 48 shows the recovery degree of neural circuits by a multilayered cell sheet of the PN-NCSCs transplanted on the injured spinal cords at the $4^{th}$ weeks of the transplantation assessed by anterograde neural tracing.

FIG. 49 shows the density of axon regrowth in the epicenter of the injured spinal cords implanted with or without a multilayered cell sheet of the PN-NCSCs at the $4^{th}$ weeks of the transplantation assessed by anterograde neural tracing.

FIG. 50 shows the inhibitory effect of a multilayered cell sheet of the PN-NCSCs on inflammatory response in the injured spinal cord assessed by on the secretory level of TNF-α and IL-1β according to the transplantation of a wherein the multilayered cell sheet on the injured spinal cords.

FIG. 51 shows the results that the expression level of neurotrophic mRNAs is significantly increased in injured spinal cords implanted with a multilayered cell sheet of the PN-NCSCs compared to the spinal cord transplanted with a multilayered cell sheet of the BMSC.

BEST MODE

Thus, the inventors of the present disclosure have attempted to improve the time and complicated process required in the manufacturing of a thick multilayered cell sheet according to a method known to date, and to prevent various limitations including laborious process, the need for specialized equipment to stack a single layered cell sheet, mechanical fragility, and contamination. The present disclosure provides a method of manufacturing a multilayered cell sheet according to a single step culture procedure by using, as a three-dimensional scaffold, a biodegradable natural polymer hydrogel and embedding peripheral nerve (PN)-derived NCSCs in the hydrogel. The present disclosure is aimed to provide a novel method of manufacturing a multilayered cell sheet of NCSCs, the method capable of preventing a sheet damage problem and a risk of sheet contamination, which are caused by physical vulnerability during the conventional manufacturing of the multilayered cell sheet, and shortening the manufacturing time by changing a multi-step culture process to a single-step culture process. Furthermore, the multilayered cell sheet of NCSCs of the present disclosure may enhance physicomechanical property through cell-to-cell adhesion and cell-to-hydrogel polymer adhesion, and also enhance biological functions by accumulating bioactive factors and extracellular matrix (ECM), which are produced and secreted from NCSCs during cell culturing, in the multilayered cell sheet. The present disclosure has been accomplished according to a method of enhancing regeneration and protection of the spinal cord by increasing a delivery rate, a retention rate, and an engraftment rate of a stem cell-based therapeutics via delivery to the injured spinal cord.

The present disclosure provides a method of manufacturing a multilayered cell sheet of neural crest stem cells (NCSCs), the method including steps of: (1) isolating and culturing NCSCs; (2) embedding the cultured NCSCs in a hydrogel; (3) culturing the hydrogel comprising the NCSCs embedded therein under a stressed culture condition in which a physical support is applied; and (4) culturing the resulting hydrogel of step (3) under a non-stressed culture condition in which a physical support is excluded.

Preferably, the NCSCs may be isolated from peripheral nerves (PNs), but embodiments of the present disclosure are not limited thereto.

Preferably, in step (2), the cultured NCSCs may be mixed with a hydrogel in a solution phase, and the solution phase converts to a gel phase so that the NCSCs may be uniformly distributed in a three-dimensional manner in the hydrogel. Preferably, such a phase transition from the solution phase to the gel phase may be controlled in about 30 seconds to about 10 minutes.

Preferably, the hydrogel may be a natural polymer or a synthetic polymer, and examples thereof include fibrin, collagen, gelatin, chitosan, PLLA, PEG, peptide, and the like. However, embodiments of the present disclosure are not limited thereto. A polymer content in a three-dimensional hydrogel may be in a range of about 0.1% to about 5%, and preferably, may be less than about 0.5%.

More preferably, the hydrogel may be a mixed hydrogel of collagen and fibrinogen, and such a mixed hydrogel of collagen and fibrinogen may include collagen at a final concentration in a range of about 0.1% to about 1% and fibrinogen at a final concentration in a range of about 0.1% to about 1%.

In one embodiment, the hydrogel of the present disclosure may be a mixed hydrogel of collagen having a low elastic modulus and fibrin having a high elastic modulus, thereby preventing the phenomenon that the hydrogel is detached from a culture container (e.g., mold) due to cell-mediated contraction during stress culture condition (e.g., attachment culture condition).

Preferably, the cultured NCSCs of step (2) may be added in a mixed solution of thrombin and collagen, but embodiments of the present disclosure are not limited thereto.

Preferably, the cultured NCSCs of step (2) may have a density in a range of about $1\times10^6$/ml to about $1\times10^8$/ml, but embodiments of the present disclosure are not limited thereto.

More preferably, to control the number of cell layers in the multilayered cell sheet of the NCSCs, NCSCs at a density in a range of about $1\times10^6$/ml to about $1\times10^8$/ml may be mixed with a hydrogel in a solution phase, and the mixed hydrogel may be transferred at a volume in a range of about 100 μl/mm² to about 500 μl/mm² to a mold having a specific shape. Through polymerization/crosslinking at a temperature of 37° C. for 2 hours, the phase of the hydrogel is changed to a gel phase, and accordingly, the NCSCs may be uniformly distributed in a three-dimensional manner. More preferably, NCSCs at a density in a range of about $2.5\times10^6$/ml to about $1\times10^7$/ml were mixed and transferred at a volume in a range of about 150 μl/mm² to about 250 μl/mm², thereby manufacturing a multilayered cell sheet of the NCSCs. Here, by controlling the cell density and volume, a multilayered cell sheet consisting of about 10 layers to about 50 layers may be manufactured.

Preferably, the stressed culture condition of step (3) in which the physical support is applied may include casting the hydrogel comprising the NCSCs embedded therein on a circular, rectangular, or square mold so that the NCSCs are cultured under a condition in which a physical support is applied.

Preferably, the stressed culture condition of step (3) may induce cell-to-cell adhesion and cell-to-hydrogel polymer adhesion. When cultured under the stressed culture condition for 1 day to 5 days, the cells embedded in the hydrogel may be adhered to fibrillary chains of the hydrogel, and may also induce cytoplasmic spreading, cell migration, and cell-to-cell adhesion, thereby improving physical characteristics of the manufactured multilayered cell sheet.

Preferably, according to the culture under the stressed culture condition of step (3), extracellular matrix (ECM), angiogenic factors, anti-inflammatory factors, neuroprotective factors, and neurotrophic factors, which are produced and secreted from the NSCSs may be accumulated in the hydrogel.

More preferably, the ECM may include fibronectin, laminin, and collagen type IV, but embodiments of the present disclosure are not limited thereto.

More preferably, the angiogenic factors may include at least one angiopoietin (ANGPT), such as ANGPT-1, ANGPT-2, ANGPT-3, and ANGPT-4, a vascular endothelial growth factor (VEGF), or a platelet-derived growth factor (PDGF), but embodiments of the present disclosure are not limited thereto.

More preferably, the anti-inflammatory factors may include interleukin (IL), such as IL-6 or IL-10, or a transforming growth factor (TGF), such as TGF-β, but embodiments of the present disclosure are not limited thereto.

More preferably, the neurotrophic factors may include at least one neurotrophin (NT) selected from the group consisting of a nerve growth factor (NGF), a brain-derived growth factor (BDNF), NT-3, and NT-4/5; at least one glial cell line-derived neurotrophic factor (GDNF) selected from the group consisting of GDNF and artemin (ARTN); at least one ephrin (EFN) selected from the group consisting of EFN A1, EFN A2, EFN A4, EFN A5, EFN B1, EFN B2, and EFN B3; at least one ciliary neurotrophic factor (CNTF) selected from the group consisting of CNTF, a leukemia inhibitory factor (LIF), and IL-6; a glial maturation factor (GMF); or neuregulin (NRG) or an insulin-like growth factor (IGF)-1, but embodiments of the present disclosure are not limited thereto.

More preferably, the neuroprotective factors may include at least one fibroblast growth factor (FGF) selected from the group consisting of FGF-7, FGF-9, FGF-16, FGF-19, FGF-12, FGF-5, FGF-6, and FGF-14, but embodiments of the present disclosure are not limited thereto.

Preferably, the non-stressed culture condition (i.e. free-floating culture condition) of step (4) may induce cell-mediated hydrogel compaction so that culture media and water in the hydrogel may be extruded.

Preferably, the multilayered cell sheet of the NCSCs may consist of about 10 layers to about 50 layers, but embodiments of the present disclosure are not limited thereto.

In addition, the present disclosure provides a multilayered cell sheet of NCSCs, the multilayered cell sheet including: a hydrogel in which the NCSCs are embedded; and ECM, angiogenic factors, anti-inflammatory factors, neuroprotective factors, and neurotrophic factors that are secreted from the NCSCs and accumulated in the hydrogel.

Preferably, the hydrogel may be a mixed hydrogel of collagen and fibrinogen, but embodiments of the present disclosure are not limited thereto.

In one embodiment, the hydrogel in the multilayered cell sheet of the NCSCs does not induce inflammatory and foreign reactions in vivo, and may have biodegradable characteristics that the hydrogel is completely degraded in vivo within 3 days to 3 weeks.

Preferably, the NCSCs may have a density in a range of about $1 \times 10^6$/ml to about $1 \times 10^8$/ml, but embodiments of the present disclosure are not limited thereto.

Preferably, the multilayered cell sheet of the NCSCs may consist of about 10 layers to about 50 layers, but embodiments of the present disclosure are not limited thereto.

In the multilayered cell sheet of the NCSCs of the present disclosure, a cell membrane may remain intact, and adhere on a hydrogel polymer and an ECM support, so that stable structural characteristics may be resulted. Accordingly, a survival rate of the NCSCs, which are transplanted via an inflammatory mediator or from damage mediated by excessively oxidized free radicals on a damaged site, may be increased.

In addition, the present disclosure provides a composition for treating spinal cord injury, the composition including, as an active ingredient, a multilayered cell sheet of NCSCs or a culture product of the multilayered cell sheet of the NCSCs.

Preferably, the composition may promote axon regrowth and remyelination, inhibit an inflammatory response, and promote angiogenesis, in damaged spinal cord and/or peripheral nerves.

In particular, the multilayered cell sheet of the NCSCs of the present disclosure provides a cell therapeutic method of recovering regeneration of damaged spinal cord through a mechanism that induces regeneration of tissues of the spinal cord by using inflammation inhibitory factors, neuroprotective and neurotrophic factors, and angiogenic factors that are secreted from the NCSCs.

In one embodiment, the multilayered cell sheet of the NCSCs of the present disclosure may improve the delivery efficiency thereof in the spinal cord through directly localized transplantation to an injured site within the spinal cord, rather than a systemic administration route. In addition, when implanted into the spinal cord, the multilayered cell sheet may be locally delivered into dura or dura matter that surrounds the damaged spinal cord covering or to the outside of the dura or dura matter, thereby preventing secondary spinal cord injury accompanied during the injection.

In addition, the multilayered cell sheet of the NCSCs of the present disclosure may increase a retention rate and an engraftment rate of a cell graft site may be increased when locally delivered to the spinal cord. Then, the locally delivered multilayered cell sheet of the NCSCs may be integrated with a surrounding tissue of the spinal cord and a blood vessel and survive for more than 4 weeks, thereby continuously secreting anti-inflammatory factors, neuroprotective factors, neurotrophic factors, and an angiogenic factors for the improvement of regeneration of the damaged spinal cord and functional recovery of the spinal cord.

In addition, the present disclosure provides a composition for treating brain injury, the composition including, as an active ingredient, a multilayered cell sheet of NCSCs and a culture product of the multilayered cell sheet.

Preferably, the composition may prevent neuron damage and promote neuron growth and differentiation.

In addition, the present disclosure provides a composition for treating injury of peripheral nerves, the composition including, as an active ingredient, a multilayered cell sheet of NCSCs and a culture product of the multilayered cell sheet.

MODE OF THE INVENTION

Hereinafter, exemplary embodiments will be described in detail to promote understanding of the present disclosure. It should be noted, however, that the following examples are illustrative examples of embodiments and are not intended to limit the scope of the present disclosure in any way. These examples are provided so that this disclosure will be thorough and complete, and will fully convey the concept of examples to those skilled in the art.

<Example 1> Isolation and Culture of Neural Crest Stem Cells (NCSCs) Derived from Adult Peripheral Nerves (PNs)

After approval of the Ethics Commission of College of Medicine, Inje University, isolation of NCSCs from adult PNs (hereinafter, referred to as PN-NCSCs) was attempted. The isolation of the PN-NCSCs was performed according to the method disclosed in KR 10-1389851. PNs were donated by a brain-dead patient, and soft tissues and epineuriums around the PNs were removed. Then, the resulting PNs were cut into fragments, each having a size of about 1 mm$^3$, and the fragments were washed 5 times with Dulbecco's phosphate-buffered saline (DPBS) solution. Meanwhile, collagen solution (0.5% porcine skin derived collagen, Matrixen™-PSC, Bioland Ltd., Daejeon, Korea) was mixed with reconstitution buffer solution (50 mM $NaHCO_3$, 40 mM HEPES, 0.01 N NaOH in deionized water) to prepare 0.2% collagen solution. The PN fragments were added to the 0.2% collagen solution, and 10 mL of the mixed solution was loaded onto a 100 mm culture plate. The culture plate was put in a 37° C. incubator for 2 hours to allow a reaction for gel formation. After a collagen hydrogel was formed, 10 ml of a cell culture medium was added thereto. Here, the cell culture medium had a composition of 90% DMEM (Welgene, Gyeongsan City, Korea), 10% fetal bovine serum (FBS, Gibco, Seoul, Korea), 10 ng/ml epidermal growth factor (EGF, Peprotech, Seoul, Korea), 2 ng/ml basic fibroblast growth factor (bFGF, Peprotech, Seoul, Korea), 10 ng/ml insulin-like growth factor (IGF, Peprotech, Seoul, Korea), and 10 µg/ml gentamicin (Invitrogen). Afterwards, the culture plate was subjected to incubation for 2 weeks with stirring on an orbital shaker at a speed of 30 rpm. A fresh cell culture medium was replaced every 2 days. The PN-NCSCs that were migrated from the PN fragments and outgrew on the collagen hydrogel were treated with collagenase type I (Worthington Biochemical, Lakewood, USA) to degrade the collagen hydrogel therefrom, and free PN-NCSCs were collected. The collected PN-NCSCs were expanded and cultured according to a monolayer culture method known in the art. At a density of more than 80%, the cultured PN-NCSCs were recovered from the cell culture plate by using 0.05% trypsin/EDTA (Sigma-Aldrich, Seoul, Korea), and then, subcultured.

As shown in FIG. 1, collagen was subjected to pH neutralization, and then, allowed for a reaction at a temperature of 37° C. for 2 hours, thereby forming a solidified collagen hydrogel. Consequently, PN tissues were able to be embedded three-dimensionally in the solidified collagen hydrogel.

As shown in FIG. 2, according to a three-dimensional long-term culture method using a collagen hydrogel support, migration of cells from PNs and proliferation of the cells were able to be induced. When PN fragments were embedded three-dimensionally in a collagen hydrogel, migration of the cells was observed within 24 hours. After 1 week of the incubation, the number of cells migrating from the PNs and proliferating in the hydrogel was increased. In addition, as the incubation period increased, the number of cells from the PNs and proliferating in the collagen hydrogel was also increased in a proportional manner. The collagen hydrogel containing the cells from the PNs and proliferating in the hydrogel were treated with 0.01% collagenase type I (Worthington Biochemical, Lakewood, USA) dissolved in DMEM:F12 medium, thereby degrading the collagen hydrogel and collecting outgrown cells isolated by the degradation of the collagen hydrogel. The collected cells, i.e., PN-NCSCs, were then expended and cultured according to a monolayer culture method known in the art. At a density of more than 80%, the cultured PN-NCSCs were recovered from a culture plate using 0.05% trypsin/EDTA (Sigma-Aldrich, Seoul, Korea), and then, cultured again. After long-term incubation for 2 weeks, the cells that were migrated and proliferated in a collagen hydrogel was treated with 0.01% collagenase, which is a collagen-degrading enzyme, thereby degrading the collagen hydrogel and collecting cells isolated by the degradation of the collagen hydrogel. Here, 95% or more of the cells isolated from the collagen hydrogel were survived, and the PN-NCSCs were proliferated in a typical spindle shape in the monolayer culture environment.

<Example 2> Proliferation Characteristics, Immunophenotype, and mRNA Expression Characteristics of NCSCs Derived from Adult PNs In vitro growth capability of PN-NCSCs was evaluated on the basis of colony forming unit-fibroblasts (CFU-Fs) and population doubling times (PDTs). The immunophenotype of the collected PN-NCSCs were analyzed using a confocal laser scanning microscope after immunofluorescence staining was performed on the cells. Antibodies used to evaluate the immunophenotype were a NCSC marker, such as $p75^{NTR}$, nestin, sox-10, and myelin protein 0 (P0), a neuron marker, such as neuronal class III β-Tubulin (Tuj1), a neuroglia cell marker, such as glial fibrillary acidic protein (GFAP), an oligodendrocyte marker, such as A2B5, oligodendrocyte transcription factor (Olig2), and myelin basic protein (MBP), a mesenchymal stem cell marker, such as CD105 and CD29, a hematopoietic stem cell marker, such as CD45, and a vascular endothelial cell marker, such as CD34.

1) Self-Renewal Capability of PN-NCSCs

The self-renewal capability of the PN-NCSCs was evaluated by CFU-Fs and PDTs. In order to evaluate a forming ability of CFU-F forming ability, the PN-NCSCs amplified according to the monolayer culture method were seeded on a 100-mm culture dish at a density of 5 cells/cm$^2$, and then, a proliferation culture medium was added thereto. On the 7$^{th}$ day of incubation, cells in the culture dish were fixed with 2% formalin for 10 minutes, and then, subjected to staining with 0.1% crystal violet (LabChem Inc., Pittsburgh, Pa.). The forming ability of the formed CFU-Fs was measured by counting the number of colonies having a diameter of 2 mm or more by using an image analysis program (Image J, NIH, Bethesda, Md.). Then, the number of colonies per seeded the number of the seeded cells was calculated and expressed as a percentage (%). Here, bone marrow-derived mesenchymal stem cells (BMSCs) were used as controls.

As shown in FIG. 3, the PN-NCSCs formed multiple colonies in the monolayer culture environment, and the colonies were composed of densely populated clusters of spindle cells. That is, it was confirmed that the PN-NCSCs had self-renewal capability. However, in the case of BMSCs which are controls, the BMSCs showed low colony formation, and spindle cells constituting the colonies of the BMSCs were populated at low density. As shown in FIG. 4, colonies were formed in less than 5% of the seeded cells in the control BMSCs, whereas colonies were formed in 30% or more of the seeded cells in the PN-NCSCs. In addition, the colony forming ability was maintained even in more than 33-passage subcultures. Accordingly, it was confirmed that the PN-NCSCs had high in vitro proliferation capacity.

2) In Vitro Proliferation Capacity of PN-NCSCs

In vitro proliferation capacity of the PN-NCSCs was evaluated by calculating population doubling time (PDT) in the monolayer culture environment. 1,000 of cells were seeded on a 48-multiwell culture plate, and then, cultured for 3 days. The cells were lysed by using CelLytic™ MT lysis reagent (Sigma-Aldrich, Seoul, Korea), and DNA content in a sample of the lysed cells was measured by using Quant-iT™ PicoGreen reagent (Molecular probes, Eugene, Oreg.). Fluorescent microplate reader, Synergy™ HT; Bio-Tek Instruments, Neufahrn, Germany) was used to measure a fluorescent intensity at an emission wavelength of 485 nm and an excitation wavelength of 540 nm. To convert the measured fluorescence intensity into cell population, a standard curve was obtained by using the cells isolated from the PN tissue, and the standard curve was used to convert the fluorescent intensity in the sample into cell population. PDT was then determined according to the following equation: PDT=[(days in exponential phase)/((log N2−log N1)/log 2)], wherein N1 is a cell population in an initial period in an exponential growth phase, and N2 is a cell population in a terminal period in the exponential growth phase.

As shown in FIG. 5, the PN-NCSCs were able to be subcultured more than 43 times in the monolayer culture environment. Until the 43-passage subcultures, the PDT of the PN-NCSCs was in a range of about 13.5 hours to about 15.8 hours in average, showing excellent in vitro proliferation capacity. In addition, as the subculture was performed more times, the PDT was slightly increased, but cell ageing was not shown until the 43-passage subcultures. Accordingly, it was confirmed that the cells isolated from the PN tissue had excellent self-renewal capability and proliferation capability.

3) Immunophenotypic Characteristics of PN-NCSCs

To analyze immunophenotypic characteristics of the PN-NCSCs, immunofluorescence staining was performed. $3\times10^4$ cells amplified and cultured in the cells the monolayer culture environment were seeded on a 4-multiwell chamber slide (Lab-Tek™ II Chamber Slide™ System, Thermo Fisher Scientific, Seoul, Korea), and then, cultured for 1 day. Afterwards, the cells were fixed with a solution of acetone/methanol mixed at 1:1. To inhibit non-specific reaction of antibody, the cells were reacted with 5% bovine serum albumin (BSA, Fraction V, IgG-free, Thermo Fisher Scientific) at room temperature for 30 minutes. Primary antibodies used for the evaluation of the immunophenotypic characteristics were a NCSC marker, such as $p75^{NTR}$, nestin, and sox-10, a neuron marker, such as neuronal class III β-tubulin (Tuj1), an astrocyte (or neuroglia cell) marker, such as glial fibrillary acidic protein (GFAP), an oligodendrocyte marker, such as A2B5, oligodendrocyte transcription factor (Olig2), and myelin basic protein (MBP), a Schwann cell marker, such as myelin protein 0 (P0), a stromal cell marker, such as CD105 and CD29, a hematopoietic stem cell marker, such as CD45, and a vascular endothelial cell marker, such as CD34. Then, signals were detected by a reaction with the corresponding primary antibody, isotype-matched Alexa Fluor 488-conjugated IgG, at room temperature for 45 minutes. Nuclei of the cells were stained by using 10 µg/ml DAPI (4′,6-diamidino-2-phenylindole, Invitrogen) solution, and then, were analyzed by using a confocal microscope. BMSCs and neural crest-derived tumor cell line, PC12 cells, were used as controls.

As shown in FIG. 6, the PN-NCSCs that were amplified in vitro according to monolayer culture method showed an expression rate of the NCSC markers as follows: $p75^{NTR}$ (95.6%±2.67%), Sox-10 (88.2%±3.6%), and nestin (95.7%±2.7%). The PC12 cells which is a neural crest-derived tumor cell line showed an expression rate of NCSC 1.1%). However, the BMSCs showed a high expression rate of $p75^{NTR}$ (41.7%±3.0%), whereas the BMSCs showed a low expression rate of Sox-10 (2.2%±1.4%) and nestin (1.1%±1.1%). According to these results, it was confirmed that the cells isolated from the PNs according to the three-dimensional long-term culture method have the same immunophenotypic characteristics as neural crest-originated cells originated from.

As shown in FIG. 7, the PN-NCSCs were subjected to analysis of expression rates of neuron markers and neuroglia cell markers. The PC12 cells which is a neural crest-derived tumor cell line showed a low expression rate of a neuron marker (Tuj1: 2.9%±0.9%) an astrocyte (or neuroglia cell) marker (GFAP: 32.5%±3.2%), oligodendrocyte markers (A2B5: 69.9%±6.7% and MBP: 23.1%±1.1%). However, it was confirmed that cells differentiated into neurons and neuroglia cells during the incubation were mixed with the PN-NCSCs. However, in the case of the PN-NCSCs and the BMSCs, neuron, astrocyte (or neuroglia cell), oligodendrocyte, Schwann cell markers were detected in less than 1%, meaning that cells having immunophenotypic characteristics of neurons and neuroglia cells were not detected. According to these results, it was confirmed that the PN-NCSCs are not matured neural crest cells so that the PN-NCSCs have the same immunophenotypic characteristics as undifferentiated NCSCs.

As shown in FIG. 8, CD29 and CD105, which are known as stromal cell markers, showed an expression rate of at least 95% in all of the PC12 cells, the PN-NCSCs, and the BMSCs. In the same manner as in the BMSCs, it was confirmed that the PC12 cells and the PN-NCSCs were stroma-dependent cells.

As shown in FIG. 9, by using CD34 and CD45, which are a vascular endothelial cells marker and a hematopoietic cell marker, respectively, cells derived from hematopoietic cells and vascular cells during the isolation culture of the PN-NCSCs were subjected to determine the contamination of the cells. With respect to the PC12 cells, the NCSCs, and the BMSCs, expression rates of CD34 and CD45 were each less than 1%, meaning that there was no contamination by the cells derived from hematopoietic cells and vascular cells. According to these results, it was confirmed that the cells migrating and proliferating from the PNs according to the three-dimensional long-term culture method were PN-NCSCs having high purity without contamination by vascular endothelial cells and hematopoietic cells.

4) mRNA Expression Characteristics of PN-NCSCs Derived From Nerves

In the same manner as in Example 1, cells were isolated from PNs, and then, amplified and cultured according to a two-dimensional monolayer culture method. To confirm the expression of mRNA specific to a neural crest lineages, TRI-reagent® (Thermo Scientific) was used to isolate RNA of the cells. Then, to evaluate the mRNA expression of neural crest-specific genes, such as Sox-2, Sox-10, and Fgf5, the cells were subjected to reverse-transcriptase quantitative polymerase chain reaction (RT-qPCR), followed by electrophoresis assay. Here, PC12 cells and BMSCs were used as positive and negative controls, respectively.

As shown in FIG. 10, in the PN-NCSCs migrating and proliferating from the PN tissue according to the three-dimensional long-term culture method, PC12 cells and mRNA of neural crest cell-related genes, such as Sox-2, Sox-10, Dlx2, Tcfap2a, Erbb3, and Fgf5, were expressed. Meanwhile, in the case of BMSCs that are controls, a neural crest cell marker and an ectodermal cell marker were negative, meaning that these markers were not expressed. Accordingly, it was confirmed that the cells migrating and proliferating from the PNs according to the three-dimensional long-term culture method were neural crest-derived cells.

<Example 3> Multipotency of Adult PN-NCSCs into Neural Crest Lineage Cells

1) Differentiation Potential into Neurons and Glia Cells 200,000 PN-NCSCs were seeded on a 24-multi cell plate (Ultra-Low attachment plates, Sigma-Aldrich), which inhibits cell adhesion, and then, cultured in a non-stressed culture conditions. In the non-stressed culture conditions, the PN-NCSCs were prevented from adhering to the culture plate while cell-to-cell adhesion was induced to induce microsphere formation. To induce differentiation into neurons and glia cells, a differentiation medium supplemented with 99% Dulbecco's Minimum Essential Medium (DMEM), 1% calf serum (Gibco), 0.1 µM dexamethasone (Sigma-Aldrich), 50 µg/ml ascorbic acid (Sigma-Aldrich), and 0.1% dimethyl sulfoxide (DMSO; Sigma-Aldrich) was added to the culture plate, and the cells were cultured for 5 days. After incubation for 5 days in the non-stressed culture conditions, the microsphere was collected and fixed with 4% neutral formalin, thereby preparing a paraffin block. A paraffin fragment having a thickness of 5 µm was obtained from the paraffin block, and then, subjected to immunofluorescence staining. Depending on whether a cell-specific marker is expressed, differentiation of the PN-NCSCs in the microsphere into neurons and glia cells was evaluated. Antibodies used herein to evaluate whether the cell-specific marker is expressed are a neuron marker, such as neuronal class III β-Tubulin (Tuj1) and neurofilament-200 (NF200), an astrocyte (or glia cell) marker, such as glial fibrillary acidic protein (GFAP), an oligodendrocyte marker, such as A2B5, oligodendrocyte transcription factor (Olig2), and myelin basic protein (MBP), and a Schwann cell marker, such as P0.

As shown in FIG. 11, the differentiation potential of the PN-NCSCs into neurons and glia cells was to be identified. The PN-NCSCs in the microsphere formed in the non-stressed culture conditions showed positive expression with respect to neuron markers, such as Tuj1 and NF200, an astrocyte (or glia cell) marker, such as GFAP, oligodendrocyte markers, such as A2B5, Olig2, and MBP, a Schwann cell marker, such as P0, and a fibroblasts marker, such as SMA, and thus, it was confirmed that the PN-NCSCs had a differentiation potential into neurons and glia cells as the neural crest stem cells. However, the BMSCs used as controls were negative expression with respect to all of the corresponding markers, and thus, it was confirmed that the BMSCs had no differentiation potential into the neural crest lineage cells.

2) Differentiation Potential of PN-NCSCs into Adipocytes and Osteoblasts

To evaluate differentiation potential of PN-NCSCs into adipocytes, 200,000 cells were seeded on a 24-multiwell cell culture plate, and then, a differentiation medium including 90% DMEM supplemented with 10% calf serum, 0.5 mM 3-isobutyl-1-methylxanthine (Sigma-Aldrich), 1 µM dexamethasone, 0.2 unit/ml insulin (Sigma-Aldrich), and 200 µM indomethacin (Sigma-Aldrich) was added thereto. The cells were then cultured for 2 weeks. The differentiation into adipocytes was determined depending on accumulation of fats in cytoplasm, and 0.5% Oil Red O (Sigma-Aldrich) staining was performed for this analysis. To evaluate differentiation potential of PN-NCSCs into osteoblasts, 200,000 cells were seeded on a 24-multiwell cell culture plate, and then, a differentiation medium including 90% alpha-minimum essential medium (α-MEM; Welgene) supplemented with 10% calf serum, 0.1 µM dexamethasone, 10 mM β-glycerol phosphate (Sigma-Aldrich), 50 µM ascorbic acid was added thereto. The cells were then cultured for 2 weeks. The differentiation into osteoblasts was determined depending on accumulation of minerals, and alizarin red S (Sigma-Aldrich) staining was performed for this analysis.

As shown in FIG. 12, to evaluate differentiation potential of the PN-NCSCs isolated from peripheral nervous tissues into mesenchymal cell, differentiation into adipocytes and osteoblasts was induced separately. After 2 weeks of incubation, the accumulation of lipids in the cytoplasm was observed in the PN-NCSCs which were attempted to be induced into adipocytes. In addition, the morphology of the PN-NCSCs which were attempted to be induced into osteoblasts was cubical epithelium, and the accumulation of minerals was confirmed by alizarin red S staining. Accordingly, it was confirmed that the outgrown cells after the three-dimensional long-term culture of the PN tissues had a multipotency of being able to be differentiated into neural crest lineage cells and mesenchymal lineage cells.

<Example 4> Hydrogel Composition for Three-Dimensional Distribution and Culture of PN-NCSCs 1) Fibrin Hydrogel Composition for Three-Dimensional Culture of PN-NCSCs Human plasma-derived fibrinogen (Greencross, Seoul, Korea) was dissolved in DMEM medium containing 10 mM $CaCl_2$ to prepare a fibrinogen solution having a final concentration of 0.5%, and thrombin (Sigma, St. Louis, Miss.) was dissolved in DMEM medium to prepared a thrombin solution having a final concentration of 0.25 unit/ml. In addition, 100,000 or 1 million PN-NCSCs were mixed with 1 ml of the thrombin solution to prepare a thrombin solution in which the PN-NCSCs were distributed. Afterwards, the fibrinogen solution and the thrombin solution containing PN-NCSCs were mixed at a ratio of 1:1, and 100 µl of the mixed solution was transferred to a 24-multiwell cell culture plate. The cell culture plate was placed in an incubation at a temperature of 37° C., and the cells and fibrinogen were allowed for polymerization and crosslinking reactions for 2 hours to form fibrin hydrogel. Afterwards, a DMEM medium supplemented with 1% or 10% calf serum (CS) and 10 µg/ml gentamicin was added to the resulting cell culture plate. Then, the culture cell plate was placed in an orbital shaker for incubation at a speed of 15 rpm for 1 day. To determine the fibrinolysis activity of the PN-NCSCs and the role of a plasminogen activator inhibitor (PAI) in inhibiting the fibrinolysis activity of the PN-NCSCs, 100 µg/ml tranexamic acid was used as a PAI. Here, a fibrin hydrogel not containing a PAI (hereinafter, referred to as a PAI-free fibrin hydrogel) was used as a control group.

As shown in FIG. 13, a hydrogel of the PAI-free fibrin hydrogel was completely dissolved from the first day of incubation by the fibrinolysis activity of the PN-NCSCs, and thus, failed to provide a three-dimensional matrix that the PN-NCSCs could attach and proliferate. Here, the lysis of the fibrin hydrogel was proportional to the number of cells embedded in the hydrogel and the serum concentration. In the case of the fibrin hydrogel containing 100,000 PN- NCSCs, a hydrogel thereof was not dissolved on the first day of incubation regardless of the serum concentration and a three-dimensional matrix was successfully provided. However, from the second day of incubation, the hydrogel of the fibrin hydrogel began to dissolve. When 10% serum was contained in the culture medium, 90% or more hydrogel was dissolved, and when 1% serum was contained in the culture medium, 60% or more hydrogel was dissolved, so that the PN-NCSCs were adhered to the bottom of the culture plate for two-dimensional proliferation. Meanwhile, in the case of the fibrin hydrogel containing 100,000 PN-NCSCs, regardless of the serum concentration, a hydrogel of the fibrin hydrogel was dissolved from the first day of incubation, so that the PN-NCSCs were adhered to the bottom of the culture plate for two-dimensional proliferation. Meanwhile, 100 μg/ml of tranexamic acid was added to a culture medium and a hydrogel, and thus, when the fibrinolysis activity of the PN-NCSCs was inhibited, the fibrin hydrogel containing 100,000 PN-NCSCs embedded therein was able to inhibit the cell-mediated fibrinolysis activity thereof regardless of the serum concentration. As a result, the fibrin hydrogel was able to maintain its role as a three-dimensional matrix. Meanwhile, the fibrin hydrogel containing 100,000 PN-NCSCs failed to inhibit the cell-mediated fibrinolysis activity by using tranexamic acid regardless of the serum concentration.

As shown in FIG. 14, as compared with BMSCs and fibroblasts, the PN-NCSCs showed significantly high mRNA expression of urokinase-type plasminogen activator (uPA) and tissue plasminogen activator (tPA), which mediate fibrinolysis. That is, it is referred that uPA and tPA which are produced and secreted from the PN-NCSCs led to the lysis of the fibrin hydrogel. According to these results, it was confirmed that the fibrin hydrogel was available for three-dimensional culture of low-density PN-NCSCs, but was not suitable for three-dimensional culture of high-density PN-NCSCs.

2) Collagen-Fibrin Hydrogel Composition for Three-Dimensional Culture of PN-NCSCs For three-dimensional culture of PN-NCSCs, a hydrogel in which 0.2% collagen (porcine skin-derived collagen, Matrixen™-PSC, SK Bioland, Cheonan, Korea) or 0.25% fibrinogen (Greencross, Suwon, Korea) is mixed with 0.2% collagen was used. 0.5% collagen solution was mixed with a reconstitution buffer (50 mM NaHCO$_3$, 40 mM HEPES, 0.01 N NaOH in DW) to finally prepare 0.2% collagen solution. Human plasma-derived fibrinogen (Greencross, Seoul, Korea) was mixed with 0.2% collagen solution to prepare fibrinogen (0.5%)-collagen (0.2%) mixed solution, and thrombin (Sigma, St. Louis, Miss.) was dissolved in 0.2% collagen solution to prepare a thrombin solution having a final concentration of 0.25 unit/ml. Afterwards, $2 \times 10^6$ of PN-NCSCs were mixed with 50 μl of the thrombin/collagen mixed solution, and suspended therein. Then, the resulting PN-NCSCs were mixed with the fibrinogen/collagen mixed solution at an equal volume as the thrombin/collagen mixed solution, and then, transferred to a 10-mm O-ring adhered to the culture plate. For formation of the gel in the fibrinogen/collagen solution, the cells were allowed for gelation at a temperature of 37° C. for 1 hour. Afterwards, a DMEM medium was supplemented with 1% CS and 10 μg/ml of gentamicin, and was added to the culture cell plate. The culture cell plate was placed in an orbital shaker for incubation at a speed of 15 rpm for 3 days. Then, the fibrin/collagen hydrogel including the PN-NCSCs embedded therein was fixed with 1% neutral formalin, thereby preparing a paraffin block. A paraffin fragment obtained therefrom was subjected to hematoxylin eosin staining, thereby evaluating cellular cytoplasmic spreading and three-dimensional distribution of the cells.

As shown in FIG. 15, the PN-NCSCs were able to be embedded in a collagen hydrogel or a collagen/fibrin hydrogel. Unlike the case using a fibrin hydrogel, a hydrogel of the collagen hydrogel or the collagen/fibrin hydrogel maintained its function and structure as a substrate for three-dimensional incubation of the PN-NCSCs during a culture period for 3 days. A hydrogel of the collagen hydrogel including the PN-NCSCs embedded therein was contracted from the first day of incubation, and accordingly, the hydrogels encapsulating PN-NCSCs were detached from the O-ring and the culture plate. As the incubation period was longer, the hydrogel was more likely to be contracted. Meanwhile, the PN-NCSCs embedded in the collagen/fibrin mixed hydrogel were stably adhered to O-ring and the culture plate during 3 days of incubation, and a hydrogel thereof was neither contracted nor detached.

As shown in FIG. 16, the time required for phase transition from a solution to a gel in the collagen hydrogel was about 48 minutes in average, whereas the time required for phase transition from a solution to a gel in the collagen/fibrin mixed hydrogel was about 5 minutes in average. The three-dimensional distribution of the PN-NCSCs embedded in the hydrogel was evaluated in a morphological manner. In this regard, the PN-NCSCs embedded in the collagen hydrogel were distributed densely on the bottom of the hydrogel, whereas the PN-NCSCs embedded in the collagen/fibrin mixed hydrogel showed no difference in cell distribution by layers and were evenly distributed in a three-dimensional manner.

According to the results above, it was confirmed that the collagen hydrogel was provided to play a role as a matrix for three-dimensional culture of the PN-NCSCs, but due to delayed time for the phase transition, even three-dimensional distribution of the PN-NCSCs was not able to be provided. In addition, due to weak physicomechanical property, there is no resistance against the cell-mediated compaction so that the hydrogels encapsulating PN-NCSCs were spontaneously detached from the O-ring and the culture plate and then contracted. Meanwhile, due to fast phase transition time, the collagen/fibrin mixed hydrogel was able to achieve even three-dimensional distribution of the cells, and also showed resistant physicomechanical property against the cell-mediated hydrogel compaction.

<Example 5> Preparation of Multilayered Cell Sheet of the PN-NCSCs

1) Environment for Culturing a Multilayered Cell Sheet of the PN-NCSCs

An environment and a culture period for culturing a multilayered cell sheet of PN-NCSCs were to be set. According to the method described in Example 4, the 0.5% collagen solution was mixed with reconstitution buffer (50 mM NaHCO$_3$, 40 mM HEPES, 0.01 N NaOH in DW) to finally prepare 0.2% collagen solution. The human plasma-derived fibrinogen (Greencross, Seoul, Korea) was dissolved in 0.2% collagen solution to prepare a fibrinogen (0.5%)-collagen (0.2%) mixed solution, and thrombin (Sigma, St. Louis, Miss.) was dissolved in 0.2% collagen solution to prepare a thrombin solution having a final concentration of 0.25 unit/ml. $2 \times 10^6$ of PN-NCSCs were mixed with 50 μl of the thrombin/collagen mixed solution, and dispersed therein. Then, the mixed solution was mixed with the same amount of the collagen/fibrinogen solution, and transferred to a collagen/fibrin mixed hydrogel including the PN-NCSCs embedded therein was detached from the O-ring, and the PN-NCSCs were cultured in an environment in which a physical support was removed (free-floating culture conditions, non-stressed culture conditions) and in an environment in which a physical support was maintained after being cast on the O-ring (attached culture conditions, stressed culture conditions) for 3 days, respectively. A DMEM medium supplemented with 1% CS, 100 µg/ml tranexamic acid, 10 µg/ml gentamicin was added thereto, and a culture plate was incubated for 3 days with stirring on an orbital shaker at a speed of 15 rpm. To evaluate the culture environment-dependent characteristics of the PN-NCSCs of the hydrogel, a hydrogel was removed on the first day, second day, and third day of the incubation, fixed with 1% neutral formalin, thereby preparing a paraffin block. Hematoxylin eosin staining was performed thereon to evaluate the cell viability of the PN-NCSCs of the hydrogel.

As shown in FIG. 17, the frequency of apoptosis in which cytoplasmic blebbing and nuclear fragmentation are observed was significantly increased in the hydrogel of the PN-NCSCs that are cultured in the non-stressed culture conditions, as compared to the hydrogel of the PN-NCSCs that are cultured in the stressed culture conditions. The frequency of apoptosis of the PN-NCSCs in hydrogel that was cultured in the non-stressed culture conditions was $4.5\%\pm0.8\%$ on the first day, $8.5\%\pm2.4\%$ on the second day, and $12.7\%\pm2.6\%$ on the third day of the culture. The frequency of apoptosis was increased in proportion to the culture period in the non-stressed culture conditions. However, the frequency of apoptosis of the PN-NCSCs in the hydrogel cultured in the stressed culture conditions was as follows: about $0.3\%\pm0.1\%$ on the first day of culture, about $0.6\%\pm0.3\%$ on the second day of culture, about $0.7\%\pm0.2\%$ on the third day of culture. That is, the frequency of apoptosis of the PN-NCSCs was less than 1%. Accordingly, it was confirmed that, the longer the culture period in the non-stressed culture conditions was, the more the cells underwent cell-mediated hydrogel compaction. As a result, the supply of nutrients and oxygen into the hydrogel was blocked, resulting in cell damage and cell death. These results suggest that the stressed culture stressed culture conditions, which can suppress cell-mediated hydrogel compaction by a physical support to prevent cell damage in the multilayered cell sheet, and at time, which can continuously provide oxygen, nutrients, and metabolites exchange into the hydrogel, is required. In addition, these results indicate that significant differences were produced depending on the hydrogel, the composition of the culture medium, and the culture conditions for the three-dimensional distribution and culture of the PN-NCSCs in the hydrogel.

2) Control of Cell Layer of a Multilayered Cell Sheet of PN-NCSCs

According to the method described in Example 5, 0.5% collagen solution was mixed with reconstitution buffer (50 mM $NaHCO_3$, 40 mM HEPES, 0.01 N NaOH in DW) to finally prepare 0.2% collagen solution. Human plasma-derived fibrinogen (Greencross, Seoul, Korea) was dissolved in the 0.2% collagen solution to prepare fibrinogen (0.5%)-collagen (0.2%) mixed solution. Meanwhile, thrombin (Sigma, St. Louis, Miss.) was dissolved in the 0.2% collagen solution to prepare thrombin solution having a final concentration of 0.25 unit/ml. PN-NCSCs ($5\times10^5$, $1\times10^6$, $2\times10^6$, and $4\times10^6$) were mixed and dispersed in 50 µl of the thrombin/collagen solution, and then, mixed again with the thrombin/collagen solution at the same amount. The cultured cells were then transferred to a 10-mm O-ring attached to a culture plate, and were allowed for gel formation at a temperature of 37° C. Afterwards, culture medium containing 1% calf serum (CS), 100 µg/ml tranexamic acid, and 10 µg/ml gentamicin was added to DMEM, and the culture plate was subjected to incubation for 1 day while being on an orbital shaker at a speed of 30 rpm. 1 day after the incubation, the hydrogel containing the PN-NCSCs was detached from the O-ring, and then, cultured again in non-stressed culture conditions. Afterwards, the prepared multilayered cell sheet of the PN-NCSCs was fixed with 1% neutral formalin, thereby preparing a paraffin block. A paraffin section was obtained therefrom, and was subjected to hematoxylin eosin staining, thereby counting the number of cell layer.

As shown in FIG. 18, it was observed by a phase-contrast microscope that the PN-NCSCs embedded in the collagen/fibrin hydrogel showed cytoplasmic spreading after 6 hours of incubation in the stressed culture conditions. That is, it was confirmed that the cytoplasmic spreading was caused by adherence between polymer chains and cells in the hydrogel. In addition, it was also confirmed that the cell-to-cell adhesion increased with time, depending on the density of cells embedded in the hydrogel.

As shown in FIG. 19, it was shown that the number of cell layer in the hydrogel increased proportionally with the density of the PN-NCSCs embedded in the collagen/fibrin hydrogel. A multilayered cell sheet of the PN-NCSCs at the density of $5\times10^5$ consists of $15.3\pm3.2$ cell layers, a multilayered cell sheet of the PN-NCSCs at the density of $1\times10^6$ consists of $21.7\pm4.2$ cell layers, a multilayered cell sheet at the density of $4\times10^6$ consists of $31.8\pm3.7$ cell layers, and a multilayered cell sheet at the density of $4\times10^6$ consists of $43.9\pm5.1$ cell layers. That is, it was confirmed that the number of cell layer of the multilayered cell sheet can be easily controlled by controlling the cell density in the hydrogel.

3) Enhancement of Physicomechanical Property of a Multilayered Cell Sheet of the PN-NCSCs Through Cell-Mediated Hydrogel Contraction Due to the vulnerable physicomechanical property of the hydrogel, disadvantages that are difficult to operate have been suggested. The technique disclosed herein is intended to provide a method of enhancing the physicomechanical properties by condensing collagen fibers in the hydrogel through cell-mediated hydrogel compaction and extruding media and water contained in the hydrogel. According to the method described in Example 5, $2\times10^6$ of PN-NCSCs were mixed with 50 µl of a thrombin/collagen and dispersed therein. Then, the mixed solution was mixed with the same amount of a collagen/fibrinogen solution, and transferred to a 10-mm O-ring adhered to the culture plate. Afterwards, to form a gel from a solution, the mixed solution was allowed for a reaction for 2 hours at a temperature of 37° C. The collagen/fibrin mixed hydrogel including the PN-NCSCs embedded therein was cultured for 1 day while being attached to the O-ring and the culture plat. Afterwards, a culture medium containing 1% calf serum (CS), 100 µg/ml tranexamic acid, and 10 µg/ml gentamicin was added to DMEM, and the culture plate was subjected to incubation for 1 day while being on an orbital shaker at a speed of 15 rpm. 3 days after the incubation, the hydrogel containing the PN-NCSCs was detached from the O-ring, and then, cultured again in non-stressed culture conditions for 2 hours. Afterwards, the hydrogel was collected, fixed with 1% neutral formalin, thereby preparing a paraffin block. A paraffin section was obtained therefrom, and was subjected to Masson's trichrome staining, thereby evaluating cell distribution and changes in collagen fibers.

As shown in FIG. 20, to induce the cell-to-cell adhesion and the cell-to-collagen fiber adhesion, the cell-mediated compaction was induced in the non-stressed culture conditions after the cells were cultured in the stressed culture conditions stressed culture conditions for 1 day. The cell-mediated hydrogel compaction was able to extrude hydrogel water and to induce condensation of the hydrogel fibrils, resulting in assembly of a multilayered cell sheet. The hydrogel of the multilayered cell sheet of the PN-NCSCs before being subjected to the non-stressed culture conditions contained water. However, after 30 minutes of the culture in the non-stressed culture conditions, the water content decreased, the hydrogel constituent polymer fibrils were condensed in the form fibroid, and consequently, it was confirmed that the extracellular space becomes dense. After 2 hours of the culture in the non-stressed culture conditions, the polymer fibrils were condensed, and accordingly it was confirmed that the polymer fibrils in the form of fibroid become prominent and the extracellular space decreased and became dense. These results above suggest that the cell-to-cell adhesion and the cell-to-hydrogel polymer fibrils adhesion in the non-stressed culture conditions were induced non-stressed culture conditions, thereby providing a method of enhancing physicomechanical property of the multilayered cell sheet of the PN-NCSCs.

4) Accumulation of In Vitro Synthesized Extracellular Matrix, Neuroprotective/Trophic Factor, Angiogenic Factors, Anti-Inflammatory Factors, and Neurotrophic Factors in the Multilayered Cell Sheet of the PN-NCSCs In the present example, to enhance biological functions of the multilayered cell sheet of the PN-NCSCs, there is provided a technique of achieving accumulation of in vitro synthesized extracellular matrix and bioactive factors that are secreted by the PN-NCSCs of the multilayered cell sheet. According to the method described in Example 5, 0.5% collagen solution was mixed with a reconstitution buffer (50 mM $NaHCO_3$, 40 mM HEPES, 0.01 N NaOH in DW) to finally prepare 0.2% collagen solution. Human plasma-derived fibrinogen (Greencross, Seoul, Korea) was mixed with 0.2% collagen solution to prepare fibrinogen (0.5%)-collagen (0.2%) mixed solution, and thrombin (Sigma, St. Louis, Miss.) was dissolved in 0.2% collagen solution to prepare a thrombin solution having a final concentration of 0.25 unit/ml. Afterwards, $2 \times 10^6$ of PN-NCSCs were mixed with 50 μl of the thrombin/collagen mixed solution, and dispersed therein. Then, the resulting PN-NCSCs were mixed with the fibrinogen/collagen mixed solution at an equal volume as the thrombin/collagen mixed solution, and then, transferred to a 10-mm O-ring adhered to the culture plate. For formation of the gel in the fibrinogen/collagen solution, the cells were allowed for reaction at a temperature of 37° C. for 2 hours. After a hydrogel was formed, a collagen/fibrin mixed hydrogel in which the PN-NCSCs were embedded was detached from the O-ring. Then, the cells were cultured for 3 days separately in an environment where a physical support was removed (free-floating culture condition or non-stressed culture conditions) and in an environment where a physical support was maintained after being cast on the O-ring (attached culture conditions or stressed culture conditions). DMEM was supplemented with a culture medium containing 1% CS, 100 μg/ml of tranexamic acid, and 10 μg/ml of gentamicin in a culture plate, and the culture plate was placed in an orbital shaker for incubation at a speed of 15 rpm for 3 days. To evaluate characteristics of the PN-NCSCs in the hydrogel depending on the culture environments, the hydrogel was collected on the first, second, and third day of the incubation, and then, was fixed with 1% neutral formalin, thereby preparing paraffin blocks and paraffin sections. To evaluate the accumulation of extracellular matrix in the multilayered cell sheet, antibodies including anti-fibronectin, anti-laminin, ant-collagen type IV, and anti-fibrinogen were used for immunofluorescence staining, and a confocal microscope was used for observation.

To evaluate the expression of mRNA related to neuron growth and protection, angiogenesis, anti-inflammation, and neurotrophic activity, RNA was extracted from the multilayered cell sheet of the PN-NCSCs, followed by being subjected to real time-quantitative PCR. As a control group, RNA isolated from the PN-NCSCs that were amplified by monolayer culture, the BMSCs, and the spinal cord was used. The expression of mRNA related to neuron growth/protection was evaluated based on the expression of fibroblast growth factors (FGFs), such as FGF-1, FGF-2, FGF-4, FGF-5, FGF-6, FGF-7, FGF-8, FGF-9, FGF-10, FGF-11, FGF-12, FGF-13, FGF-14, FGF-16, FGF-20, and FGF-23. The expression of mRNA related to angiogenesis was evaluated based on the expression of angiopoietin (ANGPT)-1, -2, and -4, platelet-derived growth factor (PDGF)-C and -D, and vascular endothelial growth factor (VEGF)-A, -B, and -C. The expression of mRNA related to anti-inflammatory factors was evaluated based on the expression of interleukin (IL)-6 and 10 and transforming growth factor-β1 (TGFB1). The expression of mRNA related to neurotrophic factors that enhance the survival and protection of neurons, the growth of neuritis, and the remyelination was evaluated based on the expression of neurotrophin (NTF), glial-derived growth factor (GDNF), ephrin (EFN), ciliary neurotrophic factor (CNTF). NTF evaluated the expression of nerve growth factor (NGF), brain-derived growth factor (BDNF), and neurotrophin (NTF)-3 and 4/5, GDNF evaluated the expression of GDNF and artemin (ARTN), EFN evaluated the expression of EFNA1, EFNA2, EFNA3, EFNA4, EFNA5, EFNB1, EFNB2, and EFNB3, and CNTF evaluated the expression of leukemia inhibitory factor (LIF) and IL-6. The expression of uncategorized neurotrophic factors, such as neuregulin (NRG)-1, 2, 3, and 4 and glial maturation factor (GMF)-B and G, and insulin-like growth factor (IGF)-1 was evaluated.

As shown in FIG. 21, it was confirmed that basal lamina-like extracellular matrix, such as fibronectin, laminin, and collagen type IV, in the multilayered cell sheet was accumulated between cells after the PN-NCSCs in the collagen/fibrin hydrogel were embedded and cultured for 3 days in the stressed culture conditions. In was also confirmed that fibrin fibers were also detected so that fibronectin, laminin, and collagen type IV were produced in the PN-NCSCs by in vitro culture and then accumulated in the multilayered cell sheet.

As shown in FIG. 22, it was confirmed that the expression of mRNA of angiogenic factors in the multilayered cell sheet was significantly higher than that of BMSCs, after the PN-NCSCs in the collagen/fibrin hydrogel were embedded and cultured for 3 days in the stressed culture conditions. In detail, mRNAs of ANGP-1, ANGP-2, and ANGP-4 related to the growth, migration, differentiation, and angiogenesis were expressed 1.9 times, 45 times, and 31 times as much as the expression of BMSCs, respectively. In addition, mRNAs of PDGF-C and PDGF-D were expressed 1.9 times as much as the expression of BMSCs while mRNA of PDGF-D was expressed 4.8 times as much as the expression of BMSCs. In addition, mRNAs of VEGF-A, VEGF-B, and VEGF-C were expressed 9.5 times, 1.8 times, and 1.3 times as much as the expression of BMSCs, respectively. These results suggest that the PN-NCSCs of the multilayered cell sheet included angiogenic factors involved in the protection, growth, migration, differentiation, and angiogenesis of vascular endothelial cells.

As shown in FIG. 23, it was confirmed that the expression of mRNA related to alleviation or inhibition of inflammatory reaction in the multilayered cell sheet of the PN-NCSCs was significantly high. Based on the result the expression of representative anti-inflammatory cytokines, such as IL-6 and IL-10, was 4.2 times and 30 times as much as that of BMSCs, respectively, and that the expression of TGF-β31 was also 1.3 times as much as that of BMSCs, it was suggested that the multilayered cell sheet of the PN-NCSCs included anti-inflammatory factors involved in inhibition and alleviation of inflammation.

As shown in FIG. 24, it was confirmed that mRNA related to the proliferation, migration, differentiation, and protection of neurons in the multilayered cell sheet of the PN-NCSCs was significantly highly expressed. In addition, the expression of mRNAs of FGF-1, FGF-2, FGF-4, FGF-6, FGF-7, FGF-8, FGF-10 to FGF-14, FGF-16, FGF-18 to FGF-20, and FGF-23, which are subtypes of FGF related to the growth, migration, protection, and differentiation of neurons, was significantly increased compared to that of BMSCs, suggesting that the multilayered cell sheet of the PN-NCSCs included factors involved in the protection and growth of neurons.

As shown in FIG. 25, it was confirmed that the expression of mRNA inducing the proliferation, migration, differentiation, and protection of neurons in the multilayered cell sheet of the PN-NCSCs and the expression of mRNA related to the improvement of production of neurites and myelin were significantly high. In the multilayered cell sheet of the PN-NCSCs, the expression of mRNAs of NTF, GDNF, EFN, CNTF, NRG, and IGF-1 was 1.2 times to 51 times as much as that of BMSCs, suggesting that the multilayered cell sheet of the PN-NCSCs included neurotrophic factors.

As shown in FIG. 26, it was confirmed that mRNAs related to neuron regeneration, growth, and protection were expressed in the multilayered cell sheet of the PN-NCSCs. In comparison with the expression of BMSCs, mRNAs of BDNF, NT-3, and NT-4 mRNA were highly expressed only in the PN-NCSCs, and mRNA of GDNF was highly expressed. In addition, depending on the incubation period in the stressed culture conditions, the expression of mRNAs of BDNF, NT-3, and NT-4 increased. However, regardless of the incubation period, mRNAs of GDNF and NGF were highly expressed on the first day of culture. These results suggest that the multilayered cell sheet of the PN-NCSCs included neurotrophic factors in the neuron protection, regeneration, and axon regrowth.

5) Cell-to-Cell Adhesion and Cell-to-Extracellular Matrix Adhesion in the Multilayered Cell Sheet of the PN-NCSCs In the present example, to enhance structural stability of the multilayered cell sheet of the PN-NCSCs, there is provided a technique of inducing cell-to-cell adhesion of the PN-NCSCs in the multilayered cell sheet. According to the method described in Example 5, 0.5% collagen solution was mixed with a reconstitution buffer (50 mM NaHCO$_3$, 40 mM HEPES, 0.01 N NaOH in DW) to finally prepare 0.2% collagen solution. Human plasma-derived fibrinogen (Greencross, Seoul, Korea) was mixed with 0.2% collagen solution to prepare fibrinogen (0.5%)-collagen (0.2%) mixed solution, and thrombin (Sigma, St. Louis, Miss.) was dissolved in 0.2% collagen solution to prepare a thrombin solution having a final concentration of 0.25 unit/ml. Afterwards, 2×10$^6$ of PN-NCSCs were mixed with 50 µl of the thrombin/collagen mixed solution, and dispersed therein. Then, the resulting PN-NCSCs were mixed with the fibrinogen/collagen mixed solution at an equal volume as the thrombin/collagen mixed solution, and then, transferred to a 10-mm O-ring adhered to the culture plate. For formation of the gel in the fibrinogen/collagen solution, the cells were allowed for reaction at a temperature of 37° C. for 2 hours. After a hydrogel was formed, a collagen/fibrin mixed hydrogel in which the PN-NCSCs were embedded was detached from the O-ring. Then, the cells were cultured for 3 days separately in an environment where a physical support was removed (free-floating culture condition or non-stressed culture conditions) and in an environment where a physical support was maintained after being cast on the O-ring (attached culture conditions or stressed culture conditions). DMEM was supplemented with a culture medium containing 1% CS, 100 µg/ml of tranexamic acid, and 10 µg/ml of gentamicin in a culture plate, and the culture plate was placed in an orbital shaker for incubation at a speed of 15 rpm for 3 days. To evaluate characteristics of the PN-NCSCs in the hydrogel depending on the culture environments, the hydrogel was collected on the first, second, and third day of the incubation, and then, was fixed with 1 neutral formalin, thereby preparing paraffin blocks and paraffin sections. To evaluate the cell-to-cell adhesion and cell-to-extracellular matrix adhesion in the multilayered cell sheet, antibodies including anti-β-catenin and anti-CD29, respectively, were used for immunofluorescence staining, and a confocal microscope was used for observation.

As shown in FIG. 27, it was observed that β-catenin responsible for cell-to-cell adhesion was expression along the cell membrane of the PN-NCSCs, and the expression increased with increasing incubation period in the stressed culture conditions. In addition, it was observed that the expression of CD29 involved in cell-to-extracellular matrix adhesion increased with increasing incubation period in the stressed culture conditions, and that CD29 was expressed linearly along the cell membrane of the PN-NCSCs. These results suggest that, via in vitro culture in the stressed culture conditions, the adhesion between the PN-NCSCs in the hydrogel and the polymer fibrils in the hydrogel could be induced simultaneously with the cell-to-cell adhesion of the PN-NCSCs, thereby enhancing the structural stability of the multilayered cell sheet of the PN-NCSCs.

<Example 6> Effects of Bioactive Factors Derived From the Multilayered Cell Sheet of the PN-NCSCs on Neuron Protection and Proliferation, Axon Regrowth, and Anti-Inflammation 1) Preparation of Conditioned Medium Containing Bioactive Factors Secreted from the Multilayered Cell Sheet of the PN-NCSCs The effects of bioactive factors derived from the multilayered cell sheet of the PN-NCSCs on neuron protection and proliferation, axon regrowth, and anti-inflammation were evaluated. According to the method described in Example 5, 2×10$^6$ of PN-NCSCs were mixed with 50 µl of a thrombin/collagen mixed solution, and dispersed therein. Then, the resulting PN-NCSCs were mixed with a collagen/fibrinogen mixed solution at an equal volume as the thrombin/collagen mixed solution, and then, transferred to a 10-mm O-ring adhered to the culture plate. For formation of the gel in the thrombin/collagen mixed solution, the cells were allowed for reaction at a temperature of 37° C. for 2 hours. After a hydrogel was formed, a collagen/fibrin mixed hydrogel in which the PN-NCSCs were embedded was detached from the O-ring, and the cells were cultured for 3 days in the stressed culture conditions, followed by being cultured for 2 hours in the non-stressed culture conditions, thereby preparing a multilayered cell sheet of the PN-NCSCs. The prepared multilayered cell sheet of the PN-NCSCs was transferred onto a 100-mm culture plate, and 5 ml of a culture medium containing 1% CS and 99% DMEM was added thereto. After 24 hours of incubation, a conditioned media was prepared. After the culture medium was removed from the culture plate, a centrifugation process was performed thereon at a speed of 3,000 rpm for 10 minutes. Then, the supernatant was transferred to a sterilized tube, and the conditioned medium containing bioactive factors derived from the multilayered cell sheet of the PN-NCSCs was frozen for storage until experiments. In order to compare the biological ability of the bioactive factors derived from the multilayered cell sheet of the PN-NCSCs, a multilayered cell sheet of BMSCs was prepared in the same manner as the above, and then, a conditioned medium containing bioactive factors derived from the multilayered cell sheet of the BMSCs was prepared in the same manner as the above.

2) Neuron Protection Ability of the Conditioned Medium Containing the Bioactive Factors Derived from the Multilayered Cell Sheet of the PN-NCSCs Whether the bioactive factors derived from the multilayered cell sheet of the PN-NCSCs had neuron protection ability against radical oxygen species (ROS) was evaluated. 100,000 of SH-SY5Y cell lines derived from neuroblastoma cells were seeded on a 24-multiwell culture plate. A culture medium containing the bioactive factors secreted from the multilayered cell sheet of the PN-NCSCs and the multilayered cell sheet of the BMSCs was added to the culture plate. To induce ROS-mediated cell damage, 3 mM $H_2O_2$ was also added to the culture plate, and the culture plate was allowed for a reaction for 6 hours. Afterwards, a washing process was performed three times using PBS, and the number of cells was counted by using a Quant-iT™ PicoGreen® dsDNA reagent kit (Molecular probes, Eugene, Oreg.) after the cells were lysed by using CelLytic™ MT reagent (Sigma-Aldrich). Then, a fluorescent microplate reader (SpectraMax M2, Molecular Devices) was also used to measure fluorescence intensity of the cells at an emission wavelength of 480 nm and an excitation wavelength of 520 nm. To convert the measured fluorescence intensity to the number of cells, DNA obtained from calf thymus was used to obtain a standard curve, which is to be used to convert fluorescence intensity of a sample to the number of cells. To evaluate cell death, the SH-SY5Y cells were treated with caspase-3/7 using Apo 3/7 HTS™ assay kit (Cell Technology, Minneapolis, Minn.). After 6 hours of hydrogen peroxide ($H_2O_2$) treatment, 100 μl of a sample in which the SH-SY5Y cells were dissolved was reacted with an equal amount of 2×caspase-3/7 detection reagent at a temperature of 37° C. for 30 minutes, and the resultant was analyzed by measuring fluorescence intensity thereof using a fluorescent microplate reader (SpectraMax M2, Molecular Devices) at an emission wavelength of 488 nm and an excitation wavelength of 530 nm. Here, as a control group, a culture medium containing 1% CS and 99% DMEM was used.

As shown in FIG. 28, to confirm the neuron protection effect of the bioactive factors derived from the multilayered cell sheet of the PN-NCSCs, the $H_2O_2$-treated SH-SY5Y cells were treated with the conditioned medium derived from the multilayered cell sheet of the PN-NCSCs at concentrations of 10%, 50%, and 100%, so as to analyze the cell survival. The survival rate of the SH-SY5Y cells after being treated with $H_2O_2$ was less than about 80%. However, when the conditioned medium containing the bioactive factors derived from the multilayered cell sheet of the PN-NCSCs and the multilayered cell sheet of BMSCs was added, the effect of the bioactive factors on the neuron protection was confirmed. When the SH-SY5Y cells were treated with the conditioned medium containing the bioactive factors derived from the multilayered cell sheet of the PN-NCSCs at the concentration of 10%, the survival rate was about 84.4%±3.2%. Likewise, when the SH-SY5Y cells were treated with the conditioned medium at the concentration of 50%, the survival rate was about 92.4%±2.5%, and when the SH-SY5Y cells were treated with the conditioned medium at the concentration of 100%, the survival rate was about 99.9%±7.3%. Accordingly, it was confirmed that the bioactive factors derived from the multilayered cell sheet of the PN-NCSCs had ROS-mediated neuron protection ability in a concentration-dependent manner. The bioactive factors derived from the multilayered cell sheet of the PN-NCSCs exhibited greater neuron protection ability than those derived from the multilayered cell sheet of the BMSCs, but there was no statistical significance.

As shown in FIG. 29, the cell damage and cell death by ROS were mediated by caspase-3/7. To verify the cell protection ability of the bioactive factors derived from the multilayered cell sheet of the PN-NCSCs, the activity of caspase-3/7 on the $H_2O_2$-treated SH-SY5Y cells was analyzed. After treating with $H_2O_2$, caspase 3/7 activity was significantly increased in the SH-SY5Y cells. When treating with the conditioned medium containing the bioactive factors derived from the multilayered cell sheet of the PN-NCSCs, the activity of caspase-3/7 in the SH-SY5Y cells was significantly decreased in a concentration-dependent manner (*, P<0.05). In addition, the conditioned medium containing the bioactive factors derived from the multilayered cell sheet of the BMSCs also decreased the caspase 3/7 activity against ROS in the same manner as in the conditioned medium containing the bioactive factors derived from the multilayered cell sheet of the PN-NCSCs. Here, the degree of decrease was lower than that of the multilayered cell sheet of the PN-NCSCs. However, in comparison with the bioactive factors derived from the multilayered cell sheet of the PN-NCSCs, there was no statistically significant difference in inhibition of the caspase 3/7 activity.

3) Ability of the Conditioned Medium Including the Bioactive Factors Derived from the Multilayered Cell Sheet of the PN-NCSCs to Induce Neuron Growth To evaluate the ability of the bioactive factors derived from the multilayered cell sheet of the PN-NCSCs to induce neuron growth, 200,000 of SH-SY5Y cells were seeded on a 96-multiwell cell culture plate, and a conditioned medium including the bioactive factors derived from the multilayered cell sheet of the PN-NCSCs or the multilayered cell sheet of the BMSCs was added thereto at concentrations of 10%, 50%, and 100% for 3 days of incubation. To measure the number of the SH-SY5Y cells after 3 days of incubation, the SH-SY5Y cells were lysed by using CelLytic™ MT reagent (Sigma-Aldrich), and the number of the cells was counted by using a Quant-iT™ PicoGreen® dsDNA reagent kit (Molecular probes, Eugene, Oreg.). Then, a fluorescent microplate reader (SpectraMax M2, Molecular Devices) was also used to measure fluorescence intensity of the cells at an emission wavelength of 480 nm and an excitation wavelength of 520 nm. In addition, the ability of the bioactive factors derived from the multilayered cell sheet of the PN-NCSCs to induce neuron growth was evaluated based on uptake rates of 5-bromo-2'-deoxyuridine (BrdU; Sigma-Aldrich). BrdU was added to a culture medium every day to have a concentration of 10 μM therein, and then, cultured for 3 days. After 3 days of incubation, the cells were fixed with 2% buffered formalin solution, and a washing process using PBS was performed thereon three times. To inhibit non-specific reaction of the antibodies, the cells were treated with 5% bovine serum albumin for 30 minutes, and then, anti-BrdU primary antibodies were used for a reaction at room temperature for 2 hours. A washing process using PBS was performed thereon three times, and Dylight 488-conjugated secondary antibodies were used for a reaction at room temperature for 30 minutes, and the nuclei of the cells were stained with 10 μg/ml of 4',6-diamidino-2-phenylindole (DAPI, Invitrogen) solution. After being sealed with Pro-LongGold antifade reagent (Molecular Probe), a confocal microscope was used to evaluate whether BrdU was expressed or not. More than 1,000 of the cells were analyzed to evaluate the uptake of BrdU expressed in the nuclei.

As shown in FIG. 30, when the SH-SY5Y cells were treated with the conditioned medium including the bioactive factors derived from the multilayered cell sheet of PN-NCSCs at a concentration of 50%, the DNA content was about 126.2 ng/ml±1.9 ng/ml (*, P<0.01), and when the SH-SY5Y cells were treated with the same conditioned medium of a multilayered cell sheet of PN-NCSCs at a concentration of 100%, the DNA content was about 126.8 ng/ml±8.6 ng/ml. Accordingly, it was confirmed that the DNA content of the SH-SY5Y cells used herein was significantly increased compared to that of SH-SY5Y cells cultured in a culture medium not including the bioactive factors derived from the multilayered cell sheet of the PN-NCSCs or a conditioned medium including the bioactive factors derived from multilayered cell sheet of the BMSCs. However, when the SH-SY5Y cells were treated with the conditioned medium multilayered cell sheet of PN-NCSCs at a concentration of 10%, the DNA content was insignificantly increased. According to these results, it was confirmed that the bioactive factors derived from the multilayered cell sheet of the PN-NCSCs had were able to promote the growth of neurons.

As shown in FIG. 31, when treating with the conditioned medium including the bioactive factors derived from the multilayered cell sheet of the PN-NCSCs, the SH-SY5Y cells showed significantly increased uptake of BrdU compared to vehicles not including any bioactive factor and vehicles treated with the conditioned medium including the bioactive factors derived from the multilayered cell sheet of the BMSCs.

As shown in FIG. 32, as the concentration of the conditioned medium including the bioactive factors derived from the multilayered cell sheet of the PN-NCSCs increased, the uptake rate of BrdU by the SH-SY5Y cells was significantly increased in a concentration-dependent manner (*, P<0.05). When the concentration of the conditioned medium including the bioactive factors derived from the multilayered cell sheet of the PN-NCSCs was 50%, the uptake rate of BrdU was about 72.3%±6.1% (*, P<0.05), and when the concentration of the conditioned medium including the bioactive factors derived from the multilayered cell sheet of the PN-NCSCs was 100%, the uptake rate of BrdU was about 69.7%±5.1% (*, P<0.05), showing significantly increased uptake rate of the cells compared to the cells treated with a culture medium not including a bioactive factor. In addition, the uptake rate of BrdU was significantly high compared to the cells treated with the conditioned medium including the bioactive factors derived from the multilayered cell sheet of the BMSCs, indicating that the bioactive factors derived from the multilayered cell sheet of the PN-NCSCs had the property of promoting the growth of neurons.

4) Ability of the Conditioned Medium Including the Bioactive Factors Derived from the Multilayered Cell Sheet of the PN-NCSCs to Induce Neurite Outgrowth and Synapse To evaluate the effect of the bioactive factors derived from the multilayered cell sheet of the PN-NCSCs on the production of neural axon, 3,000 of SH-SY5Y cells per cm$^2$ were seeded on a 2-multiwell cell culture plate, and cultured in the conditioned medium derived the multilayered cell sheet of the PN-NCSCs or the multilayered cell sheet of the BMSCs at concentrations of 10%, 50%, and 100% for 7 days. Here, a group of cells treated with nerve growth factor (NGF) at a concentration of 50 ng/ml and a group of cells treated with a culture medium supplemented with 1% CS and 99% DMEM (i.e., vehicle) were used as control groups. After 7 d days of incubation, the cells were fixed with 2% buffered formalin solution, and a washing process using PBS was performed thereon three times. Then, a washing process using PBS containing 0.1% Triton X-100 solution that permeates the cell membrane was performed thereon for 5 minutes, and Oregon Green® 514-conjugated phalloidin (Molecular Probes) was treated therewith at a concentration of 1 μg/ml, thereby staining actin filaments in the cytoplasm. 100 of the cells were randomly selected and imaged by using a confocal fluorescent microscope, so that the length of neurite and the number of branching neurite were evaluated by using Image J program.

As shown in FIG. 33, the conditioned medium including the bioactive factors derived from the multilayered cell sheet of the PN-NCSCs significantly increased the neurite outgrowth of the SH-SY5Y cells. However, the conditioned medium including the bioactive factors derived from the multilayered cell sheet of the BMSCs and the control groups treated with 1% CS or NGF showed slight neurite outgrowth of SH-SY5Y cells.

As shown in FIG. 34, when treating with the conditioned medium including the bioactive factors derived from the multilayered cell sheet of the PN-NCSCs, the neurite outgrowth of SH-SY5Y cells was increased in a concentration-dependent manner. When treating with the conditioned medium including the bioactive factors derived from the multilayered cell sheet of the PN-NCSCs at a concentration of 100%, the length of neurite of SH-SY5Y cells was significantly increased compared to that of neurite of SH-SY5Y cells treated with vehicle or with the conditioned medium of the multilayered cell sheet of the BMSCs (*, P<0.01).

As shown in FIG. 35, the number of neurite branch was simultaneously analyzed by comparing with the number of neurite branch of SH-SY5Y cells that were treated with vehicle and the conditioned medium of the multilayered cell sheet of the BMSCs. Accordingly, it was confirmed that the SH-SY5Y cells treated with the conditioned medium of the multilayered cell sheet of the PN-NCSCs showed a significant increase regarding the number of neurite branch (*, P<0.05, **, P<0.01), indicating that the number of neurite branch was increased depending on the concentration of the conditioned medium. According to these results, it was confirmed that the bioactive factors derived from the multilayered cell sheet of the PN-NCSCs had neurotrophic activity ity that significantly increased the neuron protection and growth and neuritogenesis.

5) Anti-Inflammatory Ability of the Conditioned Medium Including the Bioactive Factors Derived from the Multilayered Cell Sheet of the PN-NCSCs To evaluate the ability of the bioactive factors derived from the multilayered cell sheet of the PN-NCSCs to inhibit inflammation, peritoneal monocytes obtained from the rat abdominal cavity were used. In detail, 30 ml of 0.9% physiological saline (NaCl saline) was injected to the abdominal cavity of Sprague Dawley rat, and after aspiration of injected normal saline from the rat peritoneum, a centrifugation process was performed thereon to isolate monocytes from the rat. Then, $4\times10^5$ of the isolated monocytes were seeded on a 96-multiwell cell culture plate, and treated with 1 µM lipopolysaccharide (LPS, Sigma-Aldrich) for 24 hours. When treating with LPS, the conditioned medium of the multilayered cell sheet of the PN-NCSCs or the multilayered cell sheet of the BMSCs multilayered cell sheet was also added at concentrations of 10%, 50%, and 100% and incubated for 1 day. Then, the amounts of tumor necrosis factor-alpha (TNF-α) and interleukin-1β (IL-1β, which are inflammatory cytokines secreted from the monocytes, were measured by using ELISA kit (R&D Systems, Minneapolis, Minn.) and fluorescent microplate reader (SpectraMax M2, Molecular Devices).

As shown in FIGS. 36 and FIG. 37, the significant anti-inflammatory effect of the conditioned medium of the multilayered cell sheet of the PN-NCSCs was able to be verified. After the activation of the monocytes was induced by the LPS treatment, the amount of TNF-α secreted from the monocytes following the treatment with the conditioned medium of the multilayered cell sheet of the PN-NCSCs was about 2.1 ng/ml±0.2 ng/ml when treated with the vehicle. However, the amount of TNF-α after treatment with the conditioned medium of the multilayered cell sheet of the PN-NCSCs at concentrations of 10%, 50%, and 100% was about 1.6 ng/ml±0.2 ng/ml, about 1.0 ng/ml±0.0 ng/m, and about 0.7 ng/ml±0.1 ng/ml, respectively. That is, it was confirmed that, as the concentration of the conditioned medium increased, the secretion of TNF-α from the monocytes was significantly inhibited (*, $P<0.05$). At the same time, the conditioned medium of the multilayered cell sheet of the PN-NCSCs significantly inhibited the secretion of IL-1β from the monocytes in a concentration-dependent manner. That is, when treating with the conditioned medium of the multilayered cell sheet of the PN-NCSCs at concentrations of 10%, 50%, and 100%, the amount of IL-1β secreted from the monocyte was about 0.9 ng/ml±0.1 ng/ml, about 0.7 ng/ml±0.1 ng/ml, and about 0.5 ng/ml±0.1 ng/ml, respectively. If not treated with the conditioned medium, the amount of IL-1β secreted from the monocyte was significantly higher than about 1.1 ng/ml±0.2 ng/ml. In addition, the conditioned medium of the multilayered cell sheet of the PN-NCSCs significantly decreased the secretion of TNF-α and IL-1β from the monocytes compared to the conditioned medium of the multilayered cell sheet of the BMSCs. According to these results, it was confirmed that the bioactive factors derived from the multilayered cell sheet of the PN-NCSCs had the ability to inhibit inflammatory responses.

<Example 7> Epidural Transplantation of the Multilayered Cell Sheet of the PN-NCSCs to Damaged Spinal Cord and Spinal Cord Regeneration/Protection Ability of the Multilayered Cell Sheet of the PN-NCSCs 1) Animal Model with Spinal Cord Injury (SCI)

As an animal model with SCI, Sprague Dawley rat weighing between 240 g and 260 g and being maintained in the general housing conditions was used after approval of the Ethics Commission of College of Medicine, Inje University. Regarding SCI, after removal of the spinous processes of the $8^{th}$ to $10^{th}$ thoracic vertebrae, an aneurysmal clip (S&T Vascular Clamps; Fine Science Tools, British Columbia, Canada) was used to induce SCI without disrupting the dura mater at a force of about 10 g/mm² for 1 minute at the spinous process of the $9^{th}$ thoracic vertebra. The multilayered cell sheet of the PN-NCSCs or the multilayered cell sheet of the BMSCs was transplanted over the dura meter of the damaged spinal cord. After damaging the spinal cord, a gelatin sponge (Spongostan®, Johnson & Johnson Medical, Skipton, UK) was covered over the damaged spinal for bleeding control, and the incision site was sutured. Following the surgery, an antibiotic, such as 50 µg gentamicin (Yuhan, Seoul, Korea), was administered for 3 days by an intramuscular injection, and an analgesic, such as 2 mg buprenorphine hydrochloride (Reckitt and Colman, Richmond, Va.), was administered for 2 days by a subcutaneous injection. Artificial urination was performed by pressing the bladder twice a day.

2) Engraftment of the Multilayered Cell Sheet of the PN-NCSCs in the Spinal Cord A multilayered cell sheet of the PN-NCSCs was prepared according to the method described in Example 5. To track the transplanted PN-NCSCs in vivo, the PN-NCSCs were labeled with 1 µM CM-Dil (Molecular Probe). $2\times10^6$ or $2\times10^7$ of the PN-NCSCs labeled with CM-Dil was mixed with 50 µl of a thrombin/collagen solution, and then, dispersed therein. Afterwards, the resulting PN-NCSCs were mixed with a collagen/fibrinogen mixed solution at an equal volume as the thrombin/collagen solution, and then, transferred to a 10-mm O-ring attached to a culture plate. For formation of the gel in the fibrinogen/collagen solution, the cells were allowed for reaction at a temperature of 37° C. for 2 hours. After a hydrogel was formed, a collagen/fibrin mixed hydrogel in which the PN-NCSCs were cultured for 3 days in the stressed culture conditions in which a physical support was supported while being placed in an orbital shaker for incubation at a speed of 15 rpm. Here, a composition of the culture medium included DMEM supplemented with a culture medium containing 1% CS, 100 µg/ml of tranexamic acid, and 10 µg/ml of gentamicin. Afterwards, the cells were detached from the O-ring, and cultured in the non-stressed culture conditions for 2 hours, thereby preparing a multilayered cell sheet of the PN-NCSCs. After the multilayered cell sheet of the PN-NCSCs was transplanted to the damaged spinal cord, images were obtained by using IVIS Lumina XR In Vivo Imaging System (Perkin Elmer, Seoul, Korea) on the third day of the transplantation. After the images were obtained, the multilayered cell sheet transplanted to the spinal cord was collected and fixed with 2% neutral formalin, thereby preparing paraffin blocks and paraffin sections. To evaluate angiogenesis in the transplanted multilayered cell sheet of the PN-NCSCs, antibodies including anti-α-smooth muscle actin (SMA) were used for immunofluorescence staining. Then, isotype-matched Alexa Fluor 488-conjugated secondary antibodies were used for a reaction at room temperature for 30 minutes, and the nuclei of the cells were stained with 10 µg/ml of 4',6-diamidino-2-phenylindole (DAPI, Invitrogen) solution. After being sealed with ProLong Gold antifade reagent (Molecular Probe), a confocal microscope was used to evaluate the expression.

As shown in FIG. 38, images of the damaged spinal cord and the transplanted multilayered cell sheet of the PN-NCSCs were obtained by using In Vivo Imaging System. The multilayered cell sheet of the PN-NCSCs was stably adhered to the SCI site, and the intensity of fluorescence derived from the transplanted PN-NCSCs was increased in proportion to the number of cells. According to the results above, it was confirmed that the multilayered cell sheet of the PN-NCSCs was able to be stably transplanted over the dura meter of the locally damaged spinal cord.

As shown in FIG. 39, after 3 days of the transplantation, the multilayered cell sheet of the PN-NCSCs was stably integrated into the dura meter of the damaged spinal cord. The multilayered cell sheet transplanted over the dura meter were composed of more than 50% of PN-NCSCs labeled with CM-DiI. It was also confirmed that CM-DiI positive cells well preserved their cytoplasmic and nuclear integrity, indicating that the cells were alive. It was also confirmed that microvascular ingrowth were identified in the multilayered cell sheet. Immunofluorescent staining with anti-SMA demonstrated that that the microvessel ingrowths were readily observed in the multilayered cell sheet of the PN-NCSCs, verifying that the transplanted multilayered cell sheet of the PN-NCSCs was engrafted. The microvessels in the multilayered cell sheet of the PN-NCSCs were positive to SMA, but CM-DiI was not expressed. That is, it is suggested that the microvessels in the multilayered cell sheet were originated from a recipient. In this regard, it was confirmed that the blood vessels were not by direct differentiation of the transplanted PN-NCSCs into blood vessels, but by the migration and growth of the blood vessels from surrounding tissues of recipient upon the bioactive factors secreted from the multilayered cell sheet. In addition, in the transplanted multilayered cell sheet of the PN-NCSCs, blood vessel circulation was made along with the transplanted site, and accordingly, it was confirmed that the multilayered cell sheet of the PN-NCSCs was engrafted over the SCI site. In addition, the multilayered cell sheet of the PN-NCSCs was only observed over the dura meter of the spinal cord, whereas the migration of the multilayered cell sheet of the PN-NCSCs into the damaged spinal cord was not observed.

3) Long-Term Survival Rate of the Multilayered Cell Sheet of the PN-NCSCs in the Spinal Cord To evaluate the long-term survival rate of PN-NCSCs transplanted to the multilayered cell sheet of the PN-NCSCs, the PN-NCSCs were infected with lentivirus including green fluorescent protein (GFP) genes. By using the PN-NCSCs including transgenic GFP transgene according to the method described in Example 5, a multilayered cell sheet of the PN-NCSCs was prepared. $2 \times 10^6$ of the PN-NCSCs harboring GFP transgene were mixed with 50 µl of a thrombin/collagen, and dispersed therein. Then, the resulting PN-NCSCs were mixed with a collagen/fibrinogen mixed solution at an equal volume as the thrombin/collagen mixed solution, and then, transferred to a 10-mm O-ring attached to the culture plate. For formation of the gel in the fibrinogen/collagen solution, the cells were allowed for reaction at a temperature of 37° C. for 2 hours. After a hydrogel was formed, a collagen/fibrin mixed hydrogel in which the PN-NCSCs were cultured for 3 days in the stressed culture conditions in which a physical support was supported while being placed in an orbital shaker for incubation at a speed of 15 rpm. Here, a composition of the culture medium included DMEM supplemented with a culture medium containing 1% CS, 100 µg/ml of tranexamic acid, and 10 µg/ml of gentamicin. Afterwards the cells were detached from the O-ring, and cultured in the non-stressed culture conditions for 2 hours, thereby preparing a multilayered cell sheet of the PN-NCSCs. After the multilayered cell sheet of the PN-NCSCs was transplanted to the damaged spinal cord, the damaged spinal cord was collected on the $3^{rd}$, $7^{th}$, $14^{th}$, and $28^{th}$ day of the transplantation and fixed with 2% neutral formalin, thereby preparing paraffin blocks and paraffin sections. The paraffin section was subjected to immunochemical staining using anti-GFP antibodies, and isotype-matched HRP-conjugated secondary antibodies were also used for a reaction at room temperature for 30 minutes, thereby developing color by using diaminobenzidine. Then, the nuclei of the cells were stained with hematoxylin. In addition, to evaluate the in vivo differentiation characteristics of the transplanted PN-NCSCs, double immunofluorescence staining was performed.

As shown in FIG. 40, it was confirmed that the multilayered cell sheet of the PN-NCSCs transplanted onto the dura meter of the damaged spinal cord remained. On the $3^{rd}$ day of the transplantation, the density of GFP-positive cells was highest on the dura meter, but the number of the GFP-positive cells was significantly decreased over time. Here, the GFP-positive cells that migrated into the spinal cord were not observed. The density of the GFP-positive cells was about $128.4/mm^2 \pm 21.5/mm^2$ on the $3^{rd}$ day of the transplantation, about $98.1/mm^2 \pm 12.1/mm^2$ on the $7^{th}$ day of the transplantation, about $56.2/mm^2 \pm 9.8/mm^2$ on the $14^{th}$ day of the transplantation, and about $11.5/mm^2 \pm 3.6/mm^2$ on the $28^{th}$ day of the transplantation. Accordingly, it was confirmed that the cell structure of GFP-positive cells over the dura meter remained intact and that the GFP-positive cells were survived. In addition, the GFP-positive cells showed morphological characteristics similar to those of fibroblasts in which the boundary of the cytoplasm in the spindle form was not clear.

As shown in FIG. 41, the PN-NCSCs transplanted over the dura meter were characterized by being differentiated into fibroblasts and vascular endothelial cells. Here, the PN-NCSCs expressing GFP were not expressed markers of neuron (Tuj1), astrocyte (or neuroglia cell, GFAP), oligodendrocyte (A2B5 and MBP), and Schwann cell (MPZ). However, it was confirmed that the GFP-positive PN-NCSCs covered the lumen of the microvascular structure, and at the same time, CD34 which is a vascular endothelial cell marker was expressed, so that transplanted PN-NCSCs directly differentiated into endothelial cells. At the same time, most of the GFP-positive cells were also SMA-positive, and thus, showed immunophenotypic characteristics similar to those of intraneural fibroblasts or myofibroblasts during wound restoration.

<Example 8> Functional Recovery of Injured Spinal Cords by the Implantation of Multilayered Cell Sheet of the PN-NCSCs 1) Recovery of Motor Function of SCI Animal An SCI rat model was prepared according to the method described in Example 7, and a multilayered cell sheet of the PN-NCSCs was prepared according to the method described in Example 5. The prepared multilayered cell sheet of the PN-NCSCs was transplanted onto the damaged spinal cord. For 84 days after the transplantation, to evaluate the motor function of the SCI animal, the rats were placed in a 100 cm×100 cm box and assessed according to the Basso, Beattie and Bresnahan (BBB) evaluation system. The motor function of each rat was recorded by video, and two different researchers evaluated the movement of the hindlimbs from 0 to 21 points according to joint movement, joint coordination, and weight support. Here, as control groups, a group of animals treated with the multilayered cell sheet of the BMSCs and a group of animals receiving no treatment was used.

As shown in FIG. 42, the SCI animal receiving treatment with the multilayered cell sheet of the PN-NCSCs or the multilayered cell sheet of the BMSCs multilayered cell sheet showed significant recovery of the motor function on the $7^{th}$ day after the transplantation. On the $14^{th}$ day after the transplantation, in the SCI animal receiving treatment with the multilayered cell sheet of the PN-NCSCs, significant recovery of the motor function was observed compared to the animal receiving treatment with the multilayered cell sheet of the BMSCs or the animal receiving no treatment. All the hindlimb showed movement from the $14^{th}$ day after SCI, and the average weight support was about 14.7±1.1 points on the $36^{th}$ day after the transplantation. Until the $63^{rd}$ day after the transplantation, the recovery of the motor function in the SCI animal receiving treatment with PN-NCSCs was continuously observed. However, there was no significant recovery of the motor function thereafter.

2) Recovery of Sensory Function of SCI Animal

An SCI rat model was prepared according to the method described in Example 7, and a multilayered cell sheet of the PN-NCSCs was prepared according to the method described in Example 5. The prepared multilayered cell sheet of the PN-NCSCs was transplanted onto the dura meter of the damaged spinal cord. To evaluate animal sensory ability, the SCI rats were placed in a 20 cm×20 cm box made of acrylic walls and a bottom with wire mesh. The animal was adapted in the box for 15 minutes, and then, a physical stimulation was applied to the soles of the animal feet by using a dynamic plantar aesthesiometer (Ugo Basile, Comerio, Italy). Through filaments that are thin enough to pass between the wire mesh with a force of about 2.5 g per second, up to 50 g of weight was pushed up, and the moment when the anima took foot off the wire mesh was weighed. Each leg was measured twice, and a high score was applied. Such a procedure was performed four times to obtain an average point. All measurements were performed weekly from the injury day (day 0) so that the presence of sensory allodynia was checked by measuring the response degree.

As shown in FIG. 43, from the $5^{th}$ week after the transplantation, the sensory function of the SCI rats to which the multilayered cell sheet of the PN-NCSCs was transplanted was significantly improved compared to that of the SCI rat to which the multilayered cell sheet of the PN-NCSCs was not transplanted or the SCI rats to which the multilayered cell sheet of the BMSCs was transplanted (*, P<0.05). Until the $4^{th}$ week after the transplantation, allodynia occurred in the SCI animal receiving treatment with the multilayered cell sheet of the PN-NCSCs or the multilayered cell sheet of the BMSCs, and these SCI animals also showed excessive response to filaments. However, after $5^{th}$ weeks of the transplantation, the hypersensitive sensory response to filaments and allodynia were significantly alleviated, whereas the sensory function of the SCI animal to which the multi-layered cell sheet of the PN-NCSCs was not transplanted was rapidly decreased and showed severe allodynia. According to the results above, it was confirmed that, when the multilayered cell sheet of the PN-NCSCs was transplanted to the SCI animal, the sensory function was evidently improved.

3) Recovery of Electrophysiological Function of SCI Animal

An SCI rats model was prepared according to the method described in Example 7, and a multilayered cell sheet of the PN-NCSCs was prepared according to the method described in Example 5. The prepared multilayered cell sheet of the PN-NCSCs was transplanted onto the dura meter of the damaged spinal cord. To evaluate electrophysiological function of the SCI animal, a probe was positioned in the subcutaneous layer of the animal head and in the tibialis nerve, and then, the motor nerve conduction and the sensory nerve conduction were evaluated.

As shown in FIG. 44, the significant recovery of the motor nerve conduction was observed in the SCI animal treated with the multilayered cell sheet of the PN-NCSCs. After 2 weeks of spinal cord injury, about 75.8% of motor evoked potentials were detected in the SCI rats treated with the multilayered cell sheet of the PN-NCSCs, whereas only 32.4% of motor evoked potential were detected in the animal receiving no treatment at all. However, after 4 weeks of spinal cord injury, the control group and the group of the SCI animal treated with the multilayered cell sheet of the PN-NCSCs, no significant difference was detected there between. In addition, on the $2^{nd}$ week of spinal cord injury, the SCI animal treated with the multilayered cell sheet of the PN-NSCS showed significantly fast conduction velocity, and on the $4^{th}$ week of spinal cord injury, the SCI animal treated with the multilayered cell sheet of the PN-NSCS showed significantly higher amplitude of motor evoked potential. However, in the control group and the group of the SCI animal treated with the multilayered cell sheet of the PN-NCSCs, somatosensory evoked potential was not detected. According to the results above, it was confirmed that the multilayered cell sheet of the PN-NCSCs had therapeutic effects on the spinal cord injury by inducing significant recovery of motor function, sensory function, and electrophysiological function.

<Example 9> Structural Recovery of Injured Spinal Cord by Multilayered Cell Sheet of the PN-NCSCs An SCI animal model was prepared according to the method described in Example 7, and a multilayered cell sheet of the PN-NCSCs was prepared according to the method described in Example 5. The prepared multilayered cell sheet of the PN-NCSCs was transplanted onto the dura meter of the damaged spinal cord. On the $2^{nd}$ and $4^{th}$ weeks after the transplantation, the spinal cord was collected, and the spinal cord injury and degree of tissue regeneration were evaluated by a morphological method.

1) Tissue Sparing of the Injured Spinal Cord by a Multilayer Cell Sheet of the PN-NCSCs On the $2^{nd}$ and the $4^{th}$ weeks of the SCI, the spinal cord including 4 mm of tail and 4 mm of head around the SCI site was collected and fixed with 2% neutral formalin for 6 hours, thereby obtaining paraffin block and paraffin sections in the longitudinal direction. Then, hematoxylin and eosin (H&E) staining and Luxol fast blue (LFB) staining were performed by using serial paraffin sections. In the LFB staining, 1% luxol fast blue (Solvent Blue 38; Thermo Fisher Scientific) was used for a reaction at a temperature of 56° C. for 2 hours. To remove hyperchromatic staining, a washing process using 95% ethyl alcohol was performed, and then, to increase the color contract of grey and white matters, 0.05% lithium carbonate solution was used for a reaction for 30 seconds. A washing process was performed for 30 seconds again by using 70% ethyl alcohol, and then, crystal violet was used to stain the nuclei. After completion of all staining processes, the slides were covered with a cover glass by using Malinol (Muto Chemical, Tokyo, Japan), and the stained slides were imaged by using NanoZoomer (Hamamatsu Photonics, Tokyo, Japan). The morphometric measurements were performed by using Image J software (NIH, Bethesda, Md.) to analyze the extent of damage to the spinal cord. The cavity lesions were assessed by using hematoxylin eosin staining slides, and the demyelination lesions were assessed by using LFB staining. Here, the lesion and demyelination areas, which correspond to 4 cm in the tail direction and 2 cm in the head area around the damaged spinal cord, were measured over the total area of the spinal cord, and were represented in percentages.

As shown in FIG. 45, on the $2^{nd}$ week after the multilayered cell sheet of the PN-NCSCs was transplanted on the SCI rat model, the structural recovery of the injured spinal cord was shown. Meanwhile, in the case of the SCI rats receiving no treatment at all, the cavity size in the spinal cord was about 77.9%±6.8%, but the cavity size after the SCI was significantly reduced to about 55.9%±4.3% in rats treated with multilayered cell sheet of the PN-NCSCs. In addition, the demyelination size was about 73.0%±9.1%, but the demyelination size was significantly reduced to about 58.1%±5.5% in the SCI rats treated with the multilayered cell sheet of the PN-NCSCs.

As shown in FIG. 46, on the $4^{th}$ week of the SCI, the degree of SCI was significantly reduced in the SCI animal treated with the multilayered cell sheet of the PN-NCSCs compared to the control group. Compared to the SCI on the $2^{nd}$ week, the cavity size was decreased the SCI on the $4^{th}$ week, and the SCI site was replaced by glial scar. The cavity size of the spinal cord treated with the multilayered cell sheet of the PN-NCSCs was significantly decreased compared to that of the spinal cord of the control group. The demyelination lesions were also decreased compared to the $2^{nd}$ week, and the remyelination was significantly increased in a group of SCI animal treated with the multilayered cell sheet of the PN-NCSCs.

2) Axon Regrowth in the Injured Spinal Cord by the Multilayered Cell Sheet of the PN-NCSCs After 2 weeks of the SCI, the number of axon fibers at the epicenter of injured spinal cord was assessed by Bodian's silver staining. In the Bodian's silver staining, paraffin sections were incubated with Protargol-S solution (Polysciences Inc., Warrington, Pa.) for a reaction at a temperature of 37° C. for 16 hours, and then, a washing process using distilled water was performed thereon. A reducing solution containing 0.1% hydroquinone (Sigma-Aldrich) and 0.05% sodium sulfite (Sigma-Aldrich) was used for a reaction for 5 minutes, and then, 0.5% gold chloride (Sigma-Aldrich) and 0.5% oxalic acid (Sigma-Aldrich) were used for a reaction for 5 minutes and 10 minutes, respectively, in the stated order. Then, a hypo solution containing 0.05% sodium thiosulfate (Sigma-Aldrich) was used for a reaction for 3 minutes, and then, the resulting solution was sealed. Images thereof were obtained by using NanoZoomer (Hamamatsu Photonics, Tokyo, Japan). In the obtained images, ventral horn, dorsal horn, and lateral gray matter areas of the gray matters of the injured spinal cord were determined, and the density of the axons in the SCI site was represented in percentages.

As shown in FIG. 47, on the $2^{nd}$ week of the SCI, the axons of the spinal cord were visualized by Bodian's silver staining, and density of axon fibers was evaluated by a morphological method. In the SCI animal to which the multilayered cell sheet of the PN-NCSCs was transplanted, the axon regrowth in the damaged spinal cord was significantly increased in all areas of the ventral horn, dorsal horn, and lateral gray matter areas, compared to the control group. In particular, in the SCI sites of the spinal cord treated with the multilayered cell sheet of the PN-NCSCs, the axon regrowth was observed, whereas it was difficult to observe such regeneration of the axons in the control group.

3) Recovery of Neural Circuits in Injured Spinal Cord by the Multilayered Cell Sheet of the PN-NCSCs To evaluate the extent of axon regrowth, the recovery of neural circuits was evaluated through anterograde neural tracing. After 2 weeks of the transplantation of the multilayered cell sheet of the PN-NCSCs, 10 µl of 10% biotinylated dextran amine (BDA, 10,000 M.W., Molecular Probe) was injected into the cerebral motor cortex. After 2 weeks of the BDA injection, the damaged spinal cord was collected and fixed with 4% neutral formalin for 6 hours, thereby preparing paraffin blocks and paraffin sections. The paraffin fragments were subjected to DAB color development after a reaction with HRP-polymerized streptavidin (Innogenex). Images were obtained by using NanoZoomer (Hamamatsu Photonics, Tokyo, Japan). In the obtained images, horn, dorsal horn, and lateral gray matter areas of the gray matters of the spinal cord were determined, and the density of the axon fibers in the SCI site was represented in percentages.

As shown in FIGS. 48 and 49, after 4 weeks of the SCI, the number of axon fibers containing BDA that was injected into the motor cortex was significantly increased in the animals transplanted with the multilayered cell sheet of the PN-NCSCs. The density of the BDA-positive axons around the SCI site was decreased, but there was no significant difference in the density of the axon fibers depending on the transplantation of the multilayered cell sheet of the PN-NCSCs. However, the density of the BDA-positive axons in the spinal cord at the caudal and the rostral site around the epicenter of injured site was significantly increased in the SCI animal treated with the multilayered cell sheet of the PN-NCSCs. According to the results above, it was confirmed that, upon the SCI, the multilayered cell sheet of the PN-NCSCs had the mechanism capable of alleviating cavity formation and demyelination that were caused by the SCI, and at the same time, promoting the axon regrowth, thereby improving the preservation and recovery of the structure of spinal cord.

<Example 10> Effects of the Multilayered Cell Sheet of the PN-NCSCs on Anti-Inflammatory and Nneurotrophic Activity in the Injured Spinal Cord To evaluate the inhibitory effect of a multilayered cell sheet of the PN-NCSCs on anti-inflammation, SCI was induced according to the method described in Example 7, and a multilayered cell sheet of the PN-NCSCs was prepared according to the method described in Example 5. Then, the prepared multilayered cell sheet of the PN-NCSCs was transplanted over the dura meter of the damaged spinal cord. After 3 days of the transplantation, the spinal cord including the SCI site including 1-cm rostral and 1-cm caudal areas was excised and dissolved with CelLytic™ MT reagent containing 0.1 M phenylmethylsulfonyl fluoride (Sigma-Aldrich) and protease inhibitor cocktail (Sigma-Aldrich). Afterwards, a centrifugation process was performed thereon at a temperature of 4° C. at a speed of about 12,000 rpm for 15 minutes, thereby collecting a supernatant. Then, amounts of inflammatory cytokines, such as TNF-α and IL-1β, in the supernatant were analyzed by using ELISA kit (R&D Systems, Minneapolis, Minn.). The expression of mRNA of neurotrophic factors, such as BDNF, GDNF, NGF, NT-3, and NT-4, in the damaged spinal cord was evaluated according to real time polymerase chain reaction. The spinal cord including the 1-cm rostral and 1-cm caudal segment around the epicenter of SCI site was collected and cut with scissors. Afterwards, the cut spinal cord was added to TRIzol, and RNA was isolated after tissue degradation. The isolated RNA was used to prepare hybridized DNA by using reverse transcriptase, followed by being subjected to a PCR reaction.

As shown in FIG. 50, the secretion level of inflammatory cytokines in the spinal cord to which the multilayered cell sheet of the PN-NCSCs was transplanted was significantly decreased. After 3 days of the SCI, the secretion of TNF-α and IL-1β, which are involved in inflammatory response, was increased. In comparison with the control group, the amounts of TNF-α (55.9 µg/ml±4.6 µg/ml, *, P<0.05) and IL-1β (261.8 µg/ml±4.5 µg/ml, *, P<0.05) were significantly lowered in the SCI rats to which the multilayered cell sheet of the PN-NCSCs was transplanted. In comparison with the control group, the secretion of TNF-α and IL-1β was significantly lowered in the SCI rats treated with the multilayered cell sheet of the BMSCs in the same manner as in the treatment using the multilayered cell sheet of the PN-NCSCs, and there was no significant difference according to cells constituting the multilayered cell sheet.

As shown in FIG. 51, in comparison with the spinal cord before SCI, the expression level of neurotrophic mRNAs was increased in the damaged spinal cord. In particular, in the spinal cord to which the multilayered cell sheet of the PN-NCSCs was transplanted, the expression of mRNAs of GDNF, NT-3, and NT-4 was significantly increased compared to the control group and the rats treated with the multilayered cell sheet of BMSCs. According to the results above, it was confirmed that the multilayered cell sheet of the PN-NCSCs exhibited biologic activity by secreting anti-inflammatory factors and neurotrophic factors to the damaged spinal cord to thereby protect the damaged spinal cord and promote the cord regeneration.

While particular embodiments have been particularly and described with reference to exemplary embodiments thereof, it will be understood by those of ordinary skill in the art that various changes in form and details may be made therein without departing from the spirit and scope of embodiments as defined by the following claims.

What is claimed is:

1. A method of manufacturing a multilayered cell sheet of neural crest stem cells (NCSCs) without stacking a cell sheet, in the order recited, consisting of:
   (1) isolating and culturing NCSCs from peripheral nerves (PN);
   (2) embedding the cultured NCSCs in a mixed hydrogel of collagen and fibrinogen consisting of collagen at a final concentration in a range of about 0.1% to about 1% and fibrinogen at a final concentration in a range of about 0.1% to about 1%,
   wherein step (2) comprises mixing the cultured NCSCs having a PN-NCSCs density in a range of about $1\times10^6$/ml to about $1\times10^8$/ml with the mixed hydrogel of collagen and fibrinogen in a solution phase and converting the solution phase to a gel phase so that the NCSCs are uniformly distributed in a three-dimensional manner in the mixed hydrogel of collagen and fibrinogen to have the multilayered cell sheet without stacking the cell sheet;
   (3) casting the mixed hydrogel of collagen and fibrinogen comprising the NCSCs embedded therein on a physical support so that the NCSCs are cultured under attached hydrogel culture conditions in which a physical support is applied,
   wherein the physical support is a mold having a circular, rectangular, or square shape; and
   (4) removing the physical support and culturing the resulting mixed hydrogel of collagen and fibrinogen under free floating hydrogel culture conditions, wherein a structure of the mixed hydrogel is maintained without the physical support, wherein the free floating hydrogel culture conditions of step (4) induces cell-mediated hydrogel compaction so that water and culture media in the hydrogel is extruded,
   wherein the culturing under the attached hydrogel culture conditions of step (3) comprises accumulating factors in the multilayered cell sheet, the factors including:
   1) Extracellular matrix (ECM) comprising fibronectin, laminin, and collagen type IV,
   2) angiogenic factors comprising at least one angiopoietin (ANGPT) comprising ANGPT-1, ANGPT-2, ANGPT-3, and ANGPT-4, a vascular endothelial growth factor (VEGF), or a platelet-derived growth factor (PDGF),
   3) anti-inflammatory factors comprising interleukin (IL) comprising IL-6 or IL-10, or a transforming growth factor (TGF) comprising TGF-β,
   4) neurotrophic factors comprising:
   at least one neurotrophin (NT) selected from the group consisting of a nerve growth factor (NGF), a brain-derived growth factor (BDNF), NT-3, and NT-4/5;
   at least one glial cell line-derived neurotrophic factor (GDNF) selected from the group consisting of GDNF and artemin (ARTN);
   at least one ephrin (EFN) selected from the group consisting of EFN A1, EFN A2, EFN A4, EFN A5, EFN B1, EFN B2, and EFN B3;
   at least one ciliary neurotrophic factor (CNTF) selected from the group consisting of CNTF, a leukemia inhibitory factor (LIF), and IL-6;
   a glial maturation factor (GMF); or
   neuregulin (NRG) or an insulin-like growth factor (IGF)-1, and
   5) neuroprotective factors comprising at least one fibroblast growth factor (FGF) selected from the group consisting of FGF-7, FGF-9, FGF-16, FGF-19, FGF-12, FGF-5, FGF-6, and FGF-14, which are produced and secreted from the NSCSs, in the mixed hydrogel of collagen and fibrinogen.

2. The method of claim 1, wherein the multilayered cell sheet of the NCSCs consists of about 10 layers to about 50 layers.

* * * * *